US010450269B1

(12) United States Patent
Xu et al.

(10) Patent No.: US 10,450,269 B1
(45) Date of Patent: Oct. 22, 2019

(54) COMPOUNDS AND USES THEREOF FOR THE MODULATION OF HEMOGLOBIN

(71) Applicant: Global Blood Therapeutics, Inc., South San Francisco, CA (US)

(72) Inventors: Qing Xu, South San Francisco, CA (US); Zhe Li, San Diego, CA (US)

(73) Assignee: Global Blood Therapeutics, Inc., South San Francisco, CA (US)

( * ) Notice: Subject to any disclaimer, the term of this patent is extended or adjusted under 35 U.S.C. 154(b) by 0 days.

(21) Appl. No.: 16/446,331

(22) Filed: Jun. 19, 2019

Related U.S. Application Data

(63) Continuation of application No. 16/186,275, filed on Nov. 9, 2018, which is a continuation of application No. 14/776,726, filed as application No. PCT/US2014/022769 on Mar. 10, 2014, now abandoned.

(60) Provisional application No. 61/905,803, filed on Nov. 18, 2013.

(51) Int. Cl.

| | | |
|---|---|---|
| *C07D 207/08* | (2006.01) | |
| *C07D 403/06* | (2006.01) | |
| *C07D 335/02* | (2006.01) | |
| *C07D 401/12* | (2006.01) | |
| *C07D 211/16* | (2006.01) | |
| *C07C 271/16* | (2006.01) | |
| *C07D 207/34* | (2006.01) | |
| *C07D 211/22* | (2006.01) | |
| *C07D 211/60* | (2006.01) | |
| *C07D 211/78* | (2006.01) | |
| *C07D 213/81* | (2006.01) | |
| *C07D 241/04* | (2006.01) | |
| *C07D 265/30* | (2006.01) | |
| *C07D 279/12* | (2006.01) | |
| *C07D 309/08* | (2006.01) | |
| *C07D 309/28* | (2006.01) | |
| *C07D 333/38* | (2006.01) | |
| *C07D 207/48* | (2006.01) | |
| *C07D 401/06* | (2006.01) | |

(52) U.S. Cl.
CPC .......... *C07D 207/08* (2013.01); *C07C 271/16* (2013.01); *C07D 207/34* (2013.01); *C07D 207/48* (2013.01); *C07D 211/16* (2013.01); *C07D 211/22* (2013.01); *C07D 211/60* (2013.01); *C07D 211/78* (2013.01); *C07D 213/81* (2013.01); *C07D 241/04* (2013.01); *C07D 265/30* (2013.01); *C07D 279/12* (2013.01); *C07D 309/08* (2013.01); *C07D 309/28* (2013.01); *C07D 333/38* (2013.01); *C07D 335/02* (2013.01); *C07D 401/06* (2013.01); *C07D 401/12* (2013.01); *C07D 403/06* (2013.01)

(58) Field of Classification Search
None
See application file for complete search history.

(56) References Cited

U.S. PATENT DOCUMENTS

| | | | |
|---|---|---|---|
| 3,236,893 | A | 2/1966 | Blout et al. |
| 4,062,858 | A | 12/1977 | Hoehn et al. |
| 4,410,537 | A | 10/1983 | Kneen |
| 4,478,834 | A | 10/1984 | Shroff et al. |
| 4,535,183 | A | 8/1985 | Kneen |
| 5,185,251 | A | 2/1993 | Chen et al. |
| 5,202,243 | A | 4/1993 | Balani |
| 5,266,582 | A | 11/1993 | De Nanteuil et al. |
| 5,290,941 | A | 3/1994 | Volante et al. |
| 5,403,816 | A | 4/1995 | Takabe et al. |
| 5,521,202 | A | 5/1996 | Yano et al. |
| 5,679,678 | A | 10/1997 | Binder et al. |
| 5,681,567 | A | 10/1997 | Martinez et al. |
| 5,760,232 | A | 6/1998 | Chen et al. |
| 5,817,678 | A | 10/1998 | Kim et al. |
| 5,840,900 | A | 11/1998 | Greenwald et al. |
| 5,880,131 | A | 3/1999 | Greenwald et al. |
| 5,932,590 | A | 8/1999 | Ciccarone et al. |
| 5,965,566 | A | 10/1999 | Greenwald et al. |
| 5,977,134 | A | 11/1999 | Ciccarone et al. |
| 5,994,353 | A | 11/1999 | Breault |
| 6,011,042 | A | 1/2000 | Greenwald et al. |
| 6,054,457 | A | 4/2000 | Setoi et al. |
| 6,057,371 | A | 5/2000 | Glennon |
| 6,103,723 | A | 8/2000 | Bergman et al. |
| 6,111,107 | A | 8/2000 | Greenwald et al. |
| 6,127,355 | A | 10/2000 | Greenwald et al. |
| 6,153,655 | A | 10/2000 | Martinez et al. |
| 6,194,580 | B1 | 2/2001 | Greenwald et al. |
| 6,214,817 | B1 | 4/2001 | Riley et al. |
| 6,232,320 | B1 | 5/2001 | Stewart et al. |

(Continued)

FOREIGN PATENT DOCUMENTS

| | | |
|---|---|---|
| CA | 2720096 | 10/2009 |
| CN | 101113148 | 1/2008 |

(Continued)

OTHER PUBLICATIONS

U.S. Appl. No. 61/581,053, filed Dec. 28, 2011, Metcalf et al.

(Continued)

*Primary Examiner* — Heidi Reese
(74) *Attorney, Agent, or Firm* — Sheppard Mullin Richter & Hampton LLP

(57) ABSTRACT

Provided herein are compounds and pharmaceutical compositions suitable as modulators of hemoglobin, methods and intermediates for their preparation, and methods for their use in treating disorders mediated by hemoglobin and disorders that would benefit from tissue and/or cellular oxygenation.

14 Claims, No Drawings

(56) References Cited

U.S. PATENT DOCUMENTS

| | | |
|---|---|---|
| 6,239,176 B1 | 5/2001 | Nudelman et al. |
| 6,242,644 B1 | 6/2001 | Ackermann et al. |
| 6,355,661 B1 | 3/2002 | Lai et al. |
| 6,395,266 B1 | 5/2002 | Martinez et al. |
| 6,472,349 B1 | 10/2002 | Hamprecht et al. |
| 6,528,529 B1 | 3/2003 | Brann et al. |
| 6,559,140 B2 | 5/2003 | Bennani et al. |
| 6,559,143 B1 | 5/2003 | Bjore et al. |
| 6,593,472 B2 | 7/2003 | Hoffman et al. |
| 6,608,076 B1 | 8/2003 | Greenwald et al. |
| 6,627,646 B2 | 9/2003 | Bakale |
| 6,630,496 B1 | 10/2003 | Seehra et al. |
| 6,638,967 B2 | 10/2003 | Bogenstaetter et al. |
| 6,670,377 B1 | 12/2003 | Mekouar et al. |
| 6,908,921 B2 | 6/2005 | Su et al. |
| 6,919,362 B2 | 7/2005 | Lesieur et al. |
| 6,953,857 B2 | 10/2005 | Nazare et al. |
| 7,005,440 B1 | 2/2006 | Jayyosi et al. |
| 7,074,809 B2 | 7/2006 | Wensbo et al. |
| 7,144,914 B2 | 12/2006 | Bjorsne et al. |
| 7,151,113 B2 | 12/2006 | Dyckman et al. |
| 7,160,910 B2 | 1/2007 | Safo et al. |
| 7,169,921 B2 | 1/2007 | Cheema et al. |
| 7,211,671 B2 | 5/2007 | Sheppeck et al. |
| 7,297,817 B2 | 11/2007 | Lesur et al. |
| 7,314,931 B2 | 1/2008 | Cladingboel |
| 7,348,044 B2 | 3/2008 | Takaku et al. |
| 7,351,434 B2 | 4/2008 | Chern et al. |
| 7,411,083 B2 | 8/2008 | Gopalsamy et al. |
| 7,582,753 B2 | 9/2009 | Abdel-Magid et al. |
| 7,615,557 B2 | 11/2009 | Bouchon et al. |
| 7,629,343 B2 | 12/2009 | Watkins et al. |
| 7,652,137 B2 | 1/2010 | Graczyk et al. |
| 7,829,590 B2 | 11/2010 | Brenchley et al. |
| 7,943,622 B2 | 5/2011 | Clark et al. |
| 8,013,153 B2 | 9/2011 | Butler et al. |
| 8,017,635 B2 | 9/2011 | Lyga et al. |
| 8,153,814 B2 | 4/2012 | Beaudoin et al. |
| 8,268,834 B2 | 9/2012 | Bruce et al. |
| 8,361,959 B2 | 1/2013 | Stamford et al. |
| 8,420,678 B2 | 4/2013 | Mahadevan et al. |
| 8,524,917 B2 | 9/2013 | Beard et al. |
| 8,557,853 B2 | 10/2013 | Chow et al. |
| 8,586,732 B2 | 11/2013 | Corkey et al. |
| 8,609,679 B2 | 12/2013 | Singh et al. |
| 8,614,242 B2 | 12/2013 | Benting et al. |
| 8,618,300 B2 | 12/2013 | Bosanac et al. |
| 8,673,970 B2 | 3/2014 | Eissenstat et al. |
| 8,703,941 B2 | 4/2014 | Romero et al. |
| 8,729,081 B2 | 5/2014 | Wu et al. |
| 8,759,520 B2 | 6/2014 | East et al. |
| 8,791,114 B2 | 7/2014 | Yu et al. |
| 8,822,462 B2 | 9/2014 | Traynelis et al. |
| 8,846,664 B2 | 9/2014 | Huang et al. |
| 8,846,694 B2 | 9/2014 | Heinrich et al. |
| 8,846,721 B2 | 9/2014 | Akella et al. |
| 8,901,133 B2 | 12/2014 | Ren et al. |
| 8,952,171 B2 | 2/2015 | Xu et al. |
| 8,969,342 B2 | 3/2015 | Hedstrom et al. |
| 8,969,349 B2 | 3/2015 | Campbell et al. |
| 8,969,363 B2 | 3/2015 | Castro et al. |
| 8,999,996 B2 | 4/2015 | Sandanayaka et al. |
| 9,012,450 B2 | 4/2015 | Metcalf et al. |
| 9,018,210 B2 | 4/2015 | Metcalf et al. |
| 9,018,380 B2 | 4/2015 | Jones et al. |
| 9,029,389 B2 | 5/2015 | No et al. |
| 9,067,948 B2 | 6/2015 | Harriman et al. |
| 9,073,946 B2 | 7/2015 | Iadonato et al. |
| 9,085,586 B2 | 7/2015 | Romero et al. |
| 9,115,120 B2 | 8/2015 | Jones et al. |
| 9,150,569 B2 | 10/2015 | Fukuda et al. |
| 9,200,005 B2 | 12/2015 | Jantos et al. |
| 9,212,190 B2 | 12/2015 | Harriman et al. |
| 9,242,933 B2 | 1/2016 | Geneste et al. |
| 9,248,199 B2 | 2/2016 | Metcalf et al. |
| 9,302,988 B2 | 4/2016 | Schunk et al. |
| 9,388,185 B2 | 7/2016 | Lu et al. |
| 9,422,279 B2 | 8/2016 | Metcalf et al. |
| 9,447,071 B2 | 9/2016 | Li et al. |
| 9,458,139 B2 | 10/2016 | Xu et al. |
| 9,504,675 B2 | 11/2016 | Boger |
| 9,505,735 B2 | 11/2016 | McLellan et al. |
| 9,512,119 B2 | 12/2016 | Nagai et al. |
| 9,527,869 B2 | 12/2016 | Biagetti et al. |
| 9,545,105 B2 | 1/2017 | Benting et al. |
| 9,604,999 B2 | 3/2017 | Harris et al. |
| 9,663,504 B2 | 5/2017 | Jones et al. |
| 9,663,718 B2 | 5/2017 | Smith et al. |
| 9,714,381 B2 | 7/2017 | Archetti et al. |
| 9,763,955 B2 | 9/2017 | Hummel et al. |
| 9,776,960 B2 | 10/2017 | Xu et al. |
| 9,802,900 B2 | 10/2017 | Li et al. |
| 9,908,898 B2 | 3/2018 | Shinde et al. |
| 9,920,073 B2 | 3/2018 | Cocklin |
| 10,017,491 B2 | 7/2018 | Metcalf et al. |
| 10,034,879 B2 | 7/2018 | Metcalf et al. |
| 10,137,118 B2 | 11/2018 | Li et al. |
| 2001/0046997 A1 | 11/2001 | Abraham et al. |
| 2002/0095035 A1 | 7/2002 | Warshawsky et al. |
| 2002/0142995 A1 | 10/2002 | Nicolau et al. |
| 2002/0147138 A1 | 10/2002 | Firestone et al. |
| 2003/0022923 A1 | 1/2003 | Lai et al. |
| 2003/0060425 A1 | 3/2003 | Ahlem et al. |
| 2003/0073712 A1 | 4/2003 | Wang et al. |
| 2003/0165714 A1 | 9/2003 | Lee et al. |
| 2003/0187026 A1 | 10/2003 | Li et al. |
| 2003/0190333 A1 | 10/2003 | Mossman et al. |
| 2003/0199511 A1 | 10/2003 | Li et al. |
| 2003/0220373 A1 | 11/2003 | Jaye et al. |
| 2004/0072796 A1 | 4/2004 | Embury et al. |
| 2004/0077654 A1 | 4/2004 | Bouillot et al. |
| 2004/0132726 A1 | 7/2004 | Arora et al. |
| 2004/0186077 A1 | 9/2004 | Diakur et al. |
| 2004/0209921 A1 | 10/2004 | Bridger et al. |
| 2005/0085484 A1 | 4/2005 | Mitchell et al. |
| 2005/0096337 A1 | 5/2005 | Ackermann et al. |
| 2005/0143420 A1 | 6/2005 | Moutouh-De Parseval et al. |
| 2005/0159605 A1 | 7/2005 | Tarur et al. |
| 2006/0094761 A1 | 5/2006 | Haque et al. |
| 2006/0205774 A1 | 9/2006 | Bamford et al. |
| 2006/0235028 A1 | 10/2006 | Li et al. |
| 2007/0197619 A1 | 8/2007 | Zelle et al. |
| 2007/0213323 A1 | 9/2007 | Imogai et al. |
| 2007/0225293 A1 | 9/2007 | Moussy et al. |
| 2007/0249628 A1 | 10/2007 | Moussy et al. |
| 2007/0281937 A1 | 12/2007 | Zelle et al. |
| 2007/0293698 A1 | 12/2007 | Quick et al. |
| 2008/0004279 A1 | 1/2008 | Moussy et al. |
| 2008/0009478 A1 | 1/2008 | Smith et al. |
| 2008/0027075 A1 | 1/2008 | Nielsen et al. |
| 2008/0108618 A1 | 5/2008 | Brann et al. |
| 2008/0114167 A1 | 5/2008 | Castro et al. |
| 2008/0146585 A1 | 6/2008 | Moussy et al. |
| 2008/0194650 A1 | 8/2008 | Chow et al. |
| 2008/0200673 A1 | 8/2008 | Cheema et al. |
| 2008/0280849 A1 | 11/2008 | Leh et al. |
| 2009/0023709 A1 | 1/2009 | Gillespie et al. |
| 2009/0143371 A1 | 6/2009 | Buettelmann |
| 2009/0163512 A1 | 6/2009 | Chen et al. |
| 2009/0306062 A1 | 12/2009 | Herold et al. |
| 2009/0312315 A1 | 12/2009 | Yamaguchi et al. |
| 2010/0022530 A1 | 1/2010 | Schiemann et al. |
| 2010/0048901 A1 | 2/2010 | Takahashi et al. |
| 2010/0204235 A1 | 8/2010 | Lizos et al. |
| 2010/0210651 A1 | 8/2010 | Hernandez et al. |
| 2010/0311748 A1 | 12/2010 | Dakin et al. |
| 2011/0294836 A1 | 12/2011 | Song et al. |
| 2012/0184572 A1 | 7/2012 | Song et al. |
| 2012/0189670 A1 | 7/2012 | Kirkpatrick et al. |
| 2012/0220569 A1 | 8/2012 | Ohashi et al. |
| 2012/0245344 A1 | 9/2012 | Endo et al. |
| 2013/0012434 A1 | 1/2013 | Wong et al. |
| 2013/0045251 A1 | 2/2013 | Cen et al. |
| 2013/0072472 A1 | 3/2013 | Gless et al. |

(56) References Cited

U.S. PATENT DOCUMENTS

| | | |
|---|---|---|
| 2013/0116231 A1 | 5/2013 | Wilson et al. |
| 2013/0178453 A1 | 7/2013 | Rohde et al. |
| 2013/0190315 A1 | 7/2013 | Metcalf et al. |
| 2013/0190316 A1 | 7/2013 | Metcalf et al. |
| 2013/0190375 A1 | 7/2013 | Dunkel et al. |
| 2013/0196960 A1 | 8/2013 | Rohde et al. |
| 2013/0273157 A1 | 10/2013 | Ishii et al. |
| 2013/0303761 A1 | 11/2013 | Odolczyk et al. |
| 2013/0337564 A1 | 12/2013 | Davis et al. |
| 2013/0338158 A1 | 12/2013 | Beard et al. |
| 2014/0004184 A1 | 1/2014 | Ashraf et al. |
| 2014/0018361 A1 | 1/2014 | Harriman et al. |
| 2014/0073634 A1 | 3/2014 | Jones et al. |
| 2014/0142149 A1 | 5/2014 | Zhang et al. |
| 2014/0271591 A1 | 9/2014 | Sinha et al. |
| 2014/0274961 A1 | 9/2014 | Metcalf et al. |
| 2014/0275152 A1 | 9/2014 | Metcalf et al. |
| 2014/0275176 A1 | 9/2014 | Xu et al. |
| 2014/0275181 A1 | 9/2014 | Harris et al. |
| 2014/0357636 A1 | 12/2014 | Rothbaum et al. |
| 2015/0057251 A1 | 2/2015 | Harris |
| 2015/0133430 A1 | 5/2015 | Xu et al. |
| 2015/0141465 A1 | 5/2015 | Yee et al. |
| 2015/0166890 A1 | 6/2015 | Archetti et al. |
| 2015/0225366 A1 | 8/2015 | Li |
| 2015/0258104 A1 | 9/2015 | Friedhoff |
| 2015/0258105 A1 | 9/2015 | Maillet et al. |
| 2015/0258106 A1 | 9/2015 | Friedhoff |
| 2015/0259296 A1 | 9/2015 | Li et al. |
| 2015/0307945 A1 | 10/2015 | Nakanishi et al. |
| 2015/0336908 A1 | 11/2015 | Shioda et al. |
| 2015/0344472 A1 | 12/2015 | Metcalf et al. |
| 2015/0344483 A1 | 12/2015 | Metcalf et al. |
| 2016/0024127 A1 | 1/2016 | Harris et al. |
| 2016/0031865 A1 | 2/2016 | Li et al. |
| 2016/0031904 A1 | 2/2016 | Li et al. |
| 2016/0038474 A1 | 2/2016 | Sinha et al. |
| 2016/0039801 A1 | 2/2016 | Metcalf et al. |
| 2016/0046613 A1 | 2/2016 | Metcalf et al. |
| 2016/0083343 A1 | 3/2016 | Xu et al. |
| 2016/0303099 A1 | 3/2016 | Dufu et al. |
| 2016/0108031 A1 | 4/2016 | Metz et al. |
| 2016/0152602 A1 | 6/2016 | Xu et al. |
| 2016/0206604 A1 | 7/2016 | Metcalf et al. |
| 2016/0206614 A1 | 7/2016 | Metcalf et al. |
| 2016/0207904 A1 | 7/2016 | Li et al. |
| 2016/0208171 A1 | 7/2016 | Kim et al. |
| 2016/0220579 A1 | 8/2016 | Weis et al. |
| 2016/0332984 A1 | 11/2016 | Metcalf et al. |
| 2016/0346263 A1 | 12/2016 | Li et al. |
| 2017/0066729 A1 | 3/2017 | Zheng et al. |
| 2017/0107199 A1 | 4/2017 | Metcalf et al. |
| 2017/0157101 A1 | 6/2017 | Ramos et al. |
| 2017/0174654 A1 | 6/2017 | Metcalf et al. |
| 2017/0233385 A1 | 8/2017 | He et al. |
| 2017/0275534 A1 | 9/2017 | Reddy et al. |
| 2017/0304321 A1 | 10/2017 | Quirk et al. |
| 2017/0327484 A1 | 11/2017 | Li et al. |
| 2017/0355713 A1 | 12/2017 | Harris et al. |
| 2018/0118730 A1 | 5/2018 | DeWitt et al. |
| 2018/0125789 A1 | 5/2018 | Dalziel et al. |
| 2018/0186807 A1 | 7/2018 | Yee et al. |
| 2018/0201577 A1 | 7/2018 | Xu et al. |
| 2018/0354929 A1 | 12/2018 | Metcalf et al. |
| 2019/0010121 A1 | 1/2019 | Xu et al. |
| 2019/0010176 A1 | 1/2019 | Harris |
| 2019/0106404 A1 | 4/2019 | Li et al. |
| 2019/0111037 A1 | 4/2019 | Li et al. |
| 2019/0112287 A1 | 4/2019 | Metcalf et al. |
| 2019/0160060 A1 | 5/2019 | Metcalf et al. |

FOREIGN PATENT DOCUMENTS

| | | |
|---|---|---|
| CN | 101143192 A | 3/2008 |
| CN | 101838264 A | 9/2010 |
| CN | 102116772 | 7/2011 |
| CN | 102206172 A | 10/2011 |
| CN | 103936658 A | 7/2014 |
| CN | 103936659 A | 7/2014 |
| CN | 104876912 A | 9/2015 |
| DE | 2238734 | 2/1973 |
| DE | 2238628 | 3/1973 |
| DE | 2853765 | 6/1980 |
| DE | 2904829 | 8/1980 |
| DE | 226590 | 8/1985 |
| DE | 3503435 | 8/1985 |
| DE | 3431004 | 3/1986 |
| DE | 3704223 | 8/1987 |
| DE | 258226 | 7/1988 |
| DE | 276479 | 2/1990 |
| DE | 276480 | 2/1990 |
| DE | 3931954 | 3/1990 |
| DE | 4318550 | 12/1994 |
| DE | 4442050 | 5/1996 |
| EP | 010063 | 4/1980 |
| EP | 0054924 | 6/1982 |
| EP | 236140 | 9/1987 |
| EP | 0268989 | 6/1988 |
| EP | 0278686 | 8/1988 |
| EP | 0291916 | 11/1988 |
| EP | 0303465 | 2/1989 |
| EP | 0336369 | 10/1989 |
| EP | 0348155 | 12/1989 |
| EP | 0365328 | 4/1990 |
| EP | 0401517 | 12/1990 |
| EP | 0453210 | 10/1991 |
| EP | 0462800 | 12/1991 |
| EP | 0481802 | 4/1992 |
| EP | 0498380 | 8/1992 |
| EP | 0528337 | 2/1993 |
| EP | 0542372 | 5/1993 |
| EP | 0567133 | 10/1993 |
| EP | 0632036 | 1/1995 |
| EP | 0637586 | 2/1995 |
| EP | 0640609 | 3/1995 |
| EP | 0747393 | 12/1996 |
| EP | 2123637 | 11/2009 |
| EP | 2149545 | 3/2010 |
| EP | 2305625 | 6/2011 |
| EP | 2883934 A1 | 6/2015 |
| EP | 2985334 A1 | 2/2016 |
| FR | 2217016 | 1/1900 |
| FR | 2761069 | 9/1998 |
| FR | 2909379 | 6/2008 |
| GB | 1409865 | 10/1975 |
| GB | 1593417 | 7/1981 |
| IL | 64573 | 4/1985 |
| IN | 29/2016 | 7/2016 |
| IT | 1380428 B1 | 9/2010 |
| JP | 57-145844 | 6/1905 |
| JP | 59029667 | 2/1984 |
| JP | 61-040236 | 2/1986 |
| JP | 63230687 | 9/1988 |
| JP | S-63258463 | 10/1988 |
| JP | 01190688 | 7/1989 |
| JP | 06-041118 | 2/1994 |
| JP | 07-025882 | 1/1995 |
| JP | 2002-523469 | 7/2002 |
| JP | 2002-528537 | 9/2002 |
| JP | 2003-075970 | 3/2003 |
| JP | 2003-513060 | 4/2003 |
| JP | 2006-306926 | 11/2006 |
| JP | 2006-342115 | 12/2006 |
| JP | 2007-291046 | 11/2007 |
| JP | 2009-108152 | 5/2009 |
| JP | 2009-149754 | 7/2009 |
| JP | 2009-203230 | 9/2009 |
| JP | 2009-242540 | 10/2009 |
| JP | 2010-059131 | 3/2010 |
| JP | 2010-066630 | 3/2010 |
| JP | 2011-006360 | 1/2011 |
| JP | 2011-162678 | 8/2011 |
| JP | 2011-207765 | 10/2011 |
| JP | 2011-246381 | 12/2011 |

(56) References Cited

FOREIGN PATENT DOCUMENTS

| | | |
|---|---|---|
| JP | 2014-005380 | 1/2014 |
| WO | WO 91/09594 | 7/1991 |
| WO | WO-91/19697 | 12/1991 |
| WO | WO-92/02503 | 2/1992 |
| WO | WO 93/00313 | 1/1993 |
| WO | WO-93/17013 | 9/1993 |
| WO | WO-94/01406 | 1/1994 |
| WO | WO-95/14015 | 5/1995 |
| WO | WO-95/21854 | 8/1995 |
| WO | WO-96/11902 | 4/1996 |
| WO | WO 96/41795 | 12/1996 |
| WO | WO 97/18813 | 5/1997 |
| WO | WO-97/41120 | 11/1997 |
| WO | WO-97/44306 | 11/1997 |
| WO | WO-98/08818 | 3/1998 |
| WO | WO-98/21199 | 5/1998 |
| WO | WO 98/45269 | 10/1998 |
| WO | WO 99/20609 | 4/1999 |
| WO | WO 99/28313 | 6/1999 |
| WO | WO 99/28314 | 6/1999 |
| WO | WO-99/29694 | 6/1999 |
| WO | WO-99/43672 | 9/1999 |
| WO | WO-99/47529 | 9/1999 |
| WO | WO-99/48490 | 9/1999 |
| WO | WO 99/050247 | 10/1999 |
| WO | WO-99/59978 | 11/1999 |
| WO | WO-99/62908 | 12/1999 |
| WO | WO-00/12121 | 3/2000 |
| WO | WO-00/26202 | 5/2000 |
| WO | WO-00/35858 | 6/2000 |
| WO | WO-00/40564 | 7/2000 |
| WO | WO-00/46203 | 8/2000 |
| WO | WO-00/63172 | 10/2000 |
| WO | WO-00/64876 | 11/2000 |
| WO | WO-00/71123 A1 | 11/2000 |
| WO | WO-00/75145 | 12/2000 |
| WO | WO-00/78746 | 12/2000 |
| WO | WO-01/00612 | 1/2001 |
| WO | WO-01/05763 | 1/2001 |
| WO | WO-01/19823 | 3/2001 |
| WO | WO-01/23383 | 4/2001 |
| WO | WO-01/28992 | 4/2001 |
| WO | WO-01/32596 | 5/2001 |
| WO | WO-01/36375 | 5/2001 |
| WO | WO-01/57002 | 8/2001 |
| WO | WO-01/57006 | 8/2001 |
| WO | WO-01/57044 | 8/2001 |
| WO | WO-01/62705 | 8/2001 |
| WO | WO-01/66098 | 9/2001 |
| WO | WO-01/66534 | 9/2001 |
| WO | WO-01/70663 | 9/2001 |
| WO | WO-02/00622 | 1/2002 |
| WO | WO-02/12224 | 2/2002 |
| WO | WO-02/12235 | 2/2002 |
| WO | WO-02/24635 | 3/2002 |
| WO | WO-02/24679 | 3/2002 |
| WO | WO-02/51831 | 7/2002 |
| WO | WO-02/051849 | 7/2002 |
| WO | WO-02/053547 | 7/2002 |
| WO | WO-02/55496 | 7/2002 |
| WO | WO 02/60902 | 8/2002 |
| WO | WO 02/83690 | 10/2002 |
| WO | WO-03/051366 | 6/2003 |
| WO | WO-03/053368 | 7/2003 |
| WO | WO 03/082288 | 10/2003 |
| WO | WO-03/101959 | 12/2003 |
| WO | WO 2004/014370 | 2/2004 |
| WO | WO-2004/014899 | 2/2004 |
| WO | WO 2004/014902 | 2/2004 |
| WO | WO-2004/018430 | 3/2004 |
| WO | WO-2004/024705 | 3/2004 |
| WO | WO 2004/035592 | 4/2004 |
| WO | WO-2004/050030 | 6/2004 |
| WO | WO 2004/054584 | 7/2004 |
| WO | WO-2004/056727 | 7/2004 |
| WO | WO-2004/058790 | 7/2004 |
| WO | WO-2004/073675 | 9/2004 |
| WO | WO 2004/078757 | 9/2004 |
| WO | WO-2004/087075 | 10/2004 |
| WO | WO 2004/089373 | 10/2004 |
| WO | WO 2004/089410 | 10/2004 |
| WO | WO 2004/098528 | 11/2004 |
| WO | WO 2004/099127 | 11/2004 |
| WO | WO-2004/111031 | 12/2004 |
| WO | WO 2005/040119 | 5/2005 |
| WO | WO 2005/042467 | 5/2005 |
| WO | WO 2005/042491 | 5/2005 |
| WO | WO-2005/047249 | 5/2005 |
| WO | WO 2005/068458 | 7/2005 |
| WO | WO-2005/074513 | 8/2005 |
| WO | WO 2005/077368 | 8/2005 |
| WO | WO 2005/077373 | 8/2005 |
| WO | WO-2005/077932 | 8/2005 |
| WO | WO 2005/086836 | 9/2005 |
| WO | WO-2005/086951 | 9/2005 |
| WO | WO 2005/087748 | 9/2005 |
| WO | WO-2005/087766 | 9/2005 |
| WO | WO-2005/096337 | 10/2005 |
| WO | WO 2005/100310 | 10/2005 |
| WO | WO 2005/102318 | 11/2005 |
| WO | WO 2005/102325 | 11/2005 |
| WO | WO 2005/102326 | 11/2005 |
| WO | WO 2005/102346 | 11/2005 |
| WO | WO 2005/102455 | 11/2005 |
| WO | WO 2005/112920 | 12/2005 |
| WO | WO 2005/115304 | 12/2005 |
| WO | WO 2005/115385 | 12/2005 |
| WO | WO-2006/011469 | 2/2006 |
| WO | WO-2006/065204 | 6/2006 |
| WO | WO-2006/088173 | 8/2006 |
| WO | WO-2006/103463 | 10/2006 |
| WO | WO-2006/106711 | 10/2006 |
| WO | WO 2006/113261 | 10/2006 |
| WO | WO-2006/116764 | 11/2006 |
| WO | WO-2006/003923 | 12/2006 |
| WO | WO 2006/129134 | 12/2006 |
| WO | WO 2006/130403 | 12/2006 |
| WO | WO 2006/137771 | 12/2006 |
| WO | WO-2007/003962 | 1/2007 |
| WO | WO-2007/009389 | 1/2007 |
| WO | WO-2007/017267 | 2/2007 |
| WO | WO 2007/035430 | 3/2007 |
| WO | WO-2007/047204 | 4/2007 |
| WO | WO-2007/049675 | 5/2007 |
| WO | WO-2007/061923 | 5/2007 |
| WO | WO 2007/081630 | 7/2007 |
| WO | WO-2007/084914 | 7/2007 |
| WO | WO 2007/095561 | 8/2007 |
| WO | WO-2007/109783 | 9/2007 |
| WO | WO-2007/117180 | 10/2007 |
| WO | WO 2007/120760 | 10/2007 |
| WO | WO 2007/141318 | 12/2007 |
| WO | WO 2007/146066 | 12/2007 |
| WO | WO-2008/012495 | 1/2008 |
| WO | WO-2008/013414 | 1/2008 |
| WO | WO-2008/016132 | 2/2008 |
| WO | WO-2008/029200 | 3/2008 |
| WO | WO-2008/041118 | 4/2008 |
| WO | WO-2008/051532 | 5/2008 |
| WO | WO-2008/060391 | 5/2008 |
| WO | WO-2008/066145 | 6/2008 |
| WO | WO 2008/080455 | 7/2008 |
| WO | WO-2008/081096 | 7/2008 |
| WO | WO 2008/089015 | 7/2008 |
| WO | WO-2008/101682 | 8/2008 |
| WO | WO-2008/116620 | 10/2008 |
| WO | WO 2008/121066 | 10/2008 |
| WO | WO 2008/145616 | 12/2008 |
| WO | WO-2009/001214 | 12/2008 |
| WO | WO-2009/011850 | 1/2009 |
| WO | WO-2009/050183 | 4/2009 |
| WO | WO 2009/088531 | 7/2009 |
| WO | WO 2009/105782 | 8/2009 |
| WO | WO 2009/106599 | 9/2009 |

(56) References Cited

FOREIGN PATENT DOCUMENTS

| | | |
|---|---|---|
| WO | WO 2009/115517 | 9/2009 |
| WO | WO-2009/125606 | 10/2009 |
| WO | WO-2009/128537 | 10/2009 |
| WO | WO 2009/129267 | 10/2009 |
| WO | WO-2009/130560 | 10/2009 |
| WO | WO-2009/136889 | 11/2009 |
| WO | WO-2009/146555 | 12/2009 |
| WO | WO 2009/158571 | 12/2009 |
| WO | WO 2010/008739 | 1/2010 |
| WO | WO 2010/027762 | 3/2010 |
| WO | WO-2010/031589 | 3/2010 |
| WO | WO 2010/039789 | 4/2010 |
| WO | WO 2010/042925 | 4/2010 |
| WO | WO 2010/048149 | 4/2010 |
| WO | WO 2010/056311 | 5/2010 |
| WO | WO-2010/056631 | 5/2010 |
| WO | WO 2010/067067 | 6/2010 |
| WO | WO 2010/073011 | 7/2010 |
| WO | WO 2010/079443 | 7/2010 |
| WO | WO 2010/088414 | 8/2010 |
| WO | WO 2010/088518 | 8/2010 |
| WO | WO 2010/108187 | 9/2010 |
| WO | WO-2010/129055 | 11/2010 |
| WO | WO 2011/032169 | 3/2011 |
| WO | WO-2011/033045 | 3/2011 |
| WO | WO-2011/088201 | 7/2011 |
| WO | WO 2011/089576 | 7/2011 |
| WO | WO 2011/100324 | 8/2011 |
| WO | WO 2011/100359 | 8/2011 |
| WO | WO 2011/119559 | 9/2011 |
| WO | WO-2011/136459 | 11/2011 |
| WO | WO 2011/150156 | 12/2011 |
| WO | WO 2012/009194 | 1/2012 |
| WO | WO-2012/020060 | 2/2012 |
| WO | WO 2012/036573 | 3/2012 |
| WO | WO 2012/052489 | 4/2012 |
| WO | WO 2012/052491 | 4/2012 |
| WO | WO 2012/064973 | 5/2012 |
| WO | WO 2012/097013 | 7/2012 |
| WO | WO 2012/106569 | 8/2012 |
| WO | WO-2012/138981 | 10/2012 |
| WO | WO-2012/141228 | 10/2012 |
| WO | WO 2012/143796 | 10/2012 |
| WO | WO 2013/006308 | 1/2013 |
| WO | WO 2013/006485 | 1/2013 |
| WO | WO 2013/012915 | 1/2013 |
| WO | WO 2013/019548 | 2/2013 |
| WO | WO-2013/052803 | 4/2013 |
| WO | WO-2013/102142 | 7/2013 |
| WO | WO-2013/102145 | 7/2013 |
| WO | WO 2013/106535 | 7/2013 |
| WO | WO 2013/192005 | 12/2013 |
| WO | WO 2013/192517 | 12/2013 |
| WO | WO 2014/011902 | 1/2014 |
| WO | WO 2014/011906 | 1/2014 |
| WO | WO 2014/011911 | 1/2014 |
| WO | WO 2014/017643 | 1/2014 |
| WO | WO 2014/026125 | 2/2014 |
| WO | WO 2014/031872 | 2/2014 |
| WO | WO 2014/031928 | 2/2014 |
| WO | WO 2014/031933 | 2/2014 |
| WO | WO 2014/031936 | 2/2014 |
| WO | WO 2014/032801 | 3/2014 |
| WO | WO 2014/051022 | 4/2014 |
| WO | WO-2014/104384 | 7/2014 |
| WO | WO 2014/113492 | 7/2014 |
| WO | WO 2014/130856 | 8/2014 |
| WO | WO 2014/140086 | 9/2014 |
| WO | WO-2014/150256 | 9/2014 |
| WO | WO-2014/150258 | 9/2014 |
| WO | WO-2014/150261 | 9/2014 |
| WO | WO-2014/150268 | 9/2014 |
| WO | WO-2014/150276 | 9/2014 |
| WO | WO-2014/150289 | 9/2014 |
| WO | WO 2014/175713 | 10/2014 |
| WO | WO 2014/177464 | 11/2014 |
| WO | WO 2014/179144 | 11/2014 |
| WO | WO 2014/194201 | 12/2014 |
| WO | WO 2014/194242 | 12/2014 |
| WO | WO 2014/194245 | 12/2014 |
| WO | WO-2015/031284 | 3/2015 |
| WO | WO-2015/031285 | 3/2015 |
| WO | WO 2015/046827 | 4/2015 |
| WO | WO 2015/051230 | 4/2015 |
| WO | WO 2015/058832 | 4/2015 |
| WO | WO-2015/120133 | 8/2015 |
| WO | WO 2015/130790 | 9/2015 |
| WO | WO 2015/131773 | 9/2015 |
| WO | WO 2015/145336 | 10/2015 |
| WO | WO 2015/193263 | 12/2015 |
| WO | WO 2016/015803 | 2/2016 |
| WO | WO 2016/043849 | 3/2016 |
| WO | WO 2016/053662 | 4/2016 |
| WO | WO 2016/057713 | 4/2016 |
| WO | WO 2016/077541 | 5/2016 |
| WO | WO 2016/086194 | 6/2016 |
| WO | WO 2016/134283 | 8/2016 |
| WO | WO 2016/149248 | 9/2016 |
| WO | WO 2016/153951 | 9/2016 |
| WO | WO-2016/160755 | 10/2016 |
| WO | WO 2017/004133 | 1/2017 |
| WO | WO 2017/004134 | 1/2017 |
| WO | WO 2017/039318 | 3/2017 |
| WO | WO 2017/040963 | 3/2017 |
| WO | WO 2017/040982 | 3/2017 |
| WO | WO-2017/096230 | 6/2017 |
| WO | WO 2017/161028 | 9/2017 |
| WO | WO 2017/184531 | 10/2017 |
| WO | WO 2017/219083 | 12/2017 |
| WO | WO 2017/223514 | 12/2017 |

OTHER PUBLICATIONS

U.S. Appl. No. 61/661,320, filed Jun. 18, 2012, Metcalf et al.
Abdulmalik et al., "Crystallographic analysis of human hemoglobin elucidates the structural basis of the potent and dual antisickling activity of pyridyl derivatives of vanillin", Acta Cryst. 2011, D67, 920-928.
Abdulmalik et al., Sickle cell disease: current therapeutic approaches, Expert Opinion Ther. Patents, 2005, vol. 15(11), pp. 1497-1506.
Abraham et al., Vanillin, a Potential Agent for the Treatment of Sickle Cell Anemia, Blood, Mar. 1991, vol. 77 (6), pp. 1334-1341.
Adhikary, P.K., et al., "A new antisickling agent: In vitro studies of its effect on S/S erythrocytes and on hemoglobin S", Experientia. 1978, vol. 34, No. 6, pp. 804-806.
Appendix A provided with Israel office action dated Aug. 11, 2016 for IL 233329.
Arya R, et al. "Tucaresol increases oxygen affinity and reduces haemolysis in subjects with sickle cell anaemia," Br. J. Haematol., 93(4):817-21 (1996).
Ashizawa et al., Polymorphism and crystallization of the pharmaceutical drugs (Iyakuhin No Takeigensho to Shoseki No Kagaku) Maruzen Planet Co., Ltd., Sep. 20, 2002, pp. 3-16 and pp. 273-278. (in Japanese with partial English translation).
Australian Examination Report dated Nov. 7, 2016 for AU 2016203755.
Babu, et al. Regioselective synthesis and structural elucidation of 1,4-disubstituted 1,2,3-triazole derivatives using 1D and 2D NMR spectral techniques. Magn. Reson. Chem., 2011; 49: 824-829. doi:10.1002/mrc.2820.
Bacsa et al., "Novel products from Baylis-Hillman reactions of salicylaldehydes", South African Journal of Chemistry (1998), 51(1), 47-54 CODEN: SAJCDG; ISSN: 0379-4350.
Ballerini et al., High pressure Diels-Alder approach to hydroxy-substituted 6a-cyano-tetrahydro-6H-benzo[c]chromen-6-ones: A route to Δ6-Cis-Cannabidiol. J.Org.Chem., 74(11):4311-4317, 2009.
Ballet et al., Novel selective human melanocortin-3 receptor ligands: Use of the 4-amino-1,2,4,5-tetrahydro-2-benzazepin-3- one (Aba) scaffold, Bioorganic & Medicinal Chemistry Letters (2007), 17(9), 2492-2498 CODEN: BMCLES; ISSN: 0960-894X.

(56) References Cited

OTHER PUBLICATIONS

Barnes, et al., "Prospects for new drugs for chronic obstructive pulmonary disease." The Lancet, 2004, 364, 985-996.

Barnes. "COPD: is there light at the end of the tunnel?" Current Opinion in Pharmacology, 2004, 4:263-272.

Baxter et al., "Reductive aminations of carbonyl compounds with borohydride and borane reducing agents", Organic Reactions (Hoboken, NJ, United States) (2002), 59, No pp. given bin/mrwhome/107610747/HOME.

Beaumont et al., Design of ester prodrugs to enhance oral absorption of poorly permeable compounds: challenges to the discovery scientist. Curr. Drug Metab. 2003, 4:461-85.

Beddell, Substituted benzaldehydes designed to increase the oxygen affinity of human haemoglobin and inhibit the sickling of sickle erythrocycles, Br. J. Pharmac., 82:397-407, 1984.

Beena et al., "Synthesis and antibacterial activity evaluation of metronidazole-triazole conjugates", Bioorganic & Medicinal Chemistry Letters, 2009, 19(5):1396-1398.

Behanna. Equity Research—Global Blood Therapeutics. Sep. 8, 2015. Retrieved from the Internet: URL:http://www.fintechsecurities.com/Websites/fintechsecurities/images/Research_Blog/Zacks/Sep2015/GBT150908.pdf.

Berge et al., "Pharmaceutical Salts", Journal of Pharmaceutical Science, 1977, 66:1-19.

Beringer et al., Remington's Pharmaceutical Sciences, Mack Pub., 21st Edition, 2005, pp. 1072-1076.

Bernstein. Crystals in Supramolecular Chemistry. ACA Transactions. 2004; 39:1-14.

Bernstein. Polymorphism in Molecular Crystals. Clarendon Press, Oxford. 2002. 115-118, 272.

Bocci, et al. Chemical Abstracts DN 152:215307, 2010. 4 pages.

Bode et al.,"Novel synthesis and x-ray crystal structure of a coumarin derivative", South African Journal of Chemistry (1992), 45(1), 25-7 CODEN: SAJCDG; ISSN:0379-4350.

Bonaventura, et al., "Molecular Controls of the Oxygenation and Redox Reactions of Hemoglobin." Antioxidants & Redox Signaling, 18(17), 2013, 2298-2313.

Bottino, et al. Study on the scope of tert-amino effect: new extensions of type 2 reactions to bridged biaryls. J. Phys. Org. Chem. 2012; 25(11):1033-1041.

Bradbury et al., "New nonpeptide angiotensin II receptor antagonists", Journal of Medicinal Chemistry, 1993, vol. 36, pp. 1245-1254.

Braga, et al. Making crystals from crystals: a green route to crystal engineering and polymorphism. Chem Commun (Camb). Aug. 7, 2005;(29):3635-45. Epub Jun. 15, 2005.

Britton et al., "Structure-activity relationships of a series of benzothlophens-derived NPY Y1 antagonists: optimization of the C-2 side chain". Bioorganic & Medicinal Chemistry Letters (1999), 9(3), 475-480 CODEN:BMCLE8;ISSN: 0960-894X.

Brown et al., "1,2-Dihydroisoquinollnes. III, Dimerization", Tetrahedron (1966), 22(8), 2437-43 CODEN: TETRAB; ISSN;0040-4020.

Caira. Crystalline Polymorphism of Organic Compounds. Topics in Current Chemistry, Springer, Berlin, DE. 1998; 198:163-208.

"Can Voxelotor Offer New Hope for Sickle Cell Disease?," Dec. 3, 2018, available at: https://www.ashclinicalnews.org/on-location/voxelotor-offers-new-hope-sickle-cell-disease/. 4 pages.

CAS Registry No. 1039841-20-7; entry dated Aug. 10, 2008.
CAS Registry No. 1096911-11-3; entry dated Jan. 28, 2009.
CAS Registry No. 1153166-41-6; entry dated Jun. 7, 2009.
CAS Registry No. 1153961-01-3; entry dated Jun. 8, 2009.
CAS Registry No. 1184809-65-1; entry dated Sep. 15, 2009.
CAS Registry No. 1303782-57-1; entry dated Jun. 1, 2011.
CAS Registry No. 1306264-96-9; entry dated Jun. 5, 2011.
CAS Registry No. 631858-40-7; entry dated Dec. 29, 2003.

Chemical Abstract Registry No. 1142191-55-6, indexed in the Registry File on STN CA Online May 4, 2009.

Cheng, et al. Vilsmeier formylation of tert-anilines: dibenzo[b,f][1,5]diazocines and quinazolinium salts via the 't-amino effect'. J. Chem. Soc., Perkin Trans 1. 1998; 1257-1262.

Cherian et al., "Structure-Activity Relationships of Antitubercular Nitroimidazoles 3. Exploration of the Linker and Lipophilic Tail of ((S)-2-Nitro-6,7-dihydro-5H-imidazo[2,1-b][1,3]oxazin-6-yl)-(4-trifluoromethoxybenzyl)amine (6-Amino PA-824).," J. Med. Chem., Aug. 2011, vol. 54(16), pp. 5639-5659.

Ciganek, "The catalyzed a-hydroxyalkylation and a-aminoalkylation of activated olefins (the Morita-Baylis-Hillman reaction)", Organic Reactions (Hoboken, NJ, United States) (1997), 51, No pp given CODEN:ORHNBA URL:http://www3.Interscience.wiley.com/cgi-bin/mnwhome/107610747/HOME.

CMU Pharmaceutical polymorphism, internet p. 1-3 (2002) printout Apr. 3, 2008.

Concise Encyclopedia Chemistry, NY: Walter de Gruyter, 1993, 872-873.

Congreve et al. Application of Fragment Screening by X-ray Crystallography to the Discovery of Aminopyridines as Inhibitors of Beta-Secretase. J. Med. Chem. 50:1124-1132 (2007).

Cos et al., "Structure-Activity Relationship and Classification of Flavonoids as Inhibitors of Xanthine Oxidase and Superoxide Scavengers," J. Nat. Prod., (1998), 61:71-76.

Database CA Chemical Abstract Service, Li et al., "Substituted-benzoheterocycle derivatives, preparation, and application for preparation of antiviral or antineoplastic drugs," XP002726578 retrieved from STN Database accession No. 2013:366779 (abstract); RN:1427163-92-5 & CN 102 952 062 A, Mar. 6, 2013, 2 pages.

Database Pubchem Compound Dec. 4, 2011 XP 003033770 (11 pages).

Database Registry, 2011, RN 1289869-72-2, 1027970-95-1, 959671-57-9.

Database Registry, 2012, RN 1390863-18-9, 1390573-58-6, 1389652-57-6, 1387166-17-7, 1318517-26-8, 1318395-05-9, 933829-46-0, 879919-21-8.

Davidovich, et al. Detection of polymorphism by powder x-ray diffraction: interference by preferred orientation. Am. Pharm. Rev. 2004; 10, 12, 14, 16, 100.

Dean. Analytical Chemistry Handbook. University of Tennesse, Knoxville. McGraw-Hill, Inc. 1995; 10.24-10.26.

Deem. "Red Blood Cells and Hemoglobin in Hypoxic Pulmonary Vasoconstriction" Advances in experimental medicine and biology, (2006) 588, 217-231.

Desai et al. Preparation of N-[ro-(4-aryl-1-piperazinyl)ethyl/propyl]-3-hydroxyphthalimidines. Indian Journal of Chemistry. 39:455-457 (2000).

Desideri et al., "Guanylhydrazones of 3-substituted 2-pyridinecarboxaldehyde and of (2-substituted 3-pyridinyloxy) acetaldehyde as prostanoid biosynthesis and platelet aggregation inhibitors", European Journal of Medicinal Chemistry, Editions Scientifique Elsevier, Paris, FR, 1991, vol. 26, No. 4, pp. 455-460.

Di Stilo, et al. New 1,4-dihydropyridines conjugated to furoxanyl moieties, endowed with both nitric oxide-like and calcium channel antagonist vasodilator activities. J. Med. Chem. 41:5393-5401 (1998).

Ding et al., "Crystal structure of bis[µ2-2-(2-formylphenoxy)acetato-O,O]-bis[µ2-2-2-formylphynoxy)acetato-O,O]- octakis(n-butyl)tetratin(IV), Sn4O2(C9H7O4)4(C4H9)8", Zeitschrift fuer Kristallographie—New Crystal Structures (2011), 226(1), 31-32 CODEN:ZKNSFT; ISSN: 1433-7266.

Doelker, English translation of S.T.P, Pratiques (1999), 9(5), 399-409.

Doelker. English translation of Ann. Pharm. Fr., 2002, 60: 161-176.

Einfalt, et al. Methods of amorphization and investigation of the amorphous state. Acta Pharm. 2013; 63:305-334.

Elwahy, "Synthesis of new benzo-substituted macrocyclic containing quinoxaline subunits" Tetrahedron (2000), 56(6), 897-907 CODEN:TETRAB; ISSN:0040-4020.

Epsztajn et al., "Application of organolithium", Tetrahedron, Elsevier Science Publishers, Amsterdam, NL, 1991, vol. 47, No. 9, pp. 1697-1706.

European Search Report and Search Opinion dated Aug. 4, 2015 for EP Application No. 12862525.8. 9 pages.

(56) References Cited

OTHER PUBLICATIONS

European Search Report and Search Opinion dated Jul. 21, 2016 for EP Application No. 14769616.5. 8 pages.
European Search Report and Search Opinion dated May 28, 2015 for EP Application No. 12862096.0. 13 pages.
European Search Report and Search Opinion dated Nov. 16, 2016 for EP Application No. 16194019.2. 13 pages.
European Search Report and Search Opinion dated Sep. 26, 2016 for EP Application No. 14768759.4. 6 pages.
Experimental Chemistry (vol. 2)(Jikken Kagaku Koza, Zoku), Separation and refining, Maruzen Co.Ltd. Jan. 25, 1967, pp. 159-178 and pp. 186-187. (in Japanese with partial English translation).
Extended European Search Report and opinion dated Jul. 20, 2016 for EP Application No. 14768414.6. 10 pages.
Extended European Search Report and Search Opinion dated Jul. 18, 2016 for EP Application No. 14770695.6. 13 pages.
Extended European Search Report and Search Opinion dated Jul. 7, 2016 for EP Application No. 14768317.1. 7 pages.
Extended European Search Report and Search Opinion dated May 17, 2017 for EP Application No. 15746995.8. 8 pages.
Extended European Search Report and Search Opinion dated Nov. 23, 2015 for EP Application No. 12862525.8. 16 pages.
Gadaginamath, et al., "Synthesis and antibacterial activity of novel 1-butyl-2-phenoxyl2-phenylthlol2-aminomethyl-5-methoxyindole derivatives", Polish Journal of Chemistry (1997), 71(7), 923-928 CODEN: PJCHDQ; ISSN:0137-5083.
Gao et al, "A novel one-pot three-step synthesis of 2-(1-benzofuran-2-yl)quinoline-3-carboxylic acid derivatives", Journal of the Brazilian Chemical Society (2010), 21(5). 806-812 CODEN:JOCSET; ISSN: 0103-5053.
GBT Announces Positive Top-line Data from Part A of the Phase 3 HOPE Study of Voxelotor in Sickle Cell Disease, Press Release dated Jun. 27, 2018. Available at http://ir.gbt.com/phoenix.zhtml?c=254105&p=irol-newsArticle&ID-2356168.
Ghate et al., "Synthesis of vanillin ethers from 4-(bromomethyl) coumarins as anti-inflammatory agents, "European Journal of Medicinal Chemistry (2003), 38(3), 297-302 CODEN: EJMCA5; ISSN: 0223-5234.
Gibson et al., "Novel small molecule bradykinin B2 receptor antagonists", Journal of Medicinal Chemistry, 2009, vol. 52, pp. 4370-4379.
Glasson et al. Metal Template Synthesis of a Tripodal Tris(bipyridyl) Receptor that Encapsulates a Proton and an Iron (II) Centre in a Pseudo Cage. Aust. J. Chem. 65:1371-1376 (2012).
Grashey, "The nitro group as a 1,3-dipole in cycloadditions" Angewandte Chemie (1962), 74, 155 CODEN: ANCEAD; ISSN: 0044-8249.
Gu, et al. Grouping solvents by statistical analysis of solvent property parameters: implication to polymorph screening. Int J Pharm. Sep. 28, 2004;283(1-2)117-25.
Guillaumel, et al. Synthetic routes to 2-(2-benzofuranyl)benzoic acids and their cyclization into benz[6]indeno[2,1-d]furan-10-ones. Journal of Heterocyclic Chemistry, 1990; 27: 1047-1051. doi:10.1002/jhet.5570270444.
Guillory (in Brittain ed.) Polymorphism in Pharmaceutical Solids. NY, Marcel Dekker, Inc. 1999; 1-2:183-226.
Gunter et al., "Structural control of co-receptor binding in porphyrin-bipyridinium supramolecular assemblies", Journal of the Chemical Society, Perkin Transactions 1: Organic and Bio-Organic Chemistry (1998), (12), 1945-1958 CODEN: JCPRB4; ISSN: 0300-922X.
Hang, Song. "Pharmaceutical Separation Engineering" East China University of Technology Press. Aug. 31, 2011; 270-272. (in Chinese with English abstract).
Hanmantgad et al., "Synthesis and pharmacological properties of some r-(2-benzo[b]furanyl)coumarins" Indian Journal of Chemistry, Section B: Organic Chemistry Including Medicinal Chemistry (1986), 25B(7), 779-81 CODEN: IJSBDB; ISSN: 0376-4699.
He et al., "Prodrugs of Phosphonates, Phosphinates, and Phosphates", Prodrugs: Challenges and rewards Part 2, edited by Stella et al., 2007, pp. 223-264.
Heimbach et al., "Enzyme-mediated precipitation of patent drugs from their phosphate prodrugs", International Journal of Pharmaceutics, 261, p. 81-92, 2003.
Heimbach et al., "Prodrugs: Challenges and Rewards Part I," New York, NY, Singer:AAPS Press, (2007), 5(Chapter 2.2.1):157-215 Overcoming Poor Aqueous Solubility of Drugs for Oral Delivery.
Heimgartner et al., "Stereoselective synthesis of swainsonines from pyridines", Tetrahedron, Elsevier Science Publishers, Amsterdam, NL, 2005, vol. 61, No. 3, pp. 643-655.
Hoffman, et al. 3-Hydroxy-3-methyglutaryl-coenzyme A Reductase Inhibitors, 2. Structural Modification of 7-(Substituted aryl)-3,5-dihydroxy-6-heptenoic Acids and Their Lactone Derivatives. Journal of Medical Chemistry. 29(2):159-169 (1986).
Hong et al., "Potential Anticancer Agents VI: 5-Substituted Pyrimidine-6-Carboxaldehydes", Journal of Pharmaceutical Sciences, American Pharmaceutical Association, Washington, US, 1970, vol. 59, No. 11, pp. 1637-1645.
Huckauf, et al., "Oxygen Affinity of Haemoglobin and Red Cell Acid-Base Status in Patients with Severe Chronic Obstructive Lung Disease" Bull. Europe Physiopath. Resp., 1976, 12, 129-142.
International Preliminary Report on Patentability dated Jun. 5, 2018 for PCT/US2016/064723. (10 pages).
International Preliminary Report on Patentability for PCT/US2014/022846 dated Sep. 15, 2015. 7 pages.
International Preliminary Report on Patentability for PCT/US2014/022742 dated Sep. 15, 2015. 7 pages.
International Preliminary Report on Patentability for PCT/US2014/022733 dated Sep. 15, 2015. 11 pages.
International Preliminary Report on Patentability for PCT/US2014/022769 dated Sep. 15, 2015. 8 pages.
International Search Report and Written Opinion dated Aug. 19, 2014 for PCT Application No. PCT/US2014/022736. 14 pages.
International Search Report and Written Opinion dated Aug. 27, 2014 for PCT Application No. PCT/US2014/022742. 11 pages.
International Search Report and Written Opinion dated Aug. 4, 2017 for PCT Application No. PCT/US2017/032104. 10 pages.
International Search Report and Written Opinion dated Dec. 8, 2014 for PCT Application No. PCT/US2014/052575. 10 pages.
International Search Report and Written Opinion dated Jan. 22, 2018 for PCT Application No. PCT/US2017/056352. 12 pages.
International Search Report and Written Opinion dated Jul. 22, 2014 for PCT Application No. PCT/US2014/022846. 11 pages.
International Search Report and Written Opinion dated Jul. 30, 2014 for PCT Application No. PCT/US2014/029682. 16 pages.
International Search Report and Written Opinion dated Jul. 31, 2014 for PCT Application No. PCT/US2014/022789. 13 pages.
International Search Report and Written Opinion dated Jul. 4, 2014 for PCT Application No. PCT/US2014/022769. 11 pages.
International Search Report and Written Opinion dated Mar. 5, 2013 for PCT Application No. PCT/US2012/072177. 7 pages.
International Search Report and Written Opinion dated May 3, 2017 for PCT Application No. PCT/US2016/064723. 15 pages.
International Search Report and Written Opinion dated May 11, 2015 for PCT Application No. PCT/US2015/014589. 5 pages.
International Search Report and Written Opinion dated May 20, 2013 for PCT Application No. PCT/US2012/072183. 11 pages.
International Search Report and Written Opinion dated Nov. 28, 2014 for PCT Application No. PCT/US2014/052576. 11 pages.
International Search Report and Written Opinion dated Oct. 31, 2014 for PCT Application No. PCT/US2014/013575. 10 pages.
Israel office action dated Aug. 11, 2016 for Israeli Patent Application No. 233329.
Ito et al., A medium-term rat liver bioassay for rapid in vivo detection of carcinogenic potential of chemicals,01 D Cancer Science, Jan. 2003, 94, pp. 3-8.
Ivanisevic, et al. Uses of x-ray powder diffraction in the pharmaceutical industry. Pharm. Sci. Encycl. 2010; 1-42.
Jain, et al., "Polymorphism in Pharmacy", Indian Drugs, 1986, 23(6) 315-329.
Jarvest et al., "Discovery and optimisation of potent, selective, ethanolamine Inhibitors of bacterial phenylalanyl tRNA synthetase", Bioorganic & Medicinal Chemistry Letter (2005), 15(9), 2305-2309 CODEN: BMCLES; ISSN: 0960-894X.

(56) References Cited

OTHER PUBLICATIONS

Karche et al., "Electronic Effects in Migratory Groups [1,4]- versus [1,2]-Rearrangement in Rhodium Carbenoid Generated Bicyclic Oxonium Ylides", Journal of Organic Chemistry (2001), 66(19), 63236332 CODEN: JOCEAH; ISSN: 0022-3263.
Katritzky et al., "Syntheses of 3-hydroxymethyl-2-3-dihydrobenzofurans and 3-hydroxymethylbenzofurans", ARKIVOC (Gainesville, FL, United States) (2003), (6), 49-61 CODEN: AGFUAR URL: http://www.arkat-usa.org/ark/journal/2003/Vargoglis/AV-622A/6ss.pdf.
Kaye et al., "DABCO-catalyzed reactions of salicylaldehydes with acrylate derivatives", Synthetic Communications (1996), 26(11), 2085-97 CODEN: SYNCAV; ISSN: 0039-7911.
Kaye et al., "Does the DABCO-catalyzed reaction of 2-hydroxybenzaldehydes with methyl acrylate follow a Baylis-Hillman pathway?", Organic & Biomolecular Chemistry (2003), 1(7), 1133-1138 CODEN: OBCRAK; ISSN: 1477-0520.
Keidan, et al. Effect of BW12C on oxygen affinity of hemoglobin in sickle-cell disease. The Lancet. 1986; 327(8485):831-834.
Kessar et al., "Synthesis of Isoindolobenzazepines via photocyclisation of N-(2-formylphenethyl)phthalimide derivatives", Indian Journal of Chemistry, Section B: Organic Chemistry Including Medicinal Chemistry (1991), 30B(11), 999-1005 CODEN: JSBDB; ISSN:3076-4699.
Kessar et al., An Interesting Application of Photocyclisation in Apophdeadane Alkaloid Synthesis. Tetrahedron Letters (1987), 28(44), 5323-5326. CODEN: TELEAY; ISSN: 0040-4039.
Kirk-Othmer Encyclopedia of Chemical Technology. 2002; 8:95-147.
Kise et al., "Electroreductive Intramolecular Coupling of Phthalimides with Aromatic Aldehydes: Application to the Synthesis of Lennoxamine". Journal of Organic Chemistry (2011), 76(23), 9856-9880 CODEN:JOCEAH; ISSN: 0022-3263.
Klis, et al. Halogen-lithium exchange versus deprotonation: synthesis of diboronic acids derived from aryl-benzyl ethers. Tetrahedron Letters, 48(7):1169-1173 (2007).
Kratochvil. Chapter 8 Solid Forms of Pharmaceutical Molecules. J. Sestak et al. (eds.), Glassy, Amorphous and Nano-Crystalline Materials. Hot Topics in Thermal Analysis and Calorimetry 8, 2011, pp. 129-140.
Krow, "The Baeyer-Villiger oxidation of ketones and aldehydes", Organic Reactions (Hoboken, NJ, United States) (1993), 43, No pp. given CODEN: ORHNBA URL: http://www3.interscience.wiley.com/cgi-bin/mrwhome/107610747/HOME.
Kucera, et al. Evaluation of Ceolus(TM) microcrystalline cellulose grades for the direct compression of enteric-coated pellets. Drug Development and Industrial Pharmacy. Mar. 1, 2012; 38(3):341-350.
Lakkannavar et al., "4-[2'-benzylideneanlino aryloxymethyl] coumarins E and Z isomers". Indian Journal of Heterocyclic Chemistry (1995), 4(4), 303-4 CODEN: IJCHEI; ISSN: 0971-1627.
Lehrer, et al. GBT440, a novel anti-polymerization agent, for the treatment of sickle cell disease. Global Blood Therapeutics. Apr. 1, 2016. (50 pages) Retrieved from the Internet: http://casicklecell.org/img/PresentationSlidesWebinar3.pdf.
Lin et al. Synthesis and anticancer activity of benzyloxybenzaldehyde derivatives against HL-60 cells. Bioorganic & Medicinal Chemistry. 13(5), 1537-1544 (2005).
Lin et al., "Potential Antitumor Agents.8. Derivatives of 3- and 5-Benzyloxy-2-formylpyridine Thiosemicarbazone", Journal of Medicinal Chemistry, American Chemical Society, US, 1972, vol. 15, No. 6, pp. 615-618.
Liu et al., "Synthesis of Double-Armed Benzo- 15-crown-5 and Their Complexation Thermodynamics with Alkali Cations", Journal of Inclusion Phenomena and Macrocyclic Chemistry (2005), 52(3-4), 229235 CODEN: JIPCF5; ISSN: 1388-3127.
Luan, et al. TOPS-MODE model of multiplexing neuroprotective effects of drugs and experimental-theoretic study of new 1,3-rasagiline derivatives potentially useful in neurodegenerative diseases. Bioorganic & Medicinal Chemistry. 2013; 21:1870-1879.

Mahoney et al., "Functionalization of Csp3-H bond-Sc(OTf)3-catalyzed domino 1,5-hydride shift/cyclization/Friedel-Crafts acylation reaction of benzylidene Meldrum's acids", Tetrahedron Letters (2009), 50(33), 4706-4709 CODEN: TELEAY; ISSN: 0040-4039.
Majhi et al., "An efficient synthesis of novel dibenzo-fused nine-membered oxacycles using a sequential Baylis-Hillman reaction and radical cyclization", Synthesis (2008), (1), 94-100 CODEN: SYNTBF; ISSN: 0039-7881.
Manna et al., Synthesis and beta-adrenoreceptor blocking activity of [[3-(alkylamine)-2-hydroxypropyl]oximino]pyridines and 0[3-(alkylamine)-2-hydroxypropyl]methylpyridine ketone oximes derivatives, IL FARMACO, 1996, vol. 51, No. 8, 9, pp. 579-587.
Mantyla et al., Synthesis, in vitro evaluation, and antileishmanial activity of water-soluble prodrugs of buparvaquone. J. Med. Chem. 2004, 47:188-195.
Marchetti et al., "Synthesis and biological evaluation of 5-substituted O4-alkylpyrimidines as CDK2 inhibitors," Org. Biomol. Chem, 2010, vol. 8, pp. 2397-2407.
"Master of Engineering Education Chemical Engineering Development Report" National Engineering Education Master in Chemical Engineering Cooperation Group, Zhejiang University Press. Mar. 31, 2011; 241-245. (in Chinese with English abstract).
Mathur. "Microcrystalline Cellulose" In: "Handbook of Pharmaceutical Excipients, Second Edition", Jan. 1, 1994, The Pharmaceutical Press, London, pp. 84-87.
McKay et al., 7,11,15,28—Tetrakis[(2-formylphenoxy)methyl]-1,21,23,25- tetramethylresorcin[4]arene cavitand ethyl acetate clathrate at 173 K, Acta Crystallographica, Section E: Structure Reports Online (2009), E65(4), 692-693 CODEN: ACSEBH; ISSN: 1600-5368 URL: http://journals.iucr.org/e/issues/2009/04/00/fl22 33/fl2233.pdf.
McKay et al., "Microwave-assisted synthesis of a new series of resorcin[4]arene cavitand-capped porphyrin capsules", Organic & Biomolecular Chemistry (2009), 7(19), 3958-3968 CODEN: OBCRAK; ISSN: 1477-0520.
Merlino et al., "Development of second generation amidinohydrazones, thio- and semicarbazones as Trypanosoma cruzi-inhibitors bearing benzofuroxan and benzimidazole 1,3-dioxide core scaffolds", MedChemComm (2010), 1(3), 216-228 CODEN: MCCEAY; ISSN: 2040-2503.
Mesguiche et al.,"4-Alkoxy-2,6-diaminopyrimidine Derivatives: Inhibitors of Cyclin Dependent Kinases 1 and 2," Bioorganic & Medicinal Chemistry Letters, Jan. 2003, vol. 13, pp. 217-222.
Metcalf, et al., "Discovery of GBT440, an Orally Bioavailable R-State Stabilizer of Sickle Cell Hemoglobin," ACS Med. Chem. Lett., 2017, 8, 321-326.
Mitra et al., "Synthesis and biological evaluation of dibenz[b,f][1,5]oxazocine derivatives for agonist activity at x-opioid receptor", European Journal of Medicinal Chemistry (2011), 46(5), 1713-1720 CODEN: EJMCA5; ISSN: 0223-5234.
Mulwad et al., "Synthesis and antimicrobial activity of [6'-methyl-4'-methoxy-2-oxo-2H-[1]-benzopyran)-2",4" dihydro-[1",2",4"}-triazol-3' -one and 3'phenylthiazolidin-4' -one-phenoxymethyl derivatives of dipyranoquinoline", Pharmaceutical Chemistry Journal Ahead of Print CODEN: PCJOAU; ISSN: 0091-150, 2011; pp. 427-432.
Muzaffar, et al., "Polymorphism and Drug Availability: a Review" J of Pharm. (Lahore), 1979, 1(1), 59-66.
Nagy et al., Selective coupling of methotrexate to peptide hormone carriers through a y-carboxamide linkage of its glutamic acid moiety: Benzotriazol-1-yloxytris(dimethylamino)phosphonium hexafluorophosphate activation in salt coupling. Proc. Natl. Acad. Sci. USA 1993, 90:6373-6376.
Neelima et al., "A novel annelation reaction: synthesis of 6H-[1]benzopyrano[4,3-b]quinolines "Chemistry & Industry (London, United Kingdom) (1986), (4), 141-2 CODEN: CHINAG; ISSN: 0009-3068.
New Introduction of Pharmacology (Sin Yakuzaigaku Soron)(revised 3rd Edition),Apr. 10, 1987, Nankodo Co., Ltd p. 111. (in Japanese with partial English translation).
New Pharmaceutical Preparation (Shin Seizaigaku), Nanzando Co.,Ltd., Apr. 25, 1984, p. 102-103 and pp. 232-233. (in Japanese with partial English translation).

(56) References Cited

OTHER PUBLICATIONS

Nnamani, et al., "Pyridyl derivatives of benzaldehyde as potential antisickling agents," Chem. Biodivers., (2008), 5(9):1762-1769.
Nogrady, Medicinal Chemistry A Biochemical Approach, Oxford University Press, New York, pp. 388-393 (1985).
Nonoyama et al.,"Cyclometallation of 2-(2-pyridyl)benzo[b]furen and 1-(2-pyridyl and 2-pyrimidyl)indole with palladium(II) and rhodium(III). Structures of unexpectedly formed nitro palladium(II) complexes", Polyhedron 1999, 533-543 CODEN: PLYHDE; ISSN: 0277-5387.
Notice of Allowance dated Dec. 19, 2014 for U.S. Appl. No. 13/730,730. 11 pages.
Nyerges et al, "Synthesis of Indazole N-oxides via the 1,7-electrocyclization of azomethine ylides", Tetrahedron Letters (2001), 42(30), 5081-5083 CODEN: TELEAY; ISSN:0040-4039.
Nyerges et al, "Synthesis of Indazole N-oxides via the 1,7-electrocyclization of azomethine ylides", Tetrahedron Letters (2004), 60(44), 9937-9944 CODEN: TETRAB; ISSN:0040-4020.
OECD SIDS "SIDS Initial Assessment Report for 13th SIAM," Nov. 2001, pp. 1-95.
Office Action dated Aug. 29, 2014 for U.S. Appl. No. 13/730,730. 17 pages.
Office Action dated Dec. 3, 2013 for U.S. Appl. No. 13/730,674. 8 pages.
Office Action dated Jul. 6, 2015 for U.S. Appl. No. 13/815,874. 14 pages.
Office Action dated Jun. 12, 2015 for CN Application No. 201280070743.5. 13 pages.
Office Action dated Jun. 29, 2015 for U.S. Appl. No. 13/815,810. 19 pages.
Office Action dated Jun. 30, 2014 for U.S. Appl. No. 13/730,674. 9 pages.
Office Action dated Sep. 18, 2013 for U.S. Appl. No. 13/730,674. 10 pages.
Oh, et al. Solid-phase synthesis of 1,3-oxazolidine derivatives. Tetrahedron Letters. 2000; 41:5069-5072.
O'Reilly, "Metal-phenoxyalkanoic acid interactions, XXV. The crystal structures of (2-formyl-6-methoxyphenoxy)acetic acid and its zinc(II)complex and the lithium, zinc(II) and cadmium(II) complexes of (2-chlorophenoxy)acetic acid", Australian Journal of Chemistry (1987), 40(7)m 1146-59 CODEN; AJCHAS; ISSN:0004-9425.
Otsuka, et al., "Effect of Polymorphic Forms of Bulk Powders on Pharmaceutical Properties of Carbamazepine Granules." Chem. Pharm. Bull., 47(6) 852-856 (1999).
Patani, et al. Bioisosterism: A Rational Approach in Drug Design. J. Chem Rev. 1996, 96(8), pp. 3147-3176.
Paul, et al. Hydroxyl directed C-arylation: synthesis of 3-hydroxyflavones and 2-phenyl-3-hydroxy pyran-4-ones under transition-metal free conditions. Org. Biomol. Chem., 2018, 16:444-451.
Perez et al., "Preparation of new 1,2-disubstituted ferrocenyl ammonium salt", Polyhedron (2009), 28(14), 3115-3119 CODEN: PLYHE; ISSN:0277-5387.
Perkins et al., "Manganese(II), Iron(II), cobalt(II), and cooper(II)complexes of an extended inherently chiral tris-bipyridyl cage", Proceedings of the National Academy of Sciences of the United States of America (2006), 103(3), 532-537 CODEN: PNASA6; ISSN: 0027-8424.
Pharmacy-Foundation and Application-(Chozaigaku, Kiso to Ouyou), Nanzando Co.,Ltd., Sep. 20, 1977 p. 142-145. (in Japanese with partial English translation).
Potapov, et al. A convenient synthesis of heterocyclic compounds containing 11-oxo-6,11,12,13-tetrahydrodibenzo[b,g][1,5]oxazonine fragment. Mendeleev Communications. 2009; 19:287-289.
Prohens, et al. Polymorphism in pharmaceutical industry. The Pharmacist. Apr. 1, 2007; 373:58-68. (in Spanish with English abstract).
Pubchem CID 54009805 Create Date: Dec. 4, 2011 p. 1.
Pubchem CID 54883281 Create Date: Aug. 19, 2012 p. 1.

Reagan-Shaw, et al. Dose translation from animal to human studies revisited. The FASEB Journal. Mar. 2007; 22:659-661.
Remington's Pharmaceutical Sciences, 17th Edition, A. Gennaro editor, Easton Pennsylvania. Table of Contents. (1985).
Rodriguez-Spong, et al. General principles of pharmaceutical solid polymorphism: a supramolecular perspective. Adv Drug Deliv Rev. Feb. 23, 2004;56(3):241-74.
Rolan et al., "The pharmacokinetics, tolerability and pharmacodynamics of tucaresol (589C80); 4[2-formyl-3-hydroxyphenoxymethyl] benzoic acid), a potential anti-sickling agent, following oral administration to healthy subjects", British Journal of Clinical Pharmacology, 1993, 35(4):419-425.
Rooseboom et al., Enzyme-catalyzed activation of anticancer prodrugs. Pharmacol. Rev. 2004, 56:53-102.
Ruchirawat et al., "A novel synthesis of aporhoeadanes", Tetrahedron Letters (1984), 25(32), 3485-8 CODEN: TELEAY; ISSN: 0040-4039.
Safo, et al. Structural basis for the potent antisickling effect of a novel class of five-membered heterocyclic aldehydic compounds. J Med Chem. Sep. 9, 2004;47(19):4665-76.
Sahakitpichan et al., "A practical and highly efficient synthesis of lennoxamine and related isoindoloenzazepines" Tetrahedron (2004), 60(19), 4169-4172 CODEN: TETRAB; ISSN: 0040-4020.
Sahm et al., "Synthesis of 2-arylbenzofurans" Justus Liebigs Annalen der Chemie (1974), (4), 523-38 CODEN: JLACBF; ISSN: 0075-4617.
Sainsbury et al., "1,2-Dihydroisoquinolines, IV. Acylation" Tetrahedron (1966), 22(8), 2445-52 CODEN: TETRAB; ISSN: 0040-4020.
Sarodnick et al., "Quinoxalines XV, Convenient Synthesis and Structural Study of Pyrazolo[1,5-a]quinoxalines", Journal of Organic Chemistry (2009), 74(3), 1282-1287 CODEN: JOCEAH; ISSN: 0022-3263.
Schudel, et al. Uber die Chemie des Vitamins E. Helvetica Chimica Acta. 1963; 66:636-649.
Seddon. Pseudopolymorph: A Polemic. The Quill Centre, The Queen's University of Belfast, United Kingdom. Jul. 26, 2004. 2 pages.
Shetty et al. Palladium catalyzed alpha-arylation of methyl isobutyrate and isobutyronitrile: an efficient synthesis of 2,5-disubstituted benzyl alcohol and amine intermediates. Tetrahedron Letters, 47:8021-8024 (2006).
Shin, et al. Interpretation of Animal Dose and Human Equivalent Dose for Drug Development. The Journal of Korean Oriental Medicine. 2010; 31(3):1-7.
Siddiqui et al., "The Presence of Substitutents on the Aryl Moiety of the Aryl Phosphoramidate Derivative of d4T Enhances Anti-HIV Efficacy in Cell Culture-Activity Relationship," J. Med. Chem., (1999), 42:393-399.
Silva et al., "Advances in prodrug design," Mini Rev. Med. Chem., (2005), 5(10):893-914.
Singh et al., "Reductive-Cyclization-Mediated Synthesis of Fused Polycyclic Quinolines from Baylis-Hillman Adducts of Acrylonitrile: Scope and Limitations", European Journal of Organic Chemistry (2009), (20), 3454-3466 CODEN: EJOCFK; ISSN:1434-193X.
Singhal, et al., "Drug Polymorphism and Dosage Form Design: a Practical Perspective" Advanced Drug Delivery reviews 56, p. 335-347 (2004).
Sobolev et al., Effect of acyl chain length and branching on the enantioselectivity of Candida rugosa lipase in the kinetic resolution of 4-(2-difluoromethoxyphenyl)-substituted 1,4-dihydropyridine 3,5-diesters. J. Org. Chem. 2002, 67:401-410.
Srivastava et al., "Synthesis and biological evaluation of 4-substituted tetrazolo[4,5-a]quinolines and 2,3-disubstituted quinoline derivatives", Indian Journal of Chemistry, Section B: Organic Chemistry Including Medicinal Chemistry (1989), 28B(7), 562-73 CODEN: IJSBOB; ISSN:0376-4699.
Starke et al., "Quinoxalines, Part 13: Synthesis and mass spectrometric study of aryloxymethylquinoxalines and benzo[b]furylquinoxalines" Tetrahedron (2004), 60(29), 6063-6078 CODEN: TETRAB; ISSN:0040-4020.

(56) References Cited

OTHER PUBLICATIONS

Stetinova, et al. Synthesis and Properties of 4-Alkylaminomethyl and 4-Alkoxymethyl Derivatives of 5-Methyl-2-Furancarboxylic Acid. Collection Czechosloval Chem. Commun. 1985; 51:2186-2192.
STN Registry Database Entry: CAS RN 1039927-57-5 (Entered STN: Aug. 20, 2008).
STN Registry Database Entry: CAS RN 1243541-58-3 (Entered STN: Sep. 29, 2010).
Strickley. Solubilizing excipients in oral and injectable formulations. Pharm Res. Feb. 2004;21(2):201-30.
Swann et al., "Rates of reductive elimination of substituted nitrophenols from the (indol-3-yl)methyl position of indolequinones", Journal of the Chemical Society, Perkin Transactions 2 (2001), (8), 1340-1345.
Table of Compounds, each of which can be found either in Table 1 of U.S. Pat. No. 9,018,210 issued Apr. 28, 2015 or Table 1 of U.S. Pat. No. 9,012,450 issued Apr. 21, 2015.
Taday, et al., "Using Terahertz Pulse Spectroscopy to Study the Crystalline Structure of a Drug: A Case Study of the Polymorphs of Ranitidine Hydrochloride." J of Pharm. Sci., 92(4), 2003, 831-838.
Testa et al., Hydrolysis in Drug and Prodrug Metabolism, Jun. 2003, Wiley-VCH, Zurich, 419-534.
The Pharmacopoeia of Japan the Sixteen edition, 2011 pp. 64-68 2.58 X-ray powder diffraction measuring method p. 2070 (in Japanese with partial English translation).
Tome et al., "Product class 13: 1,2,3-triazoles", Science of Synthesis (2004), 13, 415-601 CODEN: SSCYJ9.
Tsuge, et al. Suppressive Effect of Vitamin B6-Sugar Derivatives on the Proliferation of Feline Mammary Tumor Cell, FRM. Vitamins (Japan), 2006; 80(11):537-542. (in Japanese with English Abstract).
U.S. Pharmacopia #23, National Formulary #18, 1995, 1843-1844.
Van Halbeek, et al., "Sialic Acid in Permethylation Analysis: Prepared and Identification of Partially O-Methylated Derivatives of methyl N-Acetyl-N-Methyl-beta-D-Neurominate Methyl Glycoside", Carbohydrate Research, vol. 60, No. 1, 1978, pp. 51-62, 53, and 59.
VanRompaey et al., "A versatile synthesis of 2-substituted 4-amino-1,2,4,5-tetrahydro-2-benzepine-3-ones", Tetrahedron (2003), 59(24), 4421-4432 CODEN: TETRAB; ISSN:0040-4020.
VanRompaey et al., "Synthesis and evaluation of the 3B2-turn properties of 4-amino-1,2,4,5-tetrahydro-2-benzazepin-3-ones and of their spirocyclic derivative", European Journal of Organic Chemistry (2006), (13), 2899-2911 CODEN: EJOCFK; ISSN: 1434-193X.
Vicente et al., "Carbopalladation of Maleate and Fumarate Esters and 1,1-Dimethylallene with Ortho-Substituted Aryl Palladium Complexes" Organometallics (2010), 29(2), 409-416.
Vichinsky. "Emerging 'A' therapies in hemoglobinopathies: agonists, antagonists, antioxidants, and arginine." Hematology 2012, 271-275.
Vippagunta, et al. Crystalline Solids. Advanced Drug Delivery Reviews. 2001; 48:3-26.
Wang et al., "Studies of Benzothiophene Template as Potent Factor IXa (FIXa) Inhibitors in Thrombosis", Journal of Medicinal Chemistry (2010), 53, 1465-1472.
Warshawsky et al., "The synthesis of aminobenzazespinones as anti-phenylalanine dipeptide mimics and their use in NEP inhibition", Bioorganic & Medicinal Chemistry Letter (1996), 6(8), 957-962 CODEN: BMCLE8; ISSN: 0960-894X.
Wendt et al., "Synthesis and SAR of 2-aryl pyrido[2,3-d]pyrimidines as potent mGlu5 receptor antagonists", Bioorganic & Medicinal Chemistry Letters, Pergamon, Amsterdam, NL, vol. 17, No. 19, Sep. 14, 2007 (Sep. 14, 2007), pp. 5396-5399.
Wermuth, Camille G., "Molecular Variations Based on Isosteric Replacements", The Practice of Medicinal Chemistry, 1996, pp. 203-232.
Yan et al., "Synthesis, crystal structure and antibacterial activity of dibutylitin carboxylate", Huaxue Tongbao (2007), 70(4), 313-316 CODEN: HHTPAU; ISSN: 0441-3776.
Yan et al., "Synthesis, crystal structure and antibacterial activity of di-n-butyltin di-2(2-formylphenoxy)acetic ester", Yingyong Huaxue (2007), 24(6), 660-664.
Yang, et al. Structural requirement of chalcones for the inhibitory activity of interleukin-5. Bioorg Med Chem. Jan. 1, 2007;15(1):104-11. Epub Oct. 10, 2006.
Yoon et al., The Chirality Conversion Reagent for Amino Acids Based on Salicyl Aldehyde. Bull. Korean Chem. Soc., (2012), 33:1715-1718.
Zhang et al., "DFT study on RuII-catalyzed cyclization of terminal alkynals to cycloalkenes", International Journal of Quantum Chemistry (2009), 109(4), 679-687 CODEN: IJQCB2; ISSN:0020-7608.
Zhang, et al. A selective fluorescent chemosensor with 1, 2, 4-triazole as subunit for Cu (II) and its application in imaging Cu (II) in living cells. Dyes and Pigments. 2012; 92(3):1370-1375.
Zhang, et al. Current prodrug strategies for improving oral absorption of nucleoside analogues. Asian Journal of Pharmaceutical Sciences. Apr. 2014; 9(2):65-74.
Zhu et al., "Isoquinoline-pyridine-based protein kinase B/Akt antagonists: SAR and in vivo antitumor activity", Bioorganic & Medicinal Chemistry Letters, Pergamon, Amsterdam, NL, 2006, vol. 16, No. 12, pp. 3150-3155.
Zwaagstra et al., "Synthesis and Structure-Activity Relationships of Carboxylated Chalcones: A Novel Series of Cys-LT1 (LTD4) Receptor Antagonists", Journal of Medicinal Chemistry (1997), 40(7), 1075-1089 CODEN: JMCMAR; ISSN: 0022-2623.

COMPOUNDS AND USES THEREOF FOR THE MODULATION OF HEMOGLOBIN

CROSS-REFERENCE TO RELATED APPLICATIONS

This application is a continuation of U.S. application Ser. No. 16/186,275, filed Nov. 9, 2018, which is a continuation of U.S. application Ser. No. 14/776,726, filed Sep. 14, 2015, now abandoned, which is the U.S. national stage application of International Patent Application No. PCT/US2014/022769, filed Mar. 10, 2014, which claims priority to U.S. Application No. 61/905,803, filed Nov. 18, 2013.

FIELD OF THE INVENTION

This invention provides compounds and pharmaceutical compositions suitable as allosteric modulators of hemoglobin, methods and intermediates for their preparation, and methods for their use in treating disorders mediated by hemoglobin and disorders that would benefit from tissue and/or cellular oxygenation.

STATE OF THE ART

Sickle cell disease is a disorder of the red blood cells, found particularly among those of African and Mediterranean descent. The basis for sickle cell disease is found in sickle hemoglobin (HbS), which contains a point mutation relative to the prevalent peptide sequence of hemoglobin (Hb).

Hemoglobin (Hb) transports oxygen molecules from the lungs to various tissues and organs throughout the body. Hemoglobin binds and releases oxygen through conformational changes. Sickle hemoglobin (HbS) contains a point mutation where glutamic acid is replaced with valine, allowing HbS to become susceptible to polymerization to give the HbS containing red blood cells their characteristic sickle shape. The sickled cells are also more rigid than normal red blood cells, and their lack of flexibility can lead to blockage of blood vessels. U.S. Pat. No. 7,160,910 discloses compounds that are allosteric modulators of hemoglobin. However, a need exists for additional therapeutics that can treat disorders that are mediated by Hb or by abnormal Hb such as HbS.

SUMMARY OF THE INVENTION

This invention relates generally to compounds and pharmaceutical compositions suitable as allosteric modulators of hemoglobin. In some aspects, this invention relates to methods for treating disorders mediated by hemoglobin and disorders that would benefit from tissue and/or cellular oxygenation.

In certain aspects of the invention, a compound of Formula (A) is provided:

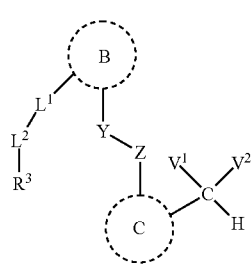

(A)

or a tautomer thereof, or pharmaceutically acceptable salt of each of thereof or a pharmaceutically acceptable salt thereof, wherein $L^1$ is a bond or is $NR^{70}$, O, S, or $(CR^{71}R^{72})_d$; wherein each $R^{70}$, $R^{71}$, and $R^{72}$ independently are hydrogen or $C_1$-$C_6$ alkyl;

d is 1, 2, or 3;

$L^2$ is C=O or $SO_2$;

each Y and Z is independently $CR^{10}R^{11}$, O, S, SO, $SO_2$, or $NR^{10}$; each $R^{10}$ and $R^{11}$ independently is hydrogen or $C_1$-$C_3$ alkyl optionally substituted with 1-3 halo, OH, or $C_1$-$C_6$ alkoxy, or $CR^{10}R^{11}$ is C=O, provided that if one of Y and Z is O, S, SO, $SO_2$, then the other is not CO, and Y and Z are both not heteroatoms or oxidized forms thereof;

wherein Y is α or β substituted relative to the $-L^1L^2R^3$;

wherein Z and $-CV^1V^2H$ are joined to adjacent atoms on ring C;

$V^1$ and $V^2$ independently are $C_1$-$C_6$ alkoxy; or $V^1$ and $V^2$ together with the carbon atom they are attached to form a ring of formula:

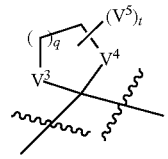

wherein each $V^3$ and $V^4$ are independently O, S, or NH, provided that when one of $V^3$ and $V^4$ is S, the other is NH, and provided that $V^3$ and $V^4$ are both not NH; q is 1 or 2; each $V^5$ is independently $C_1$-$C_6$ alkyl or $CO_2R^{60}$, where each $R^{60}$ independently is $C_1$-$C_6$ alkyl or hydrogen; t is 0, 1, 2, or 4; or $CV^1V^2$ is C=V, wherein V is O, $NOR^{80}$, or $NNR^{81}R^{82}$;

$R^{80}$ is optionally substituted $C_1$-$C_6$ alkyl;

$R^{81}$ and $R^{82}$ independently are selected from the group consisting of hydrogen; optionally substituted $C_1$-$C_6$ alkyl, $COR^{83}$ and $CO_2R^{84}$;

$R^{83}$ is hydrogen or optionally substituted $C_1$-$C_6$ alkyl; and $R^{84}$ is optionally substituted $C_1$-$C_6$ alkyl.

and $R^3$, B, and C are defined as follows.

In one instance, $R^3$ is $C_1$-$C_6$ alkyl, $C_3$-$C_8$ cycloalkyl, $C_1$-$C_6$ alkoxy, $C_3$-$C_8$ cycloalkoxy, or $-NR^1R^2$;

each $R^1$ and $R^2$ independently is hydrogen, $C_1$-$C_6$ alkyl, $C_3$-$C_8$ cycloalkyl, $C_6$-$C_{10}$aryl, 4-10 membered heterocycle or 5-10 membered heteroaryl, each containing up to 5 ring heteroatoms, wherein the heteroatom is selected from the group consisting of O, N, S, and oxidized forms of N and S, wherein each alkyl, cycloalkyl, heterocycle, aryl or heteroaryl is optionally substituted, or $R^1$ and $R^2$ together with the nitrogen atom they are attached to form an optionally substituted 4-7 membered heterocycle;

ring B is a optionally substituted $C_6$-$C_{10}$aryl, optionally substituted 5-10 membered heteroaryl having 1-3 nitrogen atoms or oxidized forms of N, or optionally substituted 4-10 membered heterocycle containing up to 5 ring heteroatoms, wherein the heteroatom is selected from the group consisting of O, N, S, and oxidized forms of N and S; and ring C is a optionally substituted $C_6$-$C_{10}$aryl or optionally substituted 5-10 membered heteroaryl containing 1-3 nitrogen atoms, or an oxidized form of N, wherein certain preferred substituents include OH, halo, $C_1$-$C_6$ alkoxy, $C_3$-$C_6$ cycloalkoxy or O—R, where R is a prodrug moiety, wherein the $C_1$-$C_6$ alkoxy is optionally substituted with 1-5 halo.

In another instance, $R^3$ is $C_6$-$C_{10}$ aryl, or a 5-10 membered heteroaryl, wherein the heteroatom is selected from the group consisting of O, N, S, and oxidized forms of N and S, wherein each of the aryl, or heteroaryl is optionally substituted with 1-4 $C_1$-$C_6$ alkyl;

ring B is a optionally substituted 4-10 membered heterocycle containing up to 5 ring heteroatoms, wherein the heteroatom is selected from the group consisting of O, N, S, and oxidized forms of N and S;

ring C is $C_6$-$C_{10}$ aryl or a 5-10 membered heteroaryl containing up to 5 ring heteroatoms, wherein the heteroatom is selected from the group consisting of O, N, S, and oxidized forms of N and S, each of which is optionally substituted with 1-4: halo, oxo, —$OR^{19}$, $C_1$-$C_6$ alkyl, and/or $C_1$-$C_6$ alkoxy, wherein the $C_1$-$C_6$ alkyl is optionally substituted with 1-5 halo, $C_1$-$C_6$alkoxy and/or a 4-10 membered heterocycle containing up to 5 ring heteroatoms, wherein the heteroatom is selected from the group consisting of O, N, S, and oxidized forms of N and S, wherein certain preferred substituents include OH, halo, $C_1$-$C_6$alkoxy, $C_3$-$C_6$ cycloalkoxy or O—R, where R is a prodrug moiety, wherein the $C_1$-$C_6$alkoxy is optionally substituted with 1-5 halo; and $R^{19}$ is hydrogen or a prodrug moiety R.

In certain aspects of the invention, a compound of Formula (II) is provided:

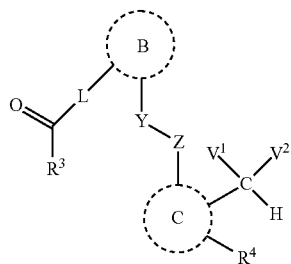

(II)

or a tautomer thereof, or pharmaceutically acceptable salt of each of thereof, wherein $R^3$ is $C_1$-$C_6$ alkyl, $C_3$-$C_8$ cycloalkyl, $C_1$-$C_6$alkoxy, $C_3$-$C_8$ cycloalkoxy, or —$NR^1R^2$;

each $R^1$ and $R^2$ independently is hydrogen, $C_1$-$C_6$ alkyl, $C_3$-$C_8$ cycloalkyl, $C_6$-$C_{10}$aryl, 4-10 membered heterocycle or 5-10 membered heteroaryl, each containing up to 5 ring heteroatoms, wherein the heteroatom is selected from the group consisting of O, N, S, and oxidized forms of N and S, wherein each alkyl, cycloalkyl, heterocycle, aryl or heteroaryl is optionally substituted, or $R^1$ and $R^2$ together with the nitrogen atom they are attached to form an optionally substituted 4-7 membered heterocycle;

L is a bond or is $NR^{70}$, O, S, or $(CR^{71}R^{72})_d$; wherein each $R^{70}$, $R^{71}$, and $R^{72}$ independently are hydrogen or $C_1$-$C_6$ alkyl;

d is 1, 2, or 3;

ring B is a optionally substituted $C_6$-$C_{10}$ aryl, optionally substituted 5-10 membered heteroaryl having 1-3 nitrogen atoms or oxidized forms of N, or optionally substituted 4-10 membered heterocycle containing up to 5 ring heteroatoms, wherein the heteroatom is selected from the group consisting of O, N, S, and oxidized forms of N and S;

each Y and Z is independently $CR^{10}R^{11}$, O, S, SO, $SO_2$, or $NR^{10}$; each $R^{10}$ and $R^{11}$ independently is hydrogen or $C_1$-$C_3$ alkyl optionally substituted with 1-3 halo, OH, or $C_1$-$C_6$ alkoxy, or $CR^{10}R^{11}$ is C=O, provided that if one of Y and Z is O, S, SO, $SO_2$, then the other is not CO, and Y and Z are both not heteroatoms or oxidized forms thereof;

wherein Y is α or β substituted relative to the -$LCOR^3$;

ring C is a optionally substituted $C_6$-$C_{10}$aryl or optionally substituted 5-10 membered heteroaryl containing 1-3 nitrogen atoms, or an oxidized form of N;

wherein Z and —$CV^1V^2H$ are joined to adjacent atoms on ring C;

$V^1$ and $V^2$ independently are $C_1$-$C_6$ alkoxy; or $V^1$ and $V^2$ together with the carbon atom they are attached to form a ring of formula:

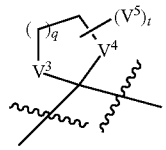

wherein each $V^3$ and $V^4$ are independently O, S, or NH, provided that when one of $V^3$ and $V^4$ is S, the other is NH, and provided that $V^3$ and $V^4$ are both not NH; q is 1 or 2; each $V^5$ is independently $C_1$-$C_6$ alkyl or $CO_2R^{60}$, where each $R^{60}$ independently is $C_1$-$C_6$ alkyl or hydrogen; t is 0, 1, 2, or 4; or $CV^1V^2$ is C=V, wherein V is O, $NOR^{80}$, or $NNR^{81}R^{82}$;

$R^4$ is OH, halo, $C_1$-$C_6$ alkoxy, $C_3$-$C_6$ cycloalkoxy or O—R, where R is a prodrug moiety, wherein the $C_1$-$C_6$ alkoxy is optionally substituted with 1-5 halo;

$R^{80}$ is optionally substituted $C_1$-$C_6$ alkyl;

$R^{81}$ and $R^{82}$ independently are selected from the group consisting of hydrogen; optionally substituted $C_1$-$C_6$ alkyl, $COR^{83}$ and $CO_2R^{84}$;

$R^{83}$ is hydrogen or optionally substituted $C_1$-$C_6$ alkyl; and $R^{84}$ is optionally substituted $C_1$-$C_6$ alkyl.

In certain aspects of the invention, a compound of formula (IV) is provided:

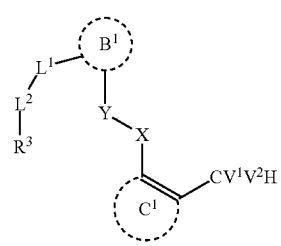

(IV)

wherein $R^3$ is $C_6$-$C_{10}$ aryl, or a 5-10 membered heteroaryl, wherein the heteroatom is selected from the group consisting of O, N, S, and oxidized forms of N and S, wherein each of the aryl, or heteroaryl is optionally substituted with 1-4: $C_1$-$C_6$ alkyl;

$L^1$ is a bond or is $NR^{70}$, O, S, or $(CR^{71}R^{72})_d$; wherein each $R^{70}$, $R^{71}$, and $R^{72}$ independently are hydrogen or $C_1$-$C_6$ alkyl;

d is 1, 2, or 3;

$L^2$ is C=O or $SO_2$;

ring B is a optionally substituted 4-10 membered heterocycle containing up to 5 ring heteroatoms, wherein the heteroatom is selected from the group consisting of O, N, S, and oxidized forms of N and S;

each Y and Z is independently $(CR^{10}R^{11})_e$, S, SO, $SO_2$, or $NR^{10}$; e is 1 to 4, preferably 1; each $R^{10}$ and $R^{11}$ independently is hydrogen or $C_1$-$C_3$ alkyl optionally substituted with 1-3 halo, OH, or $C_1$-$C_6$ alkoxy, or $CR^{10}R^{11}$ is C=O, provided that if one of Y and Z is O, S, SO, $SO_2$, then the other is not CO, and Y and Z are both not heteroatoms or oxidized forms thereof;

wherein Y is α or β substituted relative to the -$L^1L^2R^3$;

ring C is $C_6$-$C_{10}$ aryl or a 5-10 membered heteroaryl containing up to 5 ring heteroatoms, wherein the heteroatom is selected from the group consisting of O, N, S, and oxidized forms of N and S, each of which is optionally substituted with 1-4: halo, oxo, —$OR^2$, $C_1$-$C_6$ alkyl, and/or $C_1$-$C_6$ alkoxy, wherein the $C_1$-$C_6$ alkyl is optionally substituted with 1-5 halo, $C_1$-$C_6$ alkoxy and/or a 4-10 membered heterocycle containing up to 5 ring heteroatoms, wherein the heteroatom is selected from the group consisting of O, N, S, and oxidized forms of N and 5;

$R^2$ is hydrogen or a prodrug moiety R; and wherein Z and —$CV^1V^2H$ are attached to adjacent atoms on ring C;

$V^1$ and $V^2$ independently are $C_1$-$C_6$ alkoxy; or $V^1$ and $V^2$ together with the carbon atom they are attached to form a ring of formula:

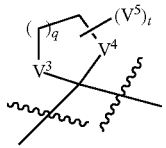

wherein each $V^3$ and $V^4$ are independently O, S, or NH, provided that when one of $V^3$ and $V^4$ is S, the other is NH, and provided that $V^3$ and $V^4$ are both not NH; q is 1 or 2; each $V^5$ is independently $C_1$-$C_6$ alkyl or $CO_2R^{60}$, where each $R^{60}$ independently is $C_1$-$C_6$ alkyl or hydrogen; t is 0, 1, 2, or 4; or $CV^1V^2$ is C=V, wherein V is O, $NOR^{80}$, or $NNR^{81}R^{82}$;

$R^{80}$ is optionally substituted $C_1$-$C_6$ alkyl;

$R^{81}$ and $R^{82}$ independently are selected from the group consisting of hydrogen; optionally substituted $C_1$-$C_6$ alkyl, $COR^{83}$ and $CO_2R^{84}$;

$R^{83}$ is hydrogen or optionally substituted $C_1$-$C_6$ alkyl; and $R^{84}$ is optionally substituted $C_1$-$C_6$ alkyl.

In one embodiment, ring b is joined to $L^1$ or $L^2$ via a nitrogen atom. In another embodiment, $R^3$ is joined to $L^2$ via a nitrogen atom.

In further aspects of the invention, a composition is provided comprising any of the compounds described herein, and at least a pharmaceutically acceptable excipient.

In still further aspects of the invention, a method is provided for increasing oxygen affinity of hemoglobin S in a subject, the method comprising administering to a subject in need thereof a therapeutically effective amount of any of the compounds or compositions described herein.

In further aspects of the invention, a method is provided for treating oxygen deficiency associated with sickle cell anemia, the method comprising administering to a subject in need thereof a therapeutically effective amount of any of the compounds or compositions described herein.

DETAILED DESCRIPTION OF THE INVENTION

Definitions

It must be noted that as used herein and in the appended claims, the singular forms "a", "an", and "the" include plural referents unless the context clearly dictates otherwise. Thus, for example, reference to "a solvent" includes a plurality of such solvents.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition or process consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations. Each numerical parameter should at least be construed in light of the number of reported significant digits and by applying ordinary rounding techniques. The term "about" when used before a numerical designation, e.g., temperature, time, amount, and concentration, including range, indicates approximations which may vary by (+) or (−) 10%, 5% or 1%.

As used herein, $C_m$-$C_n$, such as $C_1$-$C_{12}$, $C_1$-$C_8$, or $C_1$-$C_6$ when used before a group refers to that group containing m to n carbon atoms.

The term "alkoxy" refers to —O-alkyl. Cycloalkoxy refers to —O-cycloalkyl.

The term "alkyl" refers to monovalent saturated aliphatic hydrocarbyl groups having from 1 to 30 carbon atoms (i.e., $C_1$-$C_{30}$ alkyl) or 1 to 22 carbon atoms (i.e., $C_1$-$C_{22}$ alkyl), 1 to 8 carbon atoms (i.e., $C_1$-$C_8$ alkyl), or 1 to 4 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

The term "aryl" refers to a monovalent, aromatic mono- or bicyclic ring having 6-10 ring carbon atoms. Examples of aryl include phenyl and naphthyl. The condensed ring may or may not be aromatic provided that the point of attachment is at an aromatic carbon atom. For example, and without limitation, the following is an aryl group:

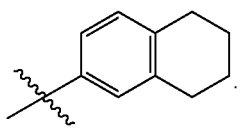 [SMILES: *c1ccc2c(c1)CCCC2]

The term "—CO₂H ester" refers to an ester formed between the —CO₂H group and an alcohol, preferably an aliphatic alcohol. A preferred example included —CO₂R$^E$, wherein R$^E$ is alkyl or aryl group optionally substituted with an amino group.

The term "chiral moiety" refers to a moiety that is chiral. Such a moiety can possess one or more asymmetric centers. Preferably, the chiral moiety is enantiomerically enriched, and more preferably a single enantiomer. Non limiting examples of chiral moieties include chiral carboxylic acids, chiral amines, chiral amino acids, such as the naturally occurring amino acids, chiral alcohols including chiral steroids, and the likes.

The term "cycloalkyl" refers to a monovalent, preferably saturated, hydrocarbyl mono-, bi-, or tricyclic ring having 3-12 ring carbon atoms. While cycloalkyl, refers preferably to saturated hydrocarbyl rings, as used herein, it also includes rings containing 1-2 carbon-carbon double bonds. Nonlimiting examples of cycloalkyl include cyclopropyl, cyclobutyl, cyclopentyl, cyclohexyl, cycloheptyl, adamentyl, and the like. The condensed rings may or may not be non-aromatic hydrocarbyl rings provided that the point of attachment is at a cycloalkyl carbon atom. For example, and without limitation, the following is a cycloalkyl group:

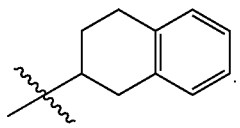 [SMILES: *C1CCc2ccccc2C1]

The term "halo" refers to F, Cl, Br, and/or I.

The term "heteroaryl" refers to a monovalent, aromatic mono-, bi-, or tricyclic ring having 2-16 ring carbon atoms and 1-8 ring heteroatoms selected preferably from N, O, S, and P and oxidized forms of N, S, and P, provided that the ring contains at least 5 ring atoms. Nonlimiting examples of heteroaryl include furan, imidazole, oxadiazole, oxazole, pyridine, quinoline, and the like. The condensed rings may or may not be a heteroatom containing aromatic ring provided that the point of attachment is a heteroaryl atom. For example, and without limitation, the following is a heteroaryl group:

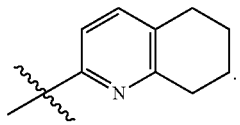 [SMILES: *c1ccc2c(n1)CCCC2]

The term "heterocyclyl" or heterocycle refers to a non-aromatic, mono-, bi-, or tricyclic ring containing 2-12 ring carbon atoms and 1-8 ring heteroatoms selected preferably from N, O, S, and P and oxidized forms of N, S, and P, provided that the ring contains at least 3 ring atoms. While heterocyclyl preferably refers to saturated ring systems, it also includes ring systems containing 1-3 double bonds, provided that the ring is non-aromatic. Nonlimiting examples of heterocyclyl include, azalactones, oxazoline, piperidinyl, piperazinyl, pyrrolidinyl, tetrahydrofuranyl, and tetrahydropyranyl. The condensed rings may or may not contain a non-aromatic heteroatom containing ring provided that the point of attachment is a heterocyclyl group. For example, and without limitation, the following is a heterocyclyl group:

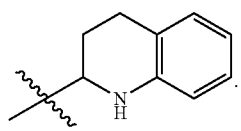 [SMILES: *C1CCc2ccccc2N1]

The term "hydrolyzing" refers to breaking an R$^H$—O—CO—, R$^H$—O—CS—, or an R$^H$—O—SO₂— moiety to an R$^H$—OH, preferably by adding water across the broken bond. A hydrolyzing is performed using various methods well known to the skilled artisan, non limiting examples of which include acidic and basic hydrolysis.

The term "oxo" refers to a C=O group, and to a substitution of 2 geminal hydrogen atoms with a C=O group.

The term "optionally substituted" refers to a substituted or unsubstituted group. The group may be substituted with one or more substituents, such as e.g., 1, 2, 3, 4 or 5 substituents. Preferably, the substituents are selected from the group consisting of oxo, halo, —CN, NO₂, —N₂+, —CO₂R$^{100}$, —OR$^{100}$, —SR$^{100}$, —SOR$^{100}$, —SO₂R$^{100}$, —NR$^{101}$R$^{102}$, —CONR$^{101}$R$^{101}$, —CONR$^{101}$R$^{102}$, —SO₂NR$^{101}$R$^{102}$, C₁-C₆ alkyl, C₁-C₆ alkoxy, —CR$^{100}$=C(R$^{100}$)₂, —CCR$^{100}$, C₃-C₁₀ cycloalkyl, C₃-C₁₀ heterocyclyl, C₆-C₁₂ aryl and C₂-C₁₂ heteroaryl, wherein each R$^{100}$ independently is hydrogen or C₁-C₈ alkyl; C₃-C₁₂ cycloalkyl; C₃-C₁₀ heterocyclyl; C₆-C₁₂ aryl; or C₂-C₁₂ heteroaryl; wherein each alkyl, cycloalkyl, heterocyclyl, aryl, or heteroaryl is optionally substituted with 1-3 halo, 1-3 C₁-C₆ alkyl, 1-3 C₁-C₆ haloalkyl or 1-3 C₁-C₆ alkoxy groups. Preferably, the substituents are selected from the group consisting of chloro, fluoro, —OCH₃, methyl, ethyl, iso-propyl, cyclopropyl, vinyl, ethynyl, —CO₂H, —CO₂CH₃, —OCF₃, —CF₃ and —OCHF₂.

R$^{101}$ and R$^{102}$ independently is hydrogen; C₁-C₈ alkyl, optionally substituted with —CO₂H or an ester thereof, C₁-C₆ alkoxy, oxo, —CR$^{103}$=C(R$^{103}$)₂, —CCR, C₃-C₁₀ cycloalkyl, C₃-C₁₀ heterocyclyl, C₆-C₁₂ aryl, or C₂-C₁₂ heteroaryl, wherein each R$^{103}$ independently is hydrogen or C₁-C₈ alkyl; C₃-C₁₂ cycloalkyl; C₃-C₁₀ heterocyclyl; C₆-C₁₂ aryl; or C₂-C₁₂ heteroaryl; wherein each cycloalkyl, heterocyclyl, aryl, or heteroaryl is optionally substituted with 1-3 alkyl groups or 1-3 halo groups, or R$^{101}$ and R$^{102}$ together with the nitrogen atom they are attached to form a 5-7 membered heterocycle.

The term "pharmaceutically acceptable" refers to safe and non-toxic for in vivo, preferably, human administration.

The term "pharmaceutically acceptable salt" refers to a salt that is pharmaceutically acceptable.

The term "salt" refers to an ionic compound formed between an acid and a base. When the compound provided herein contains an acidic functionality, such salts include, without limitation, alkali metal, alkaline earth metal, and ammonium salts. As used herein, ammonium salts include, salts containing protonated nitrogen bases and alkylated nitrogen bases. Exemplary, and non-limiting cations useful in pharmaceutically acceptable salts include Na, K, Rb, Cs, $NH_4$, Ca, Ba, imidazolium, and ammonium cations based on naturally occurring amino acids. When the compounds utilized herein contain basic functionality, such salts include, without limitation, salts of organic acids, such as carboxylic acids and sulfonic acids, and mineral acids, such as hydrogen halides, sulfuric acid, phosphoric acid, and the likes. Exemplary and non-limiting anions useful in pharmaceutically acceptable salts include oxalate, maleate, acetate, propionate, succinate, tartrate, chloride, sulfate, bisalfate, mono-, di-, and tribasic phosphate, mesylate, tosylate, and the likes.

The terms "treat", "treating" or "treatment", as used herein, include alleviating, abating or ameliorating a disease or condition or one or more symptoms thereof, preventing additional symptoms, ameliorating or preventing the underlying metabolic causes of symptoms, inhibiting the disease or condition, e.g., arresting or suppressing the development of the disease or condition, relieving the disease or condition, causing regression of the disease or condition, relieving a condition caused by the disease or condition, or suppressing the symptoms of the disease or condition, and are intended to include prophylaxis. The terms also include relieving the disease or conditions, e.g., causing the regression of clinical symptoms. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the individual, notwithstanding that the individual is still be afflicted with the underlying disorder. For prophylactic benefit, the compositions are administered to an individual at risk of developing a particular disease, or to an individual reporting one or more of the physiological symptoms of a disease, even though a diagnosis of this disease has not been made.

The terms "preventing" or "prevention" refer to a reduction in risk of acquiring a disease or disorder (i.e., causing at least one of the clinical symptoms of the disease not to develop in a subject that may be exposed to or predisposed to the disease but does not yet experience or display symptoms of the disease). The terms further include causing the clinical symptoms not to develop, for example in a subject at risk of suffering from such a disease or disorder, thereby substantially averting onset of the disease or disorder.

The term "effective amount" refers to an amount that is effective for the treatment of a condition or disorder by an intranasal administration of a compound or composition described herein. In some embodiments, an effective amount of any of the compositions or dosage forms described herein is the amount used to treat a disorder mediated by hemoglobin or a disorder that would benefit from tissue and/or cellular oxygenation of any of the compositions or dosage forms described herein to a subject in need thereof.

The term "carrier" as used herein, refers to relatively nontoxic chemical compounds or agents that facilitate the incorporation of a compound into cells, e.g., red blood cells, or tissues.

As used herein, a "prodrug" is a compound that, after administration, is metabolized or otherwise converted to an active or more active form with respect to at least one property. To produce a prodrug, a pharmaceutically active compound can be modified chemically to render it less active or inactive, but the chemical modification is such that an active form of the compound is generated by metabolic or other biological processes. A prodrug may have, relative to the drug, altered metabolic stability or transport characteristics, fewer side effects or lower toxicity. For example, see the reference Nogrady, 1985, Medicinal Chemistry A Biochemical Approach, Oxford University Press, New York, pages 388-392. Prodrugs can also be prepared using compounds that are not drugs.

Compounds

In certain aspects of the invention, a compound of Formula (I) is provided:

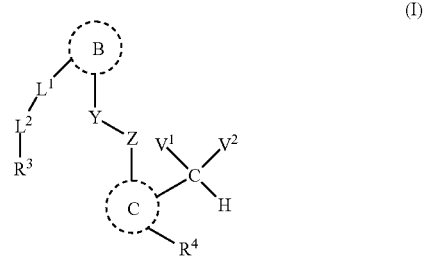

(I)

or a tautomer thereof, or pharmaceutically acceptable salt of each of thereof or a pharmaceutically acceptable salt thereof, wherein $L^1$ is a bond or is $NR^{70}$, O, S, or $(CR^{71}R^{72})_d$; wherein each $R^{70}$, $R^{71}$, and $R^{72}$ independently are hydrogen or $C_1$-$C_6$ alkyl;

d is 1, 2, or 3;

$L^2$ is C=O or $SO_2$;

each Y and Z is independently $CR^{10}R^{11}$, O, S, SO, $SO_2$, or $NR^{10}$; each $R^{10}$ and $R^{11}$ independently is hydrogen or $C_1$-$C_3$ alkyl optionally substituted with 1-3 halo, OH, or $C_1$-$C_6$ alkoxy, or $CR^{10}R^{11}$ is C=O, provided that if one of Y and Z is O, S, SO, $SO_2$, then the other is not CO, and Y and Z are both not heteroatoms or oxidized forms thereof;

wherein Y is α or β substituted relative to the -$L^1L^2R^3$;

wherein Z and —$CV^1V^2$H are joined to adjacent atoms on ring C;

$V^1$ and $V^2$ independently are $C_1$-$C_6$ alkoxy; or $V^1$ and $V^2$ together with the carbon atom they are attached to form a ring of formula:

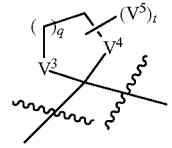

wherein each $V^3$ and $V^4$ are independently O, S, or NH, provided that when one of $V^3$ and $V^4$ is S, the other is NH, and provided that $V^3$ and $V^4$ are both not NH; q is 1 or 2; each $V^5$ is independently $C_1$-$C_6$ alkyl or $CO_2R^{60}$, where each $R^{60}$ independently is $C_1$-$C_6$ alkyl or hydrogen; t is 0, 1, 2, or 4; or $CV^1V^2$ is C=V, wherein V is O, $NOR^{80}$, or $NNR^{81}R^{82}$;

$R^4$ is OH, halo, $C_1$-$C_6$ alkoxy, $C_3$-$C_6$ cycloalkoxy or O—R, where R is a prodrug moiety, wherein the $C_1$-$C_6$ alkoxy is optionally substituted with 1-5 halo;

$R^{80}$ is optionally substituted $C_1$-$C_6$ alkyl;

$R^{81}$ and $R^{82}$ independently are selected from the group consisting of hydrogen; optionally substituted $C_1$-$C_6$ alkyl, $COR^{83}$ and $CO_2R^{84}$;

$R^{83}$ is hydrogen or optionally substituted $C_1$-$C_6$ alkyl; and $R^{84}$ is optionally substituted $C_1$-$C_6$ alkyl.

and $R^3$, B, and C are defined as follows.

In one instance, $R^3$ is $C_1$-$C_6$ alkyl, $C_3$-$C_8$ cycloalkyl, $C_1$-$C_6$ alkoxy, $C_3$-$C_8$ cycloalkoxy, or —$NR^1R^2$;

each $R^1$ and $R^2$ independently is hydrogen, $C_1$-$C_6$ alkyl, $C_3$-$C_8$ cycloalkyl, $C_6$-$C_{10}$aryl, 4-10 membered heterocycle or 5-10 membered heteroaryl, each containing up to 5 ring heteroatoms, wherein the heteroatom is selected from the group consisting of O, N, S, and oxidized forms of N and S, wherein each alkyl, cycloalkyl, heterocycle, aryl or heteroaryl is optionally substituted, or $R^1$ and $R^2$ together with the nitrogen atom they are attached to form an optionally substituted 4-7 membered heterocycle;

ring B is a optionally substituted $C_6$-$C_{10}$aryl, optionally substituted 5-10 membered heteroaryl having 1-3 nitrogen atoms or oxidized forms of N, or optionally substituted 4-10 membered heterocycle containing up to 5 ring heteroatoms, wherein the heteroatom is selected from the group consisting of O, N, S, and oxidized forms of N and S; and ring C is a optionally substituted $C_6$-$C_{10}$aryl or optionally substituted 5-10 membered heteroaryl containing 1-3 nitrogen atoms, or an oxidized form of N;

In another instance, $R^3$ is $C_6$-$C_{10}$ aryl, or a 5-10 membered heteroaryl, wherein the heteroatom is selected from the group consisting of O, N, S, and oxidized forms of N and S, wherein each of the aryl, or heteroaryl is optionally substituted with 1-4 $C_1$-$C_6$ alkyl;

ring B is a optionally substituted 4-10 membered heterocycle containing up to 5 ring heteroatoms, wherein the heteroatom is selected from the group consisting of O, N, S, and oxidized forms of N and S;

ring C is $C_6$-$C_{10}$ aryl or a 5-10 membered heteroaryl containing up to 5 ring heteroatoms, wherein the heteroatom is selected from the group consisting of O, N, S, and oxidized forms of N and S, each of which is optionally substituted with 1-4: halo, oxo, —$OR^{19}$, $C_1$-$C_6$ alkyl, and/or $C_1$-$C_6$ alkoxy, wherein the $C_1$-$C_6$ alkyl is optionally substituted with 1-5 halo, $C_1$-$C_6$alkoxy and/or a 4-10 membered heterocycle containing up to 5 ring heteroatoms, wherein the heteroatom is selected from the group consisting of O, N, S, and oxidized forms of N and S; and $R^{19}$ is hydrogen or a prodrug moiety R.

In certain embodiments, $L^1$ is a bond.

In certain embodiments, $L^2$ is C=O. In certain embodiments, $L^2$ is $SO_2$.

In one embodiment, ring C is phenyl which is optionally substituted with 1-4: halo, oxo, —$OR^2$, $C_1$-$C_6$ alkyl and/or $C_1$-$C_6$alkoxy, In certain aspects of the invention, a compound of Formula (II) is provided:

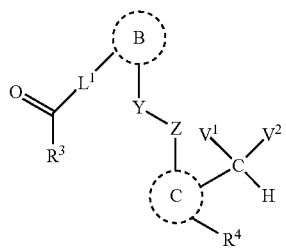

(II)

or a tautomer thereof, or pharmaceutically acceptable salt of each of thereof or a pharmaceutically acceptable salt thereof, wherein $R^3$ is $C_1$-$C_6$ alkyl, $C_3$-$C_8$ cycloalkyl, $C_1$-$C_6$ alkoxy, $C_3$-$C_8$ cycloalkoxy, or —$NR^1R^2$;

each $R^1$ and $R^2$ independently is hydrogen, $C_1$-$C_6$ alkyl, $C_3$-$C_8$ cycloalkyl, $C_6$-$C_{10}$ aryl, 4-10 membered heterocycle or 5-10 membered heteroaryl, each containing up to 5 ring heteroatoms, wherein the heteroatom is selected from the group consisting of O, N, S, and oxidized forms of N and S, wherein each alkyl, cycloalkyl, heterocycle, aryl or heteroaryl is optionally substituted, or $R^1$ and $R^2$ together with the nitrogen atom they are attached to form an optionally substituted 4-7 membered heterocycle;

$L^1$ is a bond or is $NR^{70}$, O, S, or $(CR^{71}R^{72})_d$; wherein each $R^{70}$, $R^{71}$, and $R^{72}$ independently are hydrogen or $C_1$-$C_6$ alkyl;

d is 1, 2, or 3;

ring B is a optionally substituted $C_6$-$C_{10}$ aryl, optionally substituted 5-10 membered heteroaryl having 1-3 nitrogen atoms or oxidized forms of N, or optionally substituted 4-10 membered heterocycle containing up to 5 ring heteroatoms, wherein the heteroatom is selected from the group consisting of O, N, S, and oxidized forms of N and S;

each Y and Z is independently $CR^{10}R^{11}$, O, S, SO, $SO_2$, or $NR^{10}$; each $R^{10}$ and $R^{11}$ independently is hydrogen or $C_1$-$C_3$ alkyl optionally substituted with 1-3 halo, OH, or $C_1$-$C_6$ alkoxy, or $CR^{10}R^{11}$ is C=O, provided that if one of Y and Z is O, S, SO, $SO_2$, then the other is not CO, and Y and Z are both not heteroatoms or oxidized forms thereof;

wherein Y is α or β substituted relative to the -$LCOR^3$;

ring C is a optionally substituted $C_6$-$C_{10}$ aryl or optionally substituted 5-10 membered heteroaryl containing 1-3 nitrogen atoms, or an oxidized form of N;

wherein Z and —$CV^1V^2$H are joined to adjacent atoms on ring C;

$V^1$ and $V^2$ independently are $C_1$-$C_6$ alkoxy; or $V^1$ and $V^2$ together with the carbon atom they are attached to form a ring of formula:

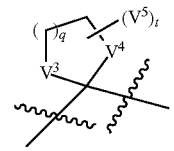

wherein each $V^3$ and $V^4$ are independently O, S, or NH, provided that when one of $V^3$ and $V^4$ is S, the other is NH, and provided that $V^3$ and $V^4$ are both not NH; q is 1 or 2; each $V^5$ is independently $C_1$-$C_6$ alkyl or $CO_2R^{60}$, where each $R^{60}$ independently is $C_1$-$C_6$ alkyl or hydrogen; t is 0, 1, 2, or 4; or $CV^1V^2$ is C=V, wherein V is O, $NOR^{80}$, or $NNR^{81}R^{82}$;

$R^4$ is OH, halo, $C_1$-$C_6$ alkoxy, $C_3$-$C_6$ cycloalkoxy or O—R, where R is a prodrug moiety, wherein the $C_1$-$C_6$ alkoxy is optionally substituted with 1-5 halo;

$R^{80}$ is optionally substituted $C_1$-$C_6$ alkyl;

$R^{81}$ and $R^{82}$ independently are selected from the group consisting of hydrogen; optionally substituted $C_1$-$C_6$ alkyl, $COR^{83}$ and $CO_2R^{84}$;

$R^{83}$ is hydrogen or optionally substituted $C_1$-$C_6$ alkyl; and $R^{84}$ is optionally substituted $C_1$-$C_6$ alkyl.

In certain embodiments, t is 0. In certain embodiments, t is 1. In certain embodiments, t is 2. In certain embodiments, t is 3.

As used herein, $R^{60}$ can be hydrogen, provided that the $COOR^{60}$ is not joined to a nitrogen atom.

Preferably, in certain embodiments, Y and Z are both not a heteroatom or a heteroatom containing moiety. Preferably, one of Y and Z is a methylene or substituted methylene and the other is a heteroatom or a heteroatom containing moiety. More preferably, Y is an alkylene, and Z is a heteroatom or a heteroatom containing moiety, which, yet more preferably is oxygen.

Preferably, $V^1$ and $V^2$ together with the carbon atom they are attached to form a ring of formula:

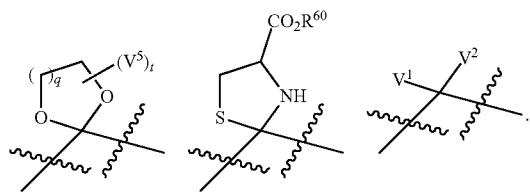

In some embodiments, $V^1$ and $V^2$ independently are $C_1$-$C_6$ alkoxy; or $V^1$ and $V^2$ together with the carbon atom they are attached to form a ring of formula:

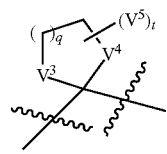

wherein each $V^3$ and $V^4$ are independently O, S, or NH, provided that when one or $V^3$ and $V^4$ is S the other is NH, and provided that $V^3$ and $V^4$ are both not NH; q is 1 or 2; each $V^5$ is independently $C_1$-$C_6$ alkyl or $CO_2R^{60}$, where each $R^{60}$ independently is $C_1$-$C_6$ alkyl or hydrogen; t is 0, 1, 2, or 4; or $CV^1V^2$ is C=V, wherein V is O.

In certain aspects of the invention, the compound of Formula (II) is of Formula (III):

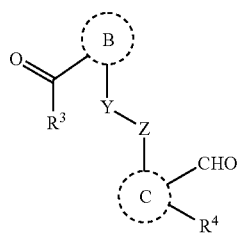

wherein Y—Z is —$CH_2O$— or —$CH_2CH_2$— and the remaining substituents are as defined herein.

In some embodiments, $R^4$ and —CHO are joined to adjacent atoms on ring C.

In certain aspects of the invention, the compound of Formula (II) is of Formula

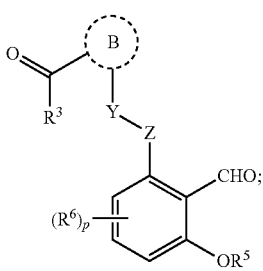

wherein ring B is a optionally substituted $C_6$-$C_{10}$ aryl, optionally substituted 5-10 membered heteroaryl having 1-3 nitrogen atoms or oxidized forms of N;
$R^5$ is hydrogen, $C_1$-$C_6$ alkyl or a prodrug moiety R;
$R^6$ is halo, $C_1$-$C_6$ alkyl, $C_3$-$C_6$ cycloalkyl, $C_1$-$C_6$ alkoxy, $C_3$-$C_6$ cycloalkoxy, wherein the $C_1$-$C_6$ alkyl is optionally substituted with 1-5 halo; and
p is 0, 1, 2 or 3.

In some embodiments, the compound is of Formula IIIB, IIIC, or IIID:

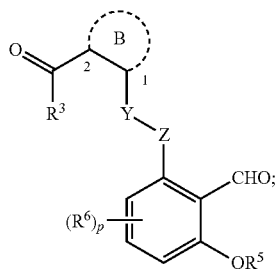

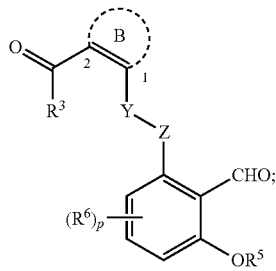

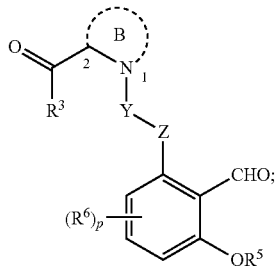

wherein

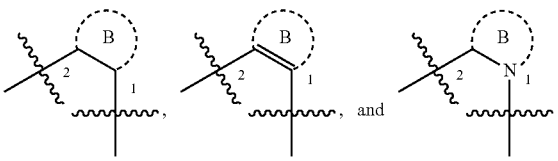

are optionally substituted 4-10 membered heterocycle as defined herein;

$R^5$ is hydrogen, $C_1$-$C_6$ alkyl or a prodrug moiety;

$R^6$ is halo, $C_1$-$C_6$ alkyl, $C_1$-$C_6$ alkoxy, wherein the $C_1$-$C_6$ alkyl is optionally substituted with 1-5 halo; and p is 0, 1, 2 or 3.

In some embodiments, ring B is substituted with 1-3: halo, $C_1$-$C_6$ alkyl, $COR^{15}$, or $COOR^{15}$; and $R^{15}$ is $C_1$-$C_6$ alkyl, $C_3$-$C_6$ cycloalkyl, $C_6$-$C_{10}$ aryl, 5-10 membered heteroaryl or a 4-10 membered heterocycle containing up to 5 ring heteroatoms, wherein the heteroatom is selected from the group consisting of O, N, S, and oxidized forms of N and S, wherein the alkyl, aryl, heteroaryl or heterocyclyl is optionally substituted.

In certain aspects of the invention, a compound of formula (IV) is provided:

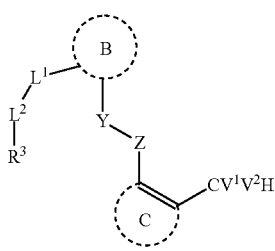

(IV)

or a tautomer thereof, or a pharmaceutically acceptable salt of each thereof, wherein $R^3$ is $C_6$-$C_{10}$ aryl, or a 5-10 membered heteroaryl, wherein the heteroatom is selected from the group consisting of O, N, S, and oxidized forms of N and S, wherein each of the aryl, or heteroaryl is optionally substituted with 1-4 $C_1$-$C_6$ alkyl;

$L^1$ is a bond or is $NR^{70}$, O, S, or $(CR^{71}R^{72})_d$; wherein each $R^{70}$, $R^{71}$, and $R^{72}$ independently are hydrogen or $C_1$-$C_6$ alkyl;

d is 1, 2, or 3;

$L^2$ is C=O or $SO_2$;

ring B is a optionally substituted 4-10 membered heterocycle containing up to 5 ring heteroatoms, wherein the heteroatom is selected from the group consisting of O, N, S, and oxidized forms of N and S;

each Y and Z is independently $CR^{10}R^{11}$, O, S, SO, $SO_2$, or $NR^{10}$; each $R^{10}$ and $R^{11}$ independently is hydrogen or $C_1$-$C_3$ alkyl optionally substituted with 1-3 halo, OH, or $C_1$-$C_6$ alkoxy, or $CR^{10}R^{11}$ is C=O, provided that if one of Y and Z is O, S, SO, $SO_2$, then the other is not CO, and Y and Z are both not heteroatoms or oxidized forms thereof;

wherein Y is α or β substituted relative to the -$L^1L^2R^1$;

ring C is $C_6$-$C_{10}$ aryl or a 5-10 membered heteroaryl containing up to 5 ring heteroatoms, wherein the heteroatom is selected from the group consisting of O, N, S, and oxidized forms of N and S, each of which is optionally substituted with 1-4: halo, oxo, —$OR^{19}$, $C_1$-$C_6$ alkyl, and/or $C_1$-$C_6$ alkoxy, wherein the $C_1$-$C_6$ alkyl is optionally substituted with 1-5 halo, $C_1$-$C_6$ alkoxy and/or a 4-10 membered heterocycle containing up to 5 ring heteroatoms, wherein the heteroatom is selected from the group consisting of O, N, S, and oxidized forms of N and S;

$R^{19}$ is hydrogen or a prodrug moiety R; and wherein Z and —$CV^1V^2H$ are attached to adjacent atoms on ring C;

$V^1$ and $V^2$ independently are $C_1$-$C_6$ alkoxy; or $V^1$ and $V^2$ together with the carbon atom they are attached to form a ring of formula:

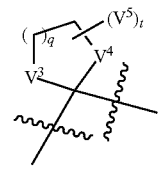

wherein each $V^3$ and $V^4$ are independently O, S, or NH, provided that when one of $V^3$ and $V^4$ is S, the other is NH, and provided that $V^3$ and $V^4$ are both not NH; q is 1 or 2; each $V^5$ is independently $C_1$-$C_6$ alkyl or $CO_2R^{60}$, where each $R^{60}$ independently is $C_1$-$C_6$ alkyl or hydrogen; t is 0, 1, 2, or 4; or $CV^1V^2$ is C=V, wherein V is O, $NOR^{80}$, or $NNR^{81}R^{82}$;

$R^{80}$ is optionally substituted $C_1$-$C_6$ alkyl;

$R^{81}$ and $R^{82}$ independently are selected from the group consisting of hydrogen; optionally substituted $C_1$-$C_6$ alkyl, $COR^{83}$ and $CO_2R^{84}$;

$R^{83}$ is hydrogen or optionally substituted $C_1$-$C_6$ alkyl; and $R^{84}$ is optionally substituted $C_1$-$C_6$ alkyl.

In certain embodiments, Z is $CH_2$, O, S, SO, $SO_2$ or NH. In certain embodiments, Z is O, S, SO or $SO_2$. Preferably, Z is O, and wherein the remaining variables are defined herein.

In certain embodiments, Y is $CR^{10}R^{11}$, O, S, SO, $SO_2$, or $NR^{10}$; wherein each $R^{10}$ and $R^{11}$ independently is hydrogen or $C_1$-$C_3$ alkyl. In certain embodiments, Y is $CR^{10}R^{11}$ wherein each $R^{10}$ and $R^{11}$ independently is hydrogen or $C_1$-$C_3$ alkyl. Preferably, Y is $CH_2$, and wherein the remaining variables are defined herein.

In certain embodiments, t is 0. In certain embodiments, t is 1. In certain embodiments, t is 2. In certain embodiments, t is 3.

Preferably, $CV^1V^2$ is C=V, wherein V is O, and wherein the remaining variables are defined herein.

In certain embodiments, a compound of formula (V) is provided:

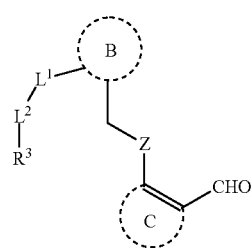

(V)

or a tautomer thereof, or a pharmaceutically acceptable salt of each thereof, wherein $R^3$ is $C_6$-$C_{10}$ aryl, or a 5-10 membered heteroaryl, wherein the heteroatom is selected from the group consisting of O, N, S, and oxidized forms of N and S, wherein each of the aryl, or heteroaryl is optionally substituted with 1-4 $C_1$-$C_6$ alkyl;

$L^1$ is a bond or is $NR^{70}$, O, S, or $(CR^{71}R^{72})_d$; wherein each $R^{70}$, $R^{71}$, and $R^{72}$ independently are hydrogen or $C_1$-$C_6$ alkyl;

d is 1, 2, or 3;

L² is C=O or SO₂;

ring B is a optionally substituted 4-10 membered heterocycle containing up to 5 ring heteroatoms, wherein the heteroatom is selected from the group consisting of O, N, S, and oxidized forms of N and S;

Z is O, S, SO or SO₂;

ring C is $C_6$-$C_{10}$ aryl or a 5-10 membered heteroaryl containing up to 5 ring heteroatoms, wherein the heteroatom is selected from the group consisting of O, N, S, and oxidized forms of N and S, each of which is optionally substituted with 1-4: halo, oxo, —OR¹⁹, $C_1$-$C_6$ alkyl, and/or $C_1$-$C_6$ alkoxy, wherein the $C_1$-$C_6$ alkyl is optionally substituted with 1-5 halo, $C_1$-$C_6$alkoxy and/or a 4-10 membered heterocycle containing up to 5 ring heteroatoms, wherein the heteroatom is selected from the group consisting of O, N, S, and oxidized forms of N and S; and R¹⁹ is hydrogen or a prodrug moiety R.

In certain embodiments, a compound of formula (VI) is provided:

(VI)

or a tautomer thereof, or a pharmaceutically acceptable salt of each thereof, wherein R³ is $C_6$-$C_{10}$ aryl, or a 5-10 membered heteroaryl, wherein the heteroatom is selected from the group consisting of O, N, S, and oxidized forms of N and S, wherein each of the aryl, or heteroaryl is optionally substituted with 1-4 $C_1$-$C_6$ alkyl;

L¹ is a bond or is NR⁷⁰, O, S, or (CR⁷¹R⁷²)$_d$; wherein each R⁷⁰, R⁷¹, and R⁷² independently are hydrogen or $C_1$-$C_6$ alkyl;

d is 1, 2, or 3;

L² is C=O or SO₂;

ring B is a optionally substituted 4-10 membered heterocycle containing up to 5 ring heteroatoms, wherein the heteroatom is selected from the group consisting of O, N, S, and oxidized forms of N and S;

R⁴ is —OR¹⁹ or $C_1$-$C_6$ alkoxy; and

R¹⁹ is hydrogen or a prodrug moiety R.

In one embodiment, R⁴ is —OH.

In certain embodiments, R³ is optionally substituted phenyl. In other embodiments, R³ is optionally substituted pyridine. In certain embodiments, R³ is optionally substituted pyrazole.

In certain embodiments, R³ is selected from the group consisting of:

In certain embodiments, compounds of formulas (IV) and (V) are provided, wherein In one embodiment, ring B is a 5-6 membered heterocycle containing a heteroatom selected from N, S, or O. In one embodiment, ring B is a 5-6 membered heterocycle containing a N as the heteroatom.

In certain embodiments, ring B is selected from the group consisting of:

In certain embodiments, L¹ is a bond.

In certain embodiments, L² is C=O. In certain embodiments, L² is SO₂.

In one embodiment, ring C is phenyl which is optionally substituted with 1-4: halo, oxo, —OR², $C_1$-$C_6$ alkyl and/or $C_1$-$C_6$ alkoxy, In some embodiments, the compound is selected from the group consisting of -continued

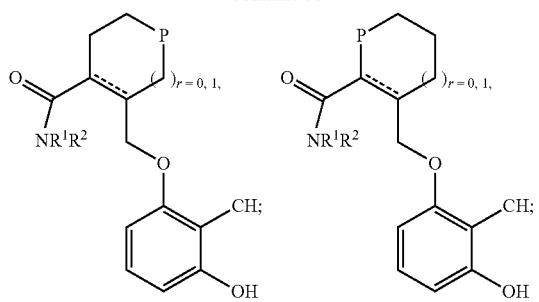

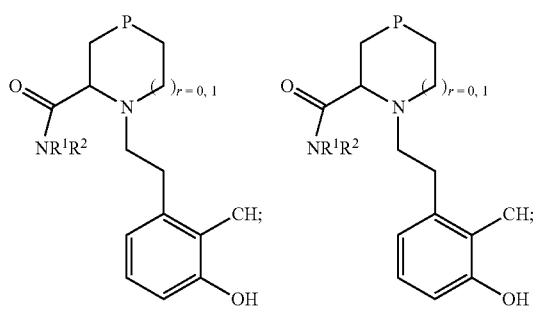

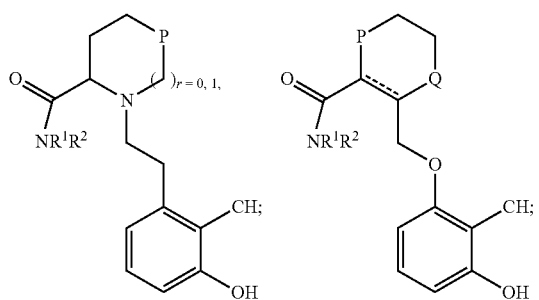

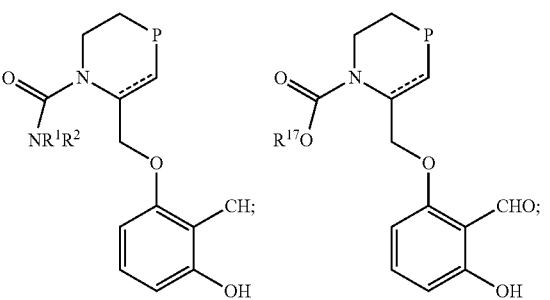

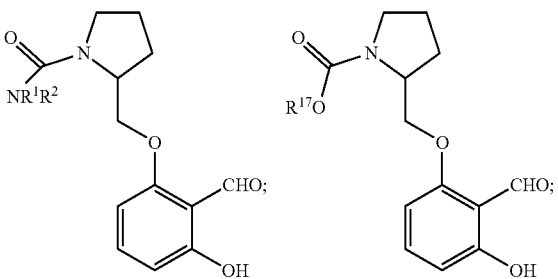

-continued

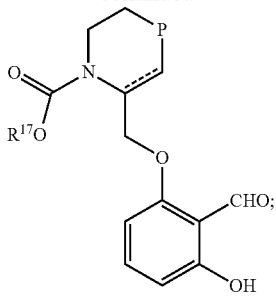

or an N oxide thereof, wherein

⁓ is a single or a double bond;
each P and Q is independently selected from $CHR^{17}$, $NCOR^{15}$, $NCO_2R^{15}$; N—O, O, S, SO, and $SO_2$;
each $R^1$ and $R^2$ independently is hydrogen, $C_1$-$C_6$ alkyl, a $C_6$-$C_{10}$ aryl, 5-10 membered heteroaryl or a 4-10 membered heterocycle containing up to 5 ring heteroatoms, wherein the heteroatom is selected from the group consisting of O, N, S, and oxidized forms of N and S, wherein the alkyl, aryl, heteroaryl or heterocyclyl is optionally substituted, together $R^1$ and $R^2$ can form a 3-7 membered ring, preferably a 4-7 membered ring with 1-2 hetero atoms;
$R^{15}$ is $C_1$-$C_6$ alkyl, $C_6$-$C_{10}$ aryl, 5-10 membered heteroaryl or a 4-10 membered heterocycle containing up to 5 ring heteroatoms, wherein the heteroatom is selected from the group consisting of O, N, S, and oxidized forms of N and S, wherein the alkyl, aryl, heteroaryl or heterocyclyl is optionally substituted;
$R^{17}$ is $C_1$-$C_6$ alkyl, $C_6$-$C_{10}$ aryl, 5-10 membered heteroaryl or a 4-10 membered heterocycle containing up to 5 ring heteroatoms, wherein the heteroatom is selected from the group consisting of O, N, S, and oxidized forms of N and S, wherein the alkyl, aryl, heteroaryl or heterocyclyl is optionally substituted;
and r is 0, 1, or 2.

In certain embodiments of the invention, a compound is provided of formula:

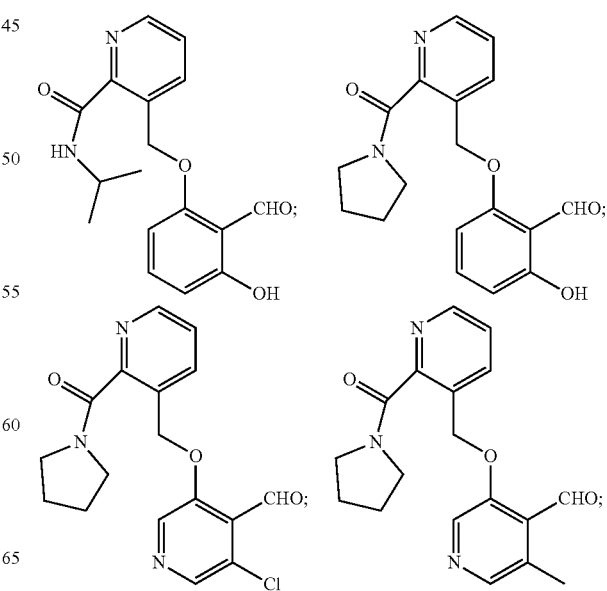

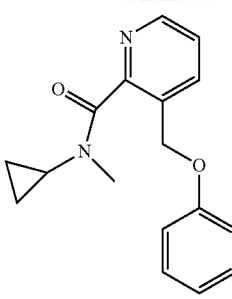
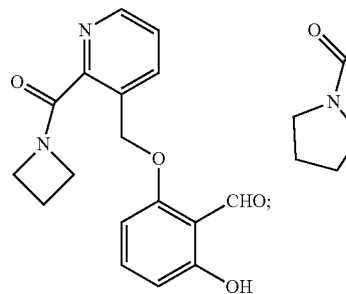
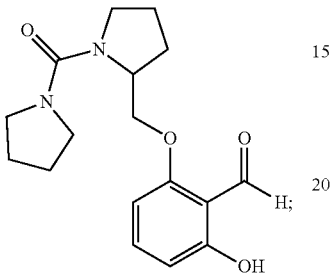
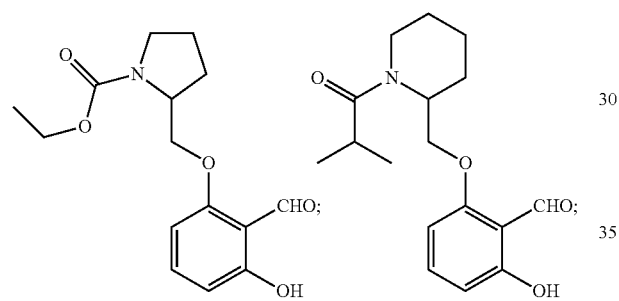
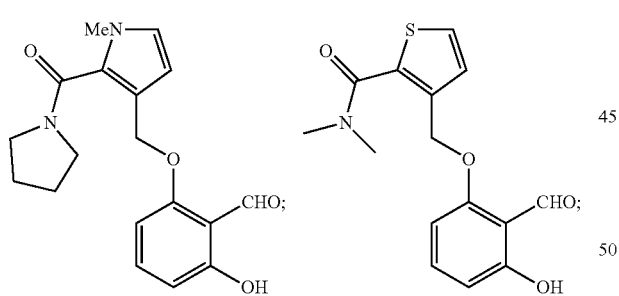
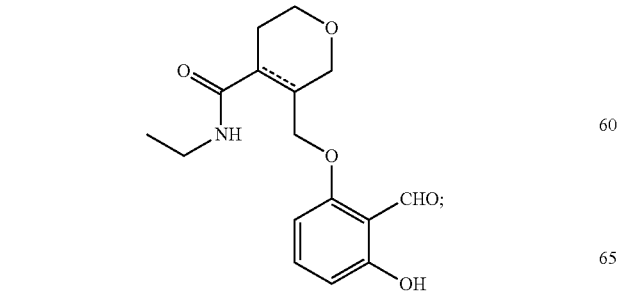
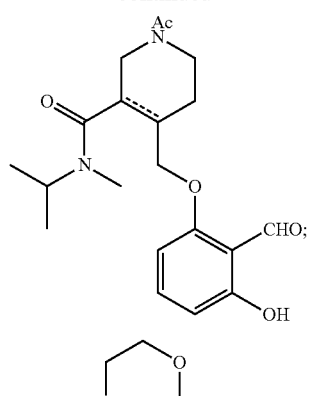
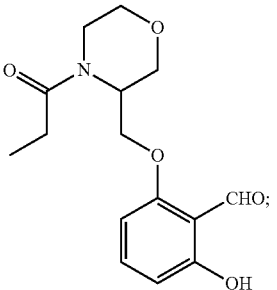
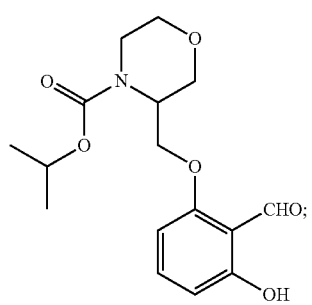
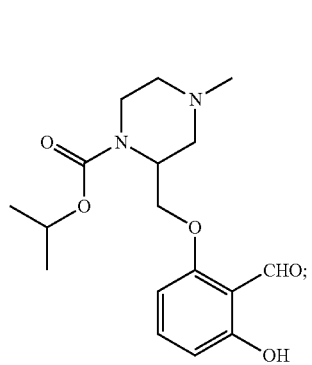
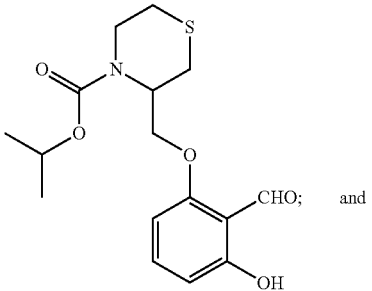

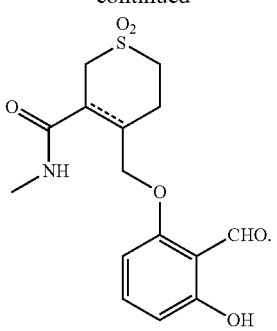
or an N oxide thereof, or a pharmaceutically acceptable salt of each thereof.
In certain embodiments of the invention, a compound is provided of formula:
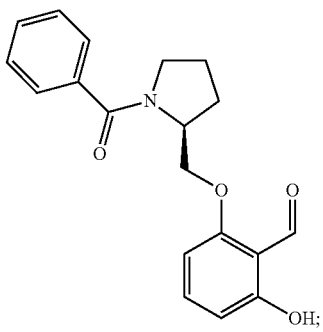
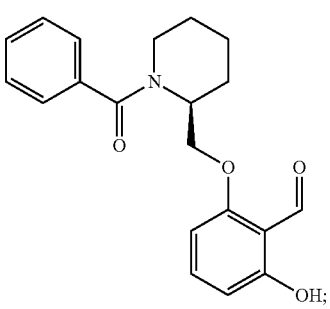
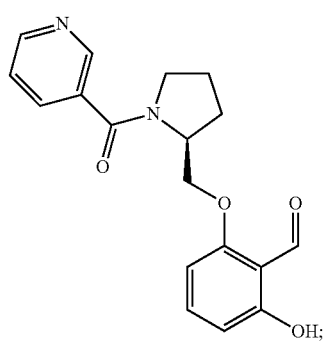
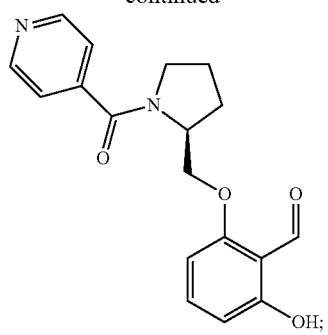
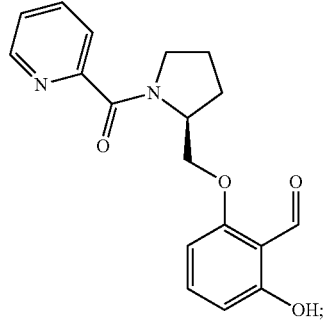
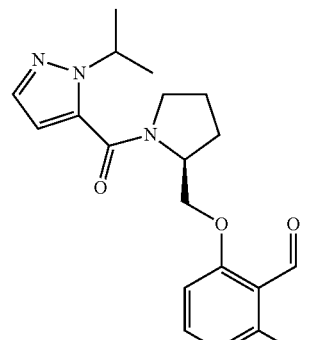
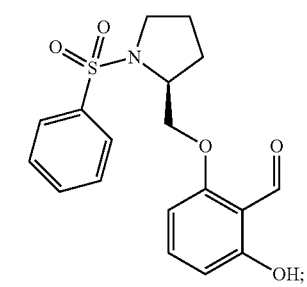
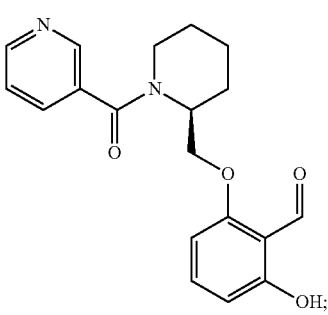

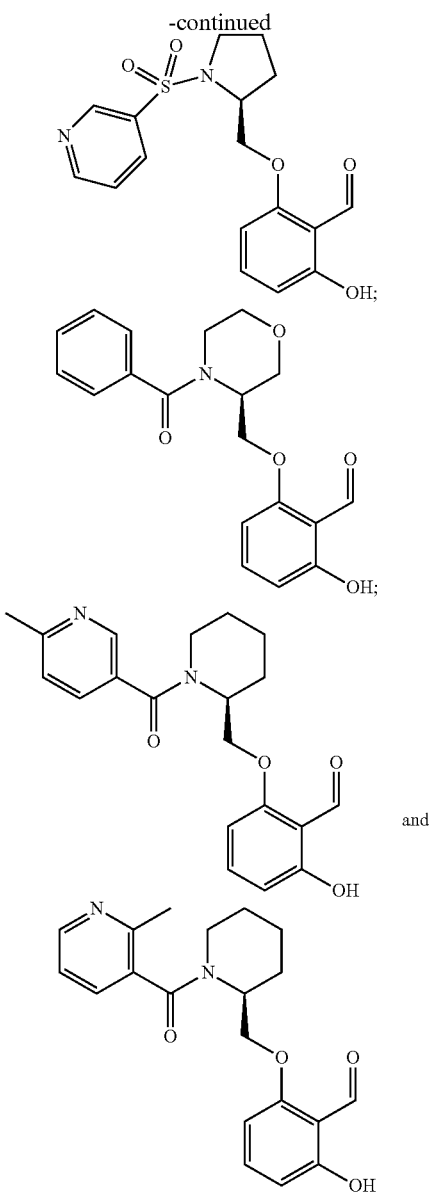

and or an N oxide thereof, or a pharmaceutically acceptable salt of each thereof.

Compounds provided herein include those in the Examples section.

Prodrug Moiety

In one aspect, R is hydrogen, a phosphate or a diphosphate containing moiety, or another promoiety or prodrug moiety. Preferably the prodrug moiety imparts at least a 2 fold, more preferably a 4 fold, enhanced solubility and/or bioavailability to the active moiety (where R is hydrogen), and more preferably is hydrolyzed in vivo. The promoieties are structurally and functionally defined herein.

In one embodiments, R is —$COR^{90}$, $CO_2R^{91}$, or $CONR^{92}R^{93}$ wherein $R^{90}$ and $R^{91}$ independently are $C_1$-$C_6$ alkyl, $C_3$-$C_8$ cycloalkyl, 4-9 membered heterocycle, or a 5-10 membered heteroaryl, each containing at least 1 basic nitrogen moiety; and $R^{92}$ and $R^{93}$ independently are $C_1$-$C_6$ alkyl; $C_3$-$C_8$ cycloalkyl, 4-9 membered heterocycle, or a 5-10 membered heteroaryl, each containing at least 1 basic nitrogen moiety; or $R^{92}$ and $R^{93}$ together with the nitrogen atom they are bonded to for a 4-9 member heterocycle substituted with at least 1 amino, $C_1$-$C_6$ alkyl amino, or di $C_1$-$C_6$ alkylamino group.

In certain embodiments, R is —$C(O)R^{31}$, $C(O)OR^{31}$, or $CON(R^{13})_2$;

each $R^{31}$ is independently a $C_1$-$C_6$ alkyl; $C_3$-$C_8$ cycloalkyl, 4-9 membered heterocycle, or a 5-10 membered heteroaryl, containing at least 1 basic nitrogen moiety; and each $R^{13}$ independently is $C_1$-$C_6$ alkyl; $C_3$-$C_8$ cycloalkyl, 4-9 membered heterocycle, or a 5-10 membered heteroaryl, containing at least 1 basic nitrogen moiety; or 2 $R^{13}$ together with the nitrogen atom they are bonded to for a 4-9 member heterocycle substituted with at least 1 amino, $C_1$-$C_6$ alkyl amino, or di $C_1$-$C_6$ alkylamino group.

In one aspect, R is $C(O)OR^{31}$, $C(S)OR^{31}$, $C(O)SR^{31}$ or $COR^{31}$, wherein $R^{31}$ is as defined herein.

In one embodiment, $R^{31}$ is a group of the formula $(CR^{32}R^{33})_e NR^{34}R^{35}$, wherein each $R^{32}$ and $R^{33}$ is independently H, a $C_1$-$C_8$ alkyl, $C_3$-$C_9$ heterocyclyl, $C_3$-$C_8$ cycloalkyl, $C_6$-$C_{10}$ aryl, $C_3$-$C_9$ heteroaryl or $R^{32}$ and $R^{33}$ together with the carbon atom they are bond to form a $C_3$-$C_8$ cycloalkyl, $C_6$-$C_{10}$ aryl, $C_3$-$C_9$ heterocyclyl or $C_3$-$C_9$ heteroaryl ring system, or 2 adjacent $R^{32}$ moieties or 2 adjacent $R^{33}$ moieties together with the carbon atom they are bond to form a $C_3$-$C_8$ cycloalkyl, $C_6$-$C_{10}$ aryl, $C_3$-$C_9$ heterocyclyl or $C_3$-$C_9$ heteroaryl ring system;

each $R^{34}$ and $R^{35}$ is a $C_1$-$C_8$ alkyl, $C_3$-$C_9$ heterocyclyl, $C_3$-$C_8$ cycloalkyl, or $R^{34}$ and $R^{35}$ together with the nitrogen atom they are bond to form a $C_3$-$C_8$ cycloalkyl or $C_3$-$C_9$ heterocyclyl ring system;

each heterocyclic and heteroaryl ring system is optionally substituted with $C_1$-$C_3$ alkyl, —OH, amino and carboxyl groups; and e is an integer of from 1 to 4.

In some less preferred embodiments $R^{34}$ and $R^{35}$ can be hydrogen.

In one embodiment, the subscript e is preferably 2 and each $R^{32}$ and $R^{33}$ is preferably independently selected from the group, H, $CH_3$, and a member in which $R^{32}$ and $R^{33}$ are joined together to form a cyclopropyl, cyclobutyl, cyclopentyl, cyclohexyl, or 1,1-dioxo-hexahydro-I$\Delta^6$-thiopyran-4-yl or tetrahydropyran-4-yl group.

With regard to the prodrug group, preferred embodiments are compounds wherein $NR^{34}R^{35}$ is morpholino.

In one embodiment, R is:

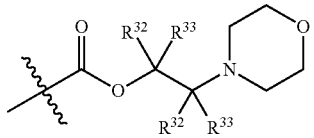

wherein each $R^{32}$ and $R^{33}$ is independently H, $C_1$-$C_8$ alkyl, or optionally, if both present on the same substituent, may be joined together to form a $C_3$-$C_8$ cycloalkyl, $C_6$-$C_{10}$ aryl, $C_3$-$C_9$ heterocyclyl or $C_3$-$C_9$ heteroaryl ring system.

Within this embodiment, each $R^{32}$ and $R^{33}$ is independently, H, $CH_3$, or are joined together to form a cyclopropyl, cyclopbutyl, cyclopentyl, cyclohexyl, 1,1-dioxo-hexahydro-I$\lambda^6$-thiopyran-4-yl or tetrahydropyran-4-yl group.

In a preferred embodiment, linkage of the prodrug moiety to the rest of the active molecule is stable enough so that the serum half life of the prodrug is from about 8 to about 24 hours.

In an embodiment of the invention, the prodrug moiety comprises a tertiary amine having a pKa near the physiological pH of 7.5. Any amines having a pKa within 1 unit of 7.5 are suitable alternatives amines for this purpose. The amine may be provided by the amine of a morpholino group. This pKa range of 6.5 to 8.5 allows for significant concentrations of the basic neutral amine to be present in the mildly alkaline small intestine. The basic, neutral form of the amine prodrug is lipophilic and is absorbed through the wall of the small intestine into the blood. Following absorption into the bloodstream, the prodrug moiety is cleaved by esterases which are naturally present in the serum to release an active compound.

Examples of R include, without limitation:

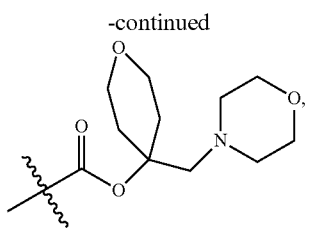

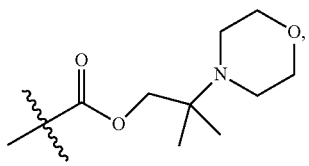

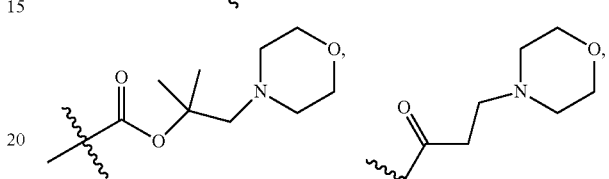

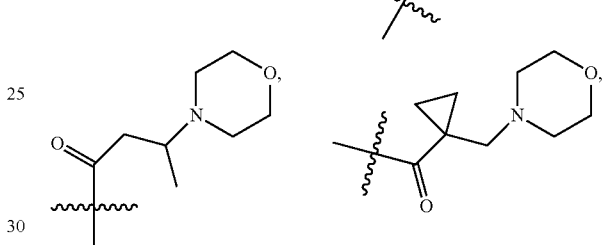

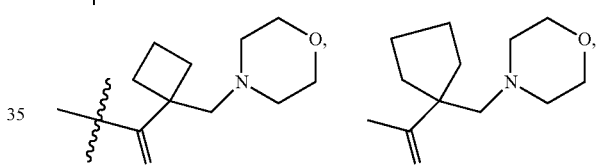

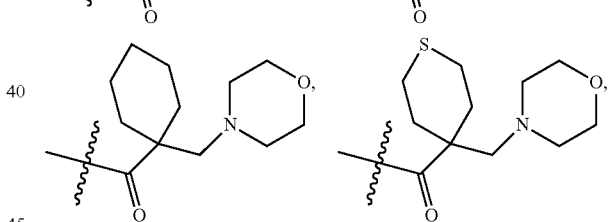

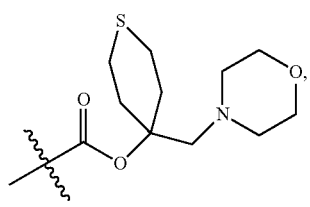

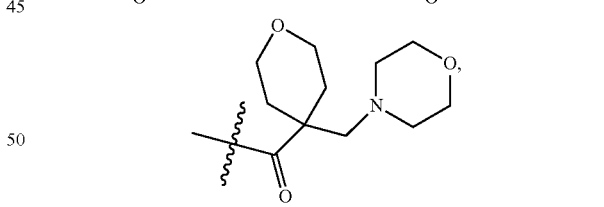

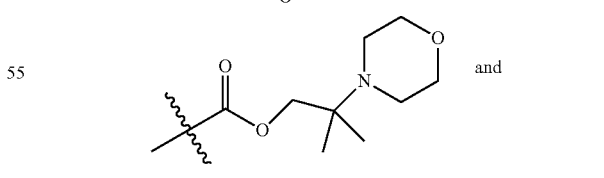

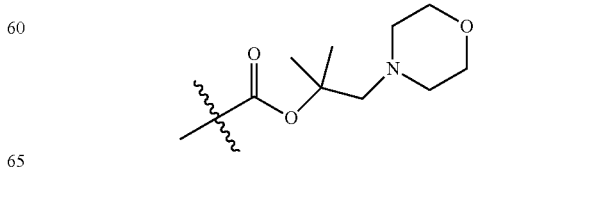

In another embodiment, R is as tabulated below:

| R | m | $R^{34}$ | $R^{35}$ | $NR^{34}R^{35}$ |
|---|---|---|---|---|
| $C(O)(CH_2)_m NR^{34}R^{35}$ | 1 | Me | Me | |
| $C(O)(CH_2)_m NR^{34}R^{35}$ | 2 | Me | Me | |
| $C(O)(CH_2)_m NR^{34}R^{35}$ | 3 | Me | Me | |
| $C(O)(CH_2)_m NR^{34}R^{35}$ | 4 | Me | Me | |
| $C(O)(CH_2)_m NR^{34}R^{35}$ | 1 | | | 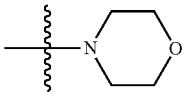 |
| $C(O)(CH_2)_m NR^{34}R^{35}$ | 2 | | | 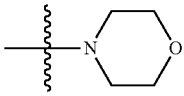 |
| $C(O)(CH_2)_m NR^{34}R^{35}$ | 3 | | | 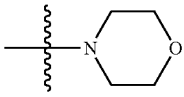 |
| $C(O)(CH_2)_m NR^{34}R^{35}$ | 4 | | | 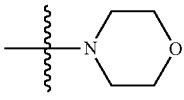 [SMILES: *N1CCOCC1] |
| $C(O)O(CH_2)_m NR^{34}R^{35}$ | 2 | Me | Me | |
| $C(O)O(CH_2)_m NR^{34}R^{35}$ | 3 | Me | Me | |
| $C(O)O(CH_2)_m NR^{34}R^{35}$ | 4 | Me | Me | |
| $C(O)O(CH_2)_m NR^{34}R^{35}$ | 2 | | | 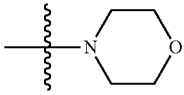 |
| $C(O)O(CH_2)_m NR^{34}R^{35}$ | 3 | | | 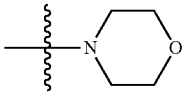 |
| $C(O)O(CH_2)_m NR^{34}R^{35}$ | 4 | | | 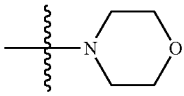 |
| $P(O)(OH)_2$ | | | | | an N oxide thereof, or a pharmaceutically acceptable salt of each thereof.

In another aspect, R is,

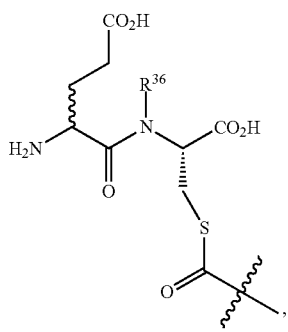

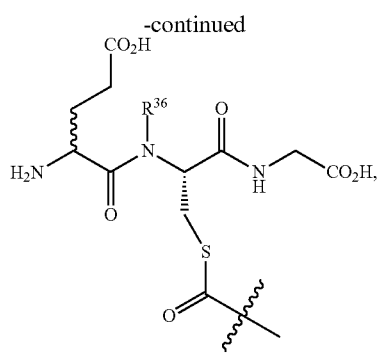

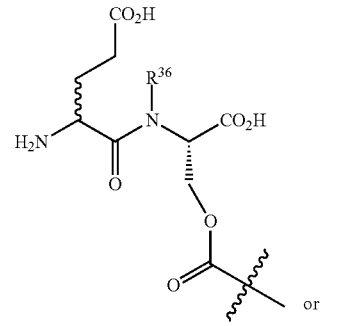

or

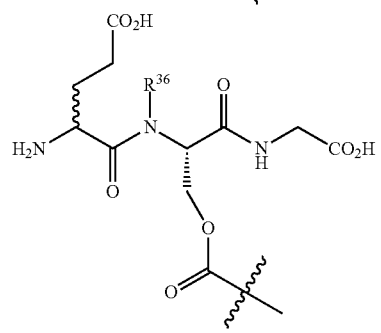

wherein $R^{36}$ is lower alkyl (e.g. $C_1$-$C_6$ alkyl).

In yet another aspect, R is:

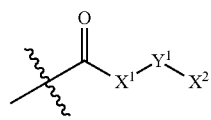

wherein $X^1$, $Y^1$ and $X^2$ are as defined herein.

In one embodiment, $X^1$ is selected from the group consisting of O, S and $NR^{37}$ wherein $R^{37}$ is hydrogen or $C_1$-$C_6$ alkyl;

$Y^1$ is —$C(R^{38})_2$— or a sugar moiety, wherein each $R^{38}$ is independently hydrogen or $C_1$-$C_6$ alkyl, $C_3$-$C_8$ cycloalkyl, $C_3$-$C_9$ heterocyclyl, $C_6$-$C_{10}$ aryl, or $C_3$-$C_9$ heteroaryl;

$X^2$ is selected from the group consisting of halogen, $C_1$-$C_6$ alkoxy, diacylglycerol, amino, $C_1$-$C_6$ alkylamino, $C_1$-$C_6$ dialkylamino, $C_1$-$C_6$ alkylthio, a PEG moiety, a bile acid moiety, a sugar moiety, an amino acid moiety, a di- or tri-peptide, a PEG carboxylic acid, and —U—V wherein U is O or S; and V is selected from the group consisting of $C_1$-$C_6$ alkyl, $C_3$-$C_8$ cycloalkyl, $C_3$-$C_9$ heterocyclyl, $C_6$-$C_{10}$ aryl, $C_3$-$C_9$ heteroaryl, $C(W^2)X^3$, $PO(X^3)_2$, and $SO_2X^3$;

wherein $W^2$ is O or $NR^{39}$ wherein $R^{39}$ is hydrogen or $C_1$-$C_6$ alkyl, $C_3$-$C_8$ cycloalkyl, $C_3$-$C_9$ heterocyclyl, $C_6$-$C_{10}$ aryl, or $C_3$-$C_9$ heteroaryl; and each $X^3$ is independently amino, hydroxyl, mercapto, $C_1$-$C_6$ alkyl, heteroalkyl, cycloalkyl, heterocyclyl, aryl, or heteroaryl, $C_1$-$C_6$ alkoxy, $C_1$-$C_6$ alkylamino, $C_1$-$C_6$ dialkylamino, $C_1$-$C_6$ alkylthio, a bile acid based alkoxy group, a sugar moiety, a PEG moiety, and —O—$CH_2$—$CH(OR^{40})$$CH_2X^4R^{40}$, wherein:

$X^4$ is selected from the group consisting of O, S, S=O, and $SO_2$; and each $R^{40}$ is independently $C_{10}$-$C_{22}$ alkyl, $C_3$-$C_8$ cycloalkyl, $C_3$-$C_9$ heterocyclyl, $C_6$-$C_{10}$ aryl, or $C_3$-$C_9$ heteroaryl, $C_1$-$C_8$ alkylene, or $C_1$-$C_8$ heteroalkylene.

Each heterocyclic and heteroaryl ring system is optionally substituted with $C_1$-$C_3$ alkyl, —OH, amino and carboxyl groups.

In one embodiment, the present invention utilizes the following $Y^1$ groups: $CH_2$, CHMe, CH(isopropyl), CH(tertiarybutyl), $C(Me)_2$, $C(Et)_2$, $C(isopropyl)_2$, and $C(propyl)_2$.

In another embodiment, the present invention utilizes the following $X^2$ groups:

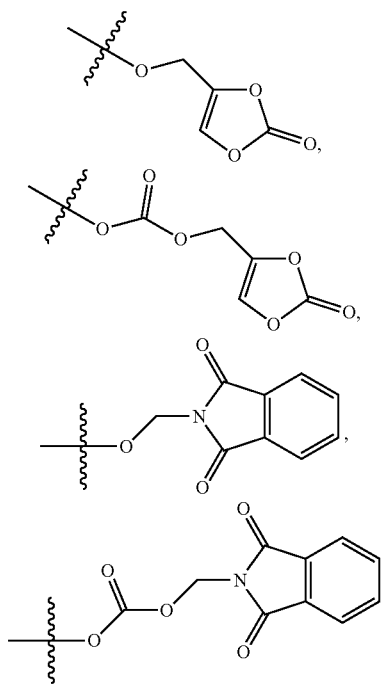

—OMe, —OEt, —O-isopropyl, 0-isobutyl, 0-tertiarybutyl, —O—COMe, —O—C(=O)(isopropyl), —O—C(=O)(isobutyl), —O—C(=O)(tertiarybutyl), —O—C(=O)—$NMe_2$, —O—C(=O)—NHMe, —O—C(=O)—$NH_2$, —O—C(=O)—N(H)—$CH(R^{41})$—$CO_2Et$ wherein $R^{41}$ is a side chain $C_1$-$C_6$ alkyl, or $C_3$-$C_9$ heterocyclyl group selected from the side chain groups present in essential amino acids; —O—P(=O)$(OMe)_2$, —O—P(=O)$(O$-isopropyl$)_2$, and —O—P(=O)$(O$-isobutyl$)_2$. Each heterocyclic is optionally substituted with one or more, preferably, 1-3, $C_1$-$C_3$ alkyl, —OH, amino and/or carboxyl groups.

In another embodiment, In one embodiment, R is:

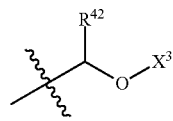

wherein $X^3$ is independently $C_1$-$C_6$ alkyl, $C_3$-$C_8$ cycloalkyl, $C_3$-$C_9$ heterocyclyl, $C_6$-$C_{10}$ aryl, or $C_3$-$C_9$ heteroaryl; and $R^{42}$ is independently hydrogen or $C_1$-$C_6$ alkyl, $C_3$-$C_8$ cycloalkyl, $C_3$-$C_9$ heterocyclyl, $C_6$-$C_{10}$ aryl, or $C_3$-$C_9$ heteroaryl.

Each heterocyclic is optionally substituted with one or more, preferably, 1-3, $C_1$-$C_3$ alkyl, —OH, amino and/or carboxyl groups.

In one embodiment, R is:

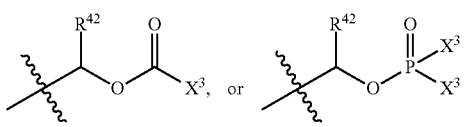

wherein each $X^3$ is independently amino, hydroxyl, mercapto, $C_1$-$C_6$ alkyl, $C_3$-$C_8$ cycloalkyl, $C_3$-$C_9$ heterocyclyl, $C_6$-$C_{10}$ aryl, or $C_3$-$C_9$ heteroaryl, $C_1$-$C_6$ alkoxy, $C_1$-$C_6$ alkylamino, $C_1$-$C_6$ dialkylamino, $C_1$-$C_6$ alkylthio, a bile acid based alkoxy group, a sugar moiety, a PEG moiety, and —O—$CH_2$—$CH(OR^{40})CH_2X^4R^{40}$, wherein:

$X^4$ is selected from the group consisting of O, S, S=O, and $SO_2$; and each $R^{40}$ is independently $C_{10}$-$C_{22}$ alkyl, $C_3$-$C_8$ cycloalkyl, $C_3$-$C_9$ heterocyclyl, $C_6$-$C_{10}$ aryl, $C_3$-$C_9$ heteroaryl, $C_1$-$C_8$ alkylene, or $C_1$-$C_8$ heteroalkylene; and $R^{42}$ is independently hydrogen or $C_1$-$C_6$ alkyl, $C_3$-$C_8$ cycloalkyl, $C_3$-$C_9$ heterocyclyl, $C_6$-$C_{10}$ aryl, or $C_3$-$C_9$ heteroaryl.

In some embodiments, $R^{42}$ is independently hydrogen or $C_1$-$C_6$ alkyl, $C_3$-$C_8$ cycloalkyl, $C_3$-$C_9$ heterocyclyl, $C_6$-$C_{10}$ aryl, or $C_3$-$C_9$ heteroaryl; and each $X^3$ independently is $C_1$-$C_6$ alkyl, $C_3$-$C_8$ cycloalkyl, $C_3$-$C_9$ heterocyclyl, $C_6$-$C_{10}$ aryl, or $C_3$-$C_9$ heteroaryl, $C_1$-$C_6$ alkoxy, $C_1$-$C_6$ alkylamino, $C_1$-$C_6$ dialkylamino, or $C_1$-$C_6$ alkylthio.

In some embodiments, R is represented by the following structures:

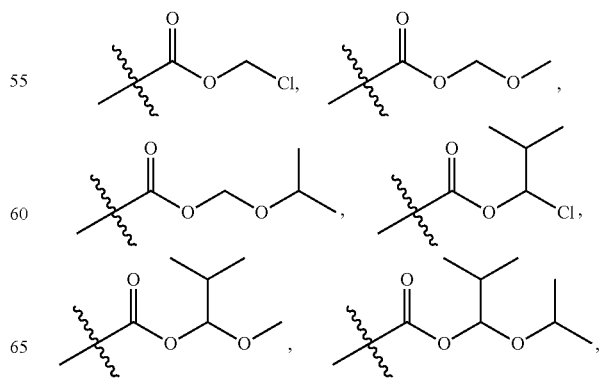

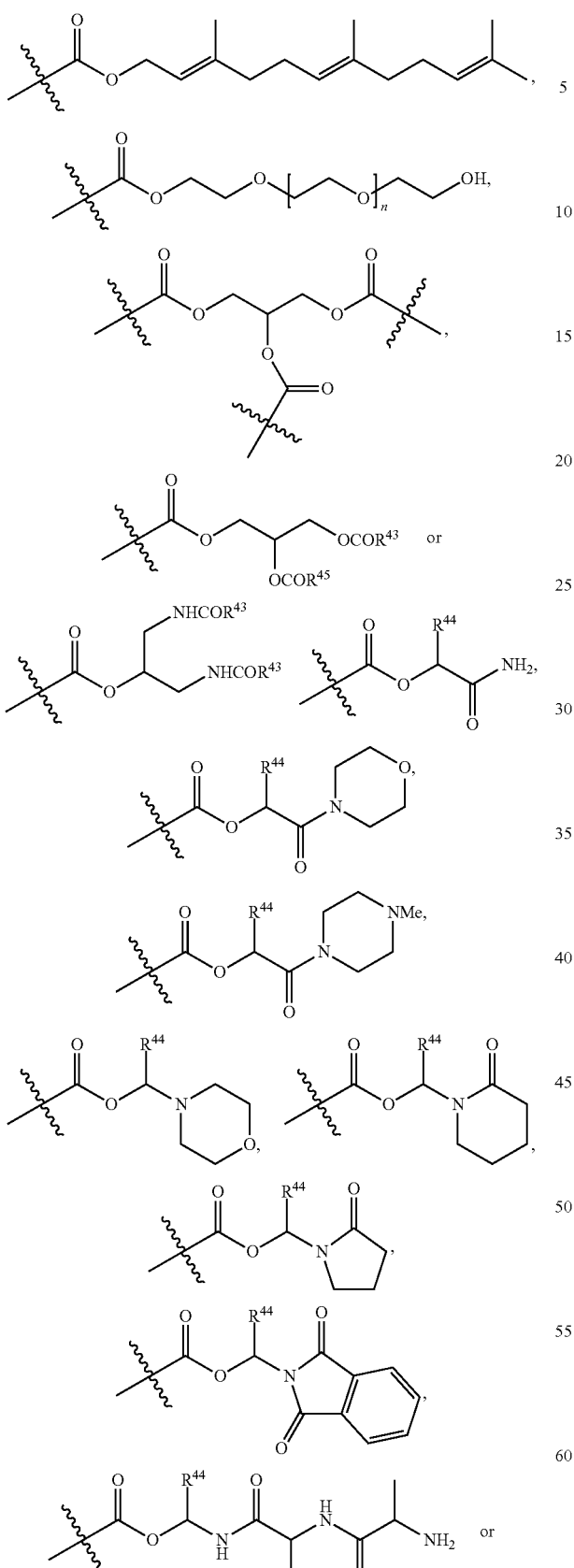
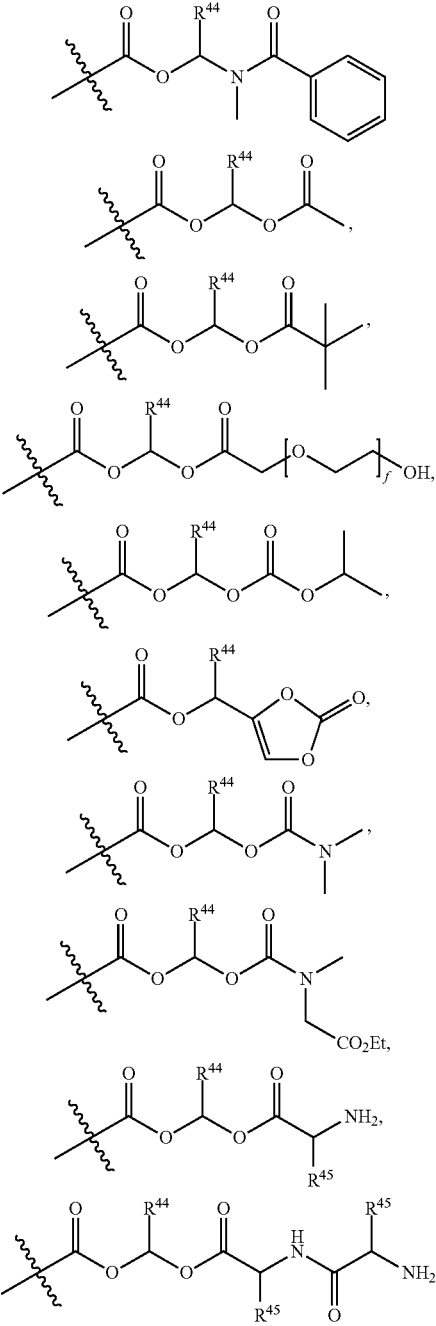
wherein, in the above examples, $R^{43}$ is $C_{10}$-$C_{22}$ alkyl or alkylene, $R^{44}$ is H or $C_1$-$C_6$ alkyl and $R^{45}$ represents side chain alkyl groups present in naturally occurring alpha amino acids;
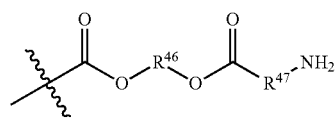
wherein $R^{46}$ is $(CH_2)_n$, f=2-4, and CO—$R^{47}$—$NH_2$ represents an aminoacyl group; or

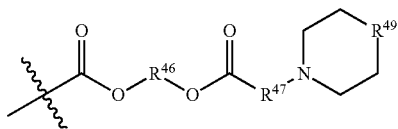

wherein $R^{46}$ is $(CH_2)_n$, n=2-4, $R^{47}$ is $(CH_2)_n$, n=1-3 and $R^{49}$ is O or NMe.

In one embodiment, R is:

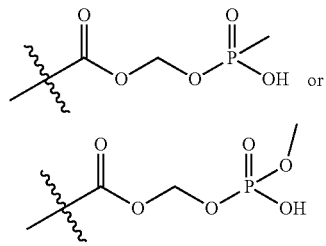

In one aspect, R is —C($R^{200}R^{201}$)O($R^{202}R^{203}$)P(O)O$R^{204}$N$R^{205}R^{206}$, wherein each $R^{200}$, $R^{201}$, $R^{202}$, $R^{203}$, $R^{204}$, $R^{205}$ and $R^{206}$ is independently H, a $C_1$-$C_8$ alkyl, $C_3$-$C_9$ heterocyclyl, $C_3$-$C_8$ cycloalkyl, $C_6$-$C_{10}$ aryl, $C_3$-$C_9$ heteroaryl, wherein each alkyl, heterocyclyl, cycloalkyl, aryl, and heteroaryl is optionally substituted.

In some embodiments, R is —CH($R^{201}$)OCH$_2$P(O)O$R^{204}$NH$R^{206}$, wherein $R^{201}$ is $C_1$-$C_8$ alkyl, $R^{204}$ is phenyl, optionally substituted. In one embodiment, $R^{206}$ is —CH$R^{207}$C(O)O$R^{208}$ wherein $R^{207}$ is selected from the group consisting of the naturally occurring amino acid side chains and —CO$_2$H esters thereof and $R^{208}$ is $C_1$-$C_8$ alkyl. In one embodiment, $R^{206}$ is $C_1$-$C_6$ alkyl, optionally substituted with 1-3, CO$_2$H, SH, NH$_2$, $C_6$-$C_{10}$ aryl, and $C_2$-$C_{10}$ heteroaryl.

In one embodiment, R is:

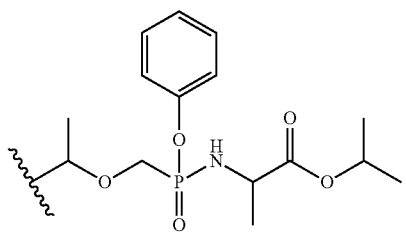 [SMILES: *C(C)OCP(=O)(NC(C)C(=O)OC(C)C)Oc1ccccc1]

In one embodiment, R is:

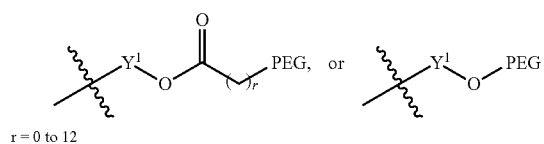

r = 0 to 12 wherein $Y^1$ is —C($R^{38}$)$_2$, wherein each $R^{38}$ is independently hydrogen or $C_1$-$C_6$ alkyl, $C_3$-$C_8$ cycloalkyl, $C_3$-$C_9$ heterocyclyl, $C_6$-$C_{10}$ aryl, or $C_3$-$C_9$ heteroaryl.

Various polyethylene glycol (PEG) moieties and synthetic methods related to them that can be used or adapted to make compounds of the invention are described in U.S. Pat. Nos. 6,608,076; 6,395,266; 6,194,580; 6,153,655; 6,127,355; 6,111,107; 5,965,566; 5,880,131; 5,840,900; 6,011,042 and 5,681,567.

In one embodiment, R is

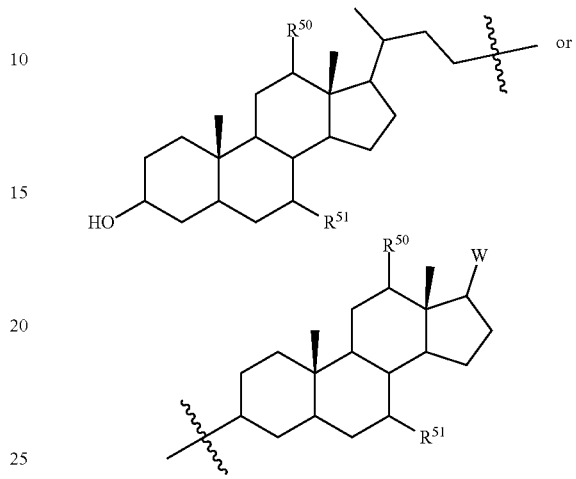

wherein $R^{50}$ is —OH or hydrogen;

$R^{51}$ is —OH, or hydrogen;

W is —CH(CH$_3$)W$^1$;

wherein W$^1$ is a substituted $C_1$-$C_8$ alkyl group containing a moiety which is optionally negatively charged at physiological pH, said moiety is selected from the group consisting of CO$_2$H, SO$_3$H, SO$_2$H, —P(O)(OR$^{52}$)(OH), —OP(O)(OR$^{52}$)(OH), and OSO$_3$H, wherein $R^{52}$ is $C_1$-$C_6$ alkyl, $C_3$-$C_8$ cycloalkyl, $C_3$-$C_9$ heterocyclyl, $C_6$-$C_{10}$ aryl, or $C_3$-$C_9$ heteroaryl.

Each heterocyclic and heteroaryl ring system is optionally substituted with one or more, preferably 1-3, $C_1$-$C_3$ alkyl, —OH, amino and/or carboxyl groups.

In one embodiment, R is:

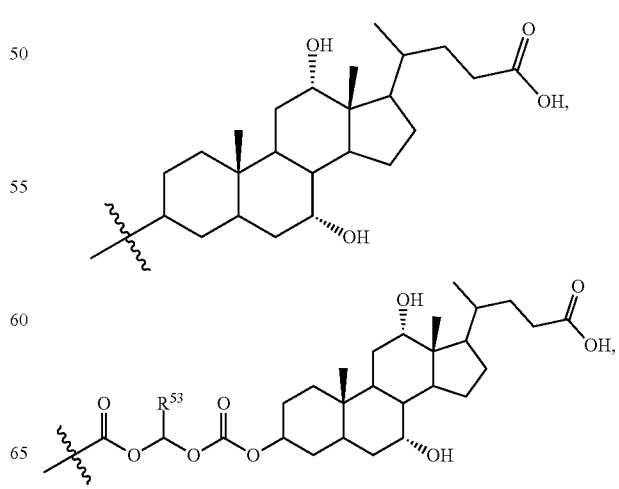

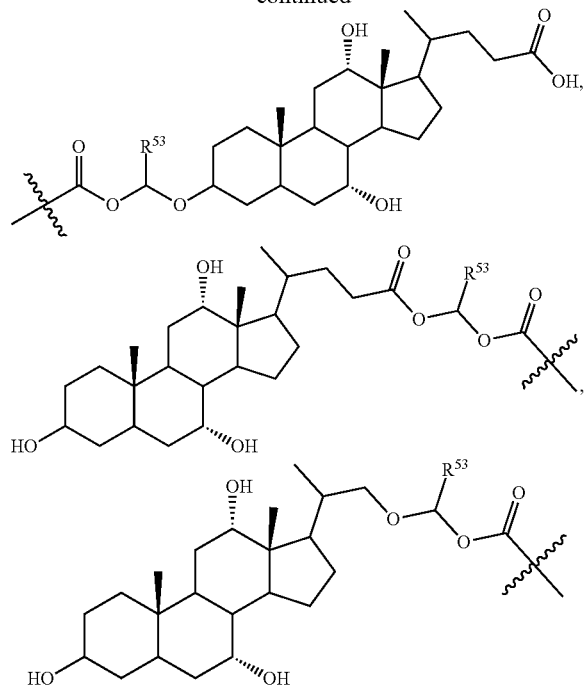

wherein R⁵³ is H or $C_1$-$C_6$ alkyl.

In another aspect, R is $SO_3H$.

In another aspect, R comprises a cleavable linker, wherein the term "cleavable linker" refers to a linker which has a short half life in vivo. The breakdown of the linker Z in a compound releases or generates the active compound. In one embodiment, the cleavable linker has a half life of less than ten hours. In one embodiment, the cleavable linker has a half life of less than an hour. In one embodiment, the half life of the cleavable linker is between one and fifteen minutes. In one embodiment, the cleavable linker has at least one connection with the structure: C*—C(=X*)X*—C* wherein C* is a substituted or unsubstituted methylene group, and X* is S or O. In one embodiment, the cleavable linker has at least one C*—C(=O)O—C* connection. In one embodiment, the cleavable linker has at least one C*—C(=O)S—C* connection. In one embodiment, the cleavable linker has at least one —C(=O)N*—C*—SO₂—N*-connection, wherein N* is —NH— or $C_1$-$C_6$ alkylamino. In one embodiment, the cleavable linker is hydrolyzed by an esterase enzyme.

In one embodiment, the linker is a self-immolating linker, such as that disclosed in U.S. patent publication 2002/0147138, to Firestone; PCT Appl. No. US05/08161 and PCT Pub. No. 2004/087075. In another embodiment, the linker is a substrate for enzymes. See generally Rooseboom et al., 2004, Pharmacol. Rev. 56:53-102.

Pharmaceutical Compositions

In further aspects of the invention, a composition is provided comprising any of the compounds described herein, and at least a pharmaceutically acceptable excipient.

In another aspect, this invention provides a composition comprising any of the compounds described herein, and a pharmaceutically acceptable excipient.

Such compositions can be formulated for different routes of administration. Although compositions suitable for oral delivery will probably be used most frequently, other routes that may be used include transdermal, intravenous, intraarterial, pulmonary, rectal, nasal, vaginal, lingual, intramuscular, intraperitoneal, intracutaneous, intracranial, and subcutaneous routes. Suitable dosage forms for administering any of the compounds described herein include tablets, capsules, pills, powders, aerosols, suppositories, parenterals, and oral liquids, including suspensions, solutions and emulsions. Sustained release dosage forms may also be used, for example, in a transdermal patch form. All dosage forms may be prepared using methods that are standard in the art (see e.g., Remington's Pharmaceutical Sciences, 16$^{th}$ ed., A. Oslo editor, Easton Pa. 1980).

Pharmaceutically acceptable excipients are non-toxic, aid administration, and do not adversely affect the therapeutic benefit of the compound of this invention. Such excipients may be any solid, liquid, semi-solid or, in the case of an aerosol composition, gaseous excipient that is generally available to one of skill in the art. Pharmaceutical compositions in accordance with the invention are prepared by conventional means using methods known in the art.

The compositions disclosed herein may be used in conjunction with any of the vehicles and excipients commonly employed in pharmaceutical preparations, e.g., talc, gum arabic, lactose, starch, magnesium stearate, cocoa butter, aqueous or non-aqueous solvents, oils, paraffin derivatives, glycols, etc. Coloring and flavoring agents may also be added to preparations, particularly to those for oral administration. Solutions can be prepared using water or physiologically compatible organic solvents such as ethanol, 1,2-propylene glycol, polyglycols, dimethylsulfoxide, fatty alcohols, triglycerides, partial esters of glycerin and the like.

Solid pharmaceutical excipients include starch, cellulose, hydroxypropyl cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. In certain embodiments, the compositions provided herein comprises one or more of α-tocopherol, gum arabic, and/or hydroxypropyl cellulose.

In one embodiment, this invention provides sustained release formulations such as drug depots or patches comprising an effective amount of a compound provided herein. In another embodiment, the patch further comprises gum Arabic or hydroxypropyl cellulose separately or in combination, in the presence of alpha-tocopherol. Preferably, the hydroxypropyl cellulose has an average MW of from 10,000 to 100,000. In a more preferred embodiment, the hydroxypropyl cellulose has an average MW of from 5,000 to 50,000.

Compounds and pharmaceutical compositions of this invention maybe used alone or in combination with other compounds. When administered with another agent, the co-administration can be in any manner in which the pharmacological effects of both are manifest in the patient at the same time. Thus, co-administration does not require that a single pharmaceutical composition, the same dosage form, or even the same route of administration be used for administration of both the compound of this invention and the other agent or that the two agents be administered at precisely the same time. However, co-administration will be accomplished most conveniently by the same dosage form and the same route of administration, at substantially the same time. Obviously, such administration most advantageously proceeds by delivering both active ingredients simultaneously in a novel pharmaceutical composition in accordance with the present invention.

Methods of Treatment

In aspects of the invention, a method is provided for increasing tissue and/or cellular oxygenation, the method comprising administering to a subject in need thereof a therapeutically effective amount of any of the compounds or compositions described herein.

In aspects of the invention, a method is provided for increasing oxygen affinity of hemoglobin S in a subject, the method comprising administering to a subject in need thereof a therapeutically effective amount of any of the compounds or compositions described herein.

In aspects of the invention, a method is provided for treating a condition associated with oxygen deficiency, the method comprising administering to a subject in need thereof a therapeutically effective amount of any of the compounds or compositions described herein.

In further aspects of the invention, a method is provided for treating oxygen deficiency associated with sickle cell anemia, the method comprising administering to a subject in need thereof a therapeutically effective amount of any of the compounds or compositions described herein.

In further aspects of the invention, a method is provided for treating sickle cell disease, the method comprising administering to a subject in need thereof a therapeutically effective amount of a compound of any of the compounds or compositions described herein. In still further aspects of the invention, a method is provided for treating cancer, a pulmonary disorder, stroke, high altitude sickness, an ulcer, a pressure sore, Alzheimer's disease, acute respiratory disease syndrome, and a wound, the method comprising administering to a subject in need thereof a therapeutically effective amount of a compound of any of the compounds or compositions described herein.

Synthetic Methods

Certain methods for making the compounds described herein are also provided. The reactions are preferably carried out in a suitable inert solvent that will be apparent to the skilled artisan upon reading this disclosure, for a sufficient period of time to ensure substantial completion of the reaction as observed by thin layer chromatography, $^1$H-NMR, etc. If needed to speed up the reaction, the reaction mixture can be heated, as is well known to the skilled artisan. The final and the intermediate compounds are purified, if necessary, by various art known methods such as crystallization, precipitation, column chromatography, and the likes, as will be apparent to the skilled artisan upon reading this disclosure.

An illustrative and non-limiting method for synthesizing a compound of formula (I), is schematically shown below.

In the following Schemes, ⓑ and ⓒ refer to rings B and C as described herein;

L, $R^3$ and $R^{70}$ are as described herein;

$A^5$ and $B^5$ are independently $NR^{14}$, O, S, S(O)x, NBoC, $CH_2$, $CHR^{14}$, $C(R^{14})_2$ provided that when both $A^5$ and $B^5$ are present in a ring, both are not $CH_2$, $CHR^{14}$, $C(R^{14})_2$, and provided that if only a single $A^5$ or $B^5$ is present in a ring, that $A^5$ or $B^5$ is not $CH_2$, $CHR^{14}$, $C(R^{14})_2$;

$R^{14}$ is $C_1$-$C_6$ alkyl, $COR^{15}$ or $COOR^{15}$; wherein $R^{15}$ is optionally substituted $C_1$-$C_6$ alkyl, optionally substituted $C_6$-$C_{10}$ aryl, optionally substituted 5-10 membered heteroaryl containing up to 5 ring heteroatoms, or optionally substituted 4-10 membered heterocycle containing up to 5 ring heteroatoms, wherein the heteroatom is selected from the group consisting of O, N, S, and oxidized forms of N and S;

X, and $X^5$ each represents a leaving group and are independently selected from Cl, Br, and I.

$X^6$ represents CR, N, O, S(O)x; wherein x is 0, 1, or 2;

$Y^5$ represents a leaving group selected from Cl, F, Br, I, $OSO_2R^{71}$ and $OSO_2Ar$;

$R^{71}$ is $C_1$-$C_6$ alkyl;

Ar is phenyl optionally substituted with 1-3 halo and/or $C_1$-$C_4$ alkyl groups;

n is 0, 1, or 2.

Where variables already used in the structures hereinabove are used in the schemes, the context makes it unambiguous as to what the variable refers to.

General Synthetic Schemes

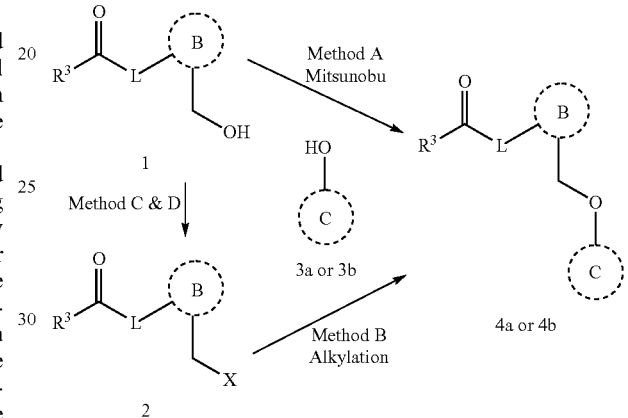

General Method a for Preparing Aryloxy/Heteroarylether Analogs (4a/4b) from substituted methylene alcohol (1) and hydroxyl (hetero)aryl aldehyde derivatives (3a/3b).

A hydroxyl (hetero)arylaldehyde derivatives (3a/3b) (0.1-2 mmol) mixture with substituted methylene alcohol (1) (0.8 to 1.2 eq) and $PPh_3$ (1-1.5 eq) in anhydrous THF (1-10 mL) was stirred under nitrogen until complete dissolution. The solution was cooled to 0° C. on ice bath and DIAD or DEAD (1.1 eq) in THF or toluene was added dropwise over a 1-20 min period. The ice cooling bath was allowed to expire over 90 min and the mixture was stirred at RT for 2-48 hours. The mixture was stirred for 10 min, then filtered through a pad of silica. The silica was washed with ethyl acetate 2-20 mL. The combined filtrates were evaporated and the residue was dried on highvac. The residue was purified by preparative HPLC or flash silica gel chromatography.

General Method B for Preparing Aryloxy/Heteroarylether Analogs (4a/4b) from Substituted Methylene Halide (2) and Hydroxyl (Hetero)Aryl Aldehyde Derivatives (3a/3b).

A mixture of hydroxyl (hetero)arylaldehyde derivatives (3a/3b) (0.1-2 mmol, 1-4 eq.), substituted methylene chloride or bromide (2) (1 eq), and $K_2CO_3$ (2-5 eq.) (catalytic amount of NaI or $Bu_4NI$ may also be added) in DMF or acetonitrile (1 to 10 mL) was stirred at RT or heating up to 120° C. for 0.5-8 h under nitrogen atmosphere. In workup A, water was added to the reaction mixture, the precipitated product was collected, washed with water, and then subjected to preparative HPLC or flash silica gel chromatography purification. In workup B (for products that did not precipitate), diluted HCl or aqueous $NH_4Cl$ was added at 0° C. to adjusted the pH to ~7, the reaction mixture was partitioned between ethyl acetate or dichloromethane and aqueous sodium chloride and the organic layer separated, dried, and solvent removed under vacuum to afford crude product which was purified by automated silica gel column chromatography using appropriate solvents mixture (e.g., ethyl acetate/hexanes).

General Method C for Preparing Substituted Methylene Chloride (2a).

To a solution of substituted methylene alcohol (1) (0.1 to 2 mmol) in DCM (1-10 mL) was added SOCl$_2$ dropwise (2 eq to 5 eq) at 0° C. or RT. The reaction mixture was stirred at RT for 10nnin to 6 h, or until reaction is judged complete (LC/MS). The reaction mixture is concentrated to dryness over a rotavap. The crude chloride residue was suspended in toluene, sonicated and concentrated to dryness. The process was repeated three times and dried under vacuum to give the substituted methylene chloride (2), usually as an off-white solid, which was used for next step without further purification. Alternatively, a solution of aqueous 1N Na$_2$CO$_3$ is then added to produce a solution of pH~8. the mixture was extracted with DCM (3×10-50 mL), dried over sodium sulfate, and concentrated to the crude substituted methylene chloride (2a), which is then purified by column chromatography on silica gel (0-100% ethyl acetate-hexanes).

General Method D for Preparing Substituted Methylene Bromide (2b).

To a solution of substituted methylene alcohol (1) (0.1 to 2 mmol) in DCM (1-10 mL) was added Ph$_3$P Br$_2$ dropwise (2 eq to 5 eq) at 0° C. or RT. The reaction mixture was stirred at RT for 10 min to 2 h, or until reaction is judged complete (LC/MS). The reaction mixture is concentrated to dryness over a rotavap. The residue purified by column chromatography on silica gel (0-100% ethyl acetate-hexanes) to afford the pure bromide 2b.

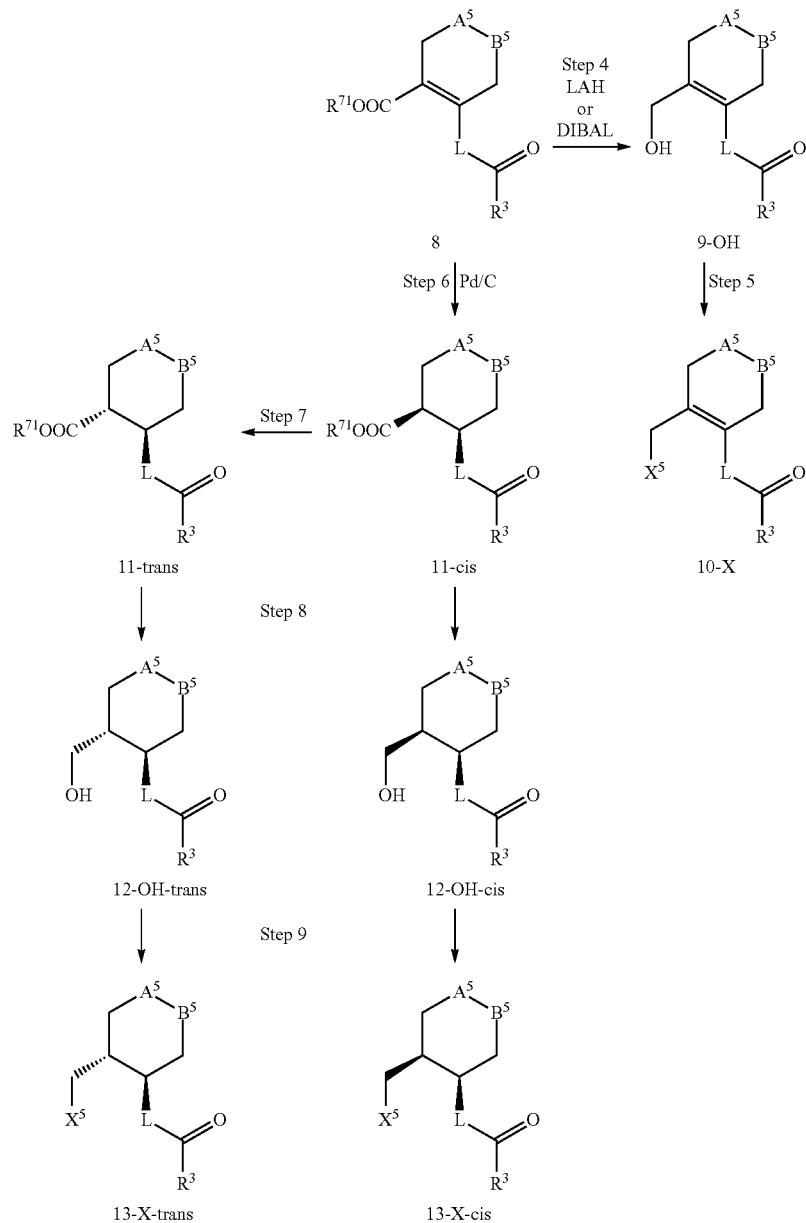

General Method E for Preparing Heterocyclic Methylene Derivatives 9, 10, 12 and 13.

Reduction of the ester group of heterocyclohexene carboxylate 8 by LAH or DIBAL gives the corresponding alcohol 9-OH (Step 4). Further reaction of the alcohol 9-OH with thionyl chloride, $Ph_3PBr_2$ (or $CBr_4$-$Ph_3P$ or $PBr_3$), or alkyl/aryl sufonyl chloride produces the corresponding 10-X chloride, bromide or sulfonate (Step 5).

Alternatively, the double bond of heterocyclohexene carboxylate 8 is reduced to give the cis-heterocyclohexane 11-cis carboxylate under palladium catalyzed hydrogenation conditions (Step 6). Reduction of the ester group of 11-cis by LAH or DIBAL yields cis-alcohol 12-OH-cis (Step 8). Conversion of the alcohol 12-OH-cis to its chloride, bromide or sulfonate (such as mesylate, tosylate) 13-X-cis can be achieved by reacting with thionyl chloride, or $Ph_3PBr_2$, or sulfonyl chloride (such as mesyl chloride or tosyl chloride) (Step 9). The cis-cyclohexane carboxylate 11-cis can also be isomerized to the thermodynamically more stable trans-isomer 11-trans by the treatment with an alcoholic alkoxide (e.g., ethoxide) solution. Analogously, transformation of 11-trans ester to 12-trans alcohol and 13-X-trans halide is accomplished by applying conditions of Step 8 and Step 9 similar to these for the corresponding cis-isomers.

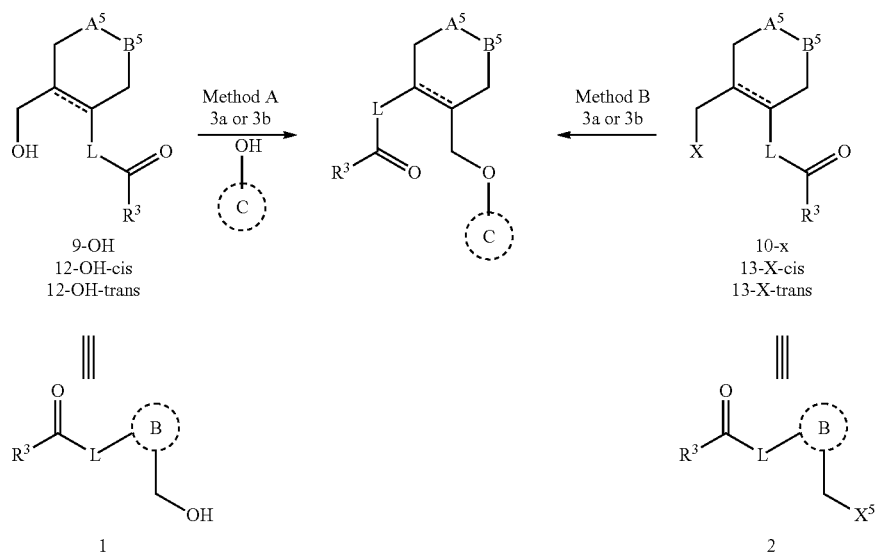

Coupling of the (hetero)cyclic methylene derivatives 9, 10, 12 and 13 with hydroxyl (hetero)arylaldehyde derivatives (3a/3b) by general method A or B affords the corresponding aryloxy/heteroarylether analogs (4c and 4d).

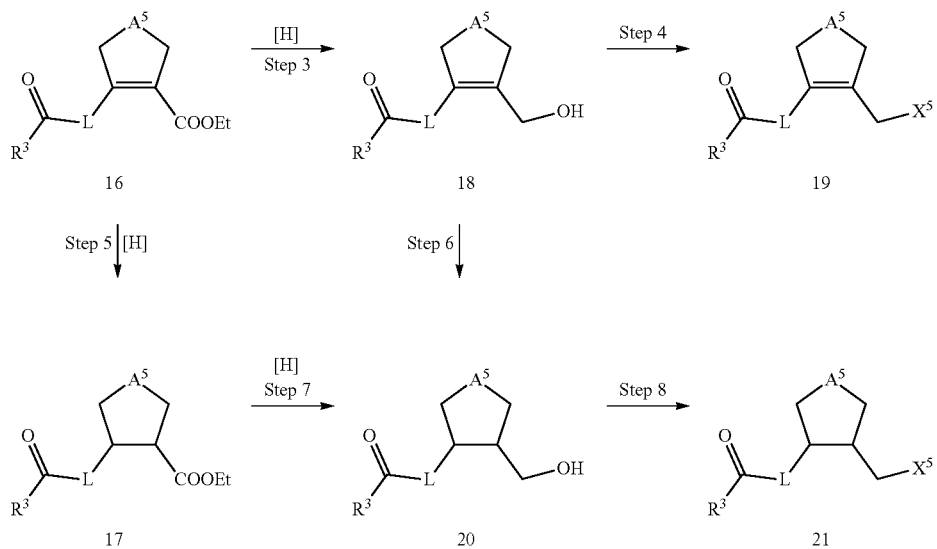

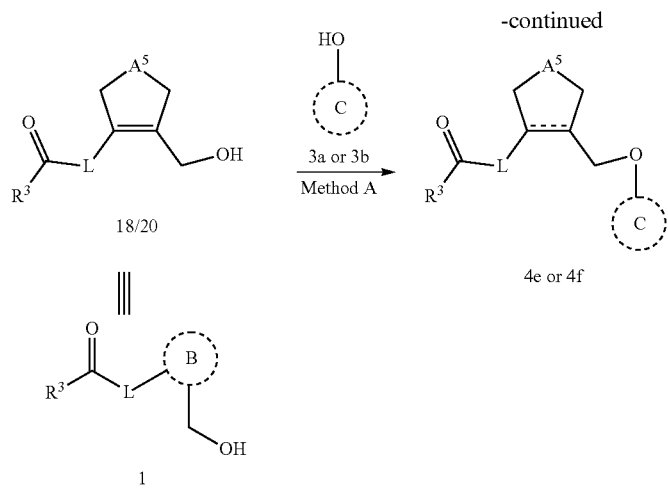

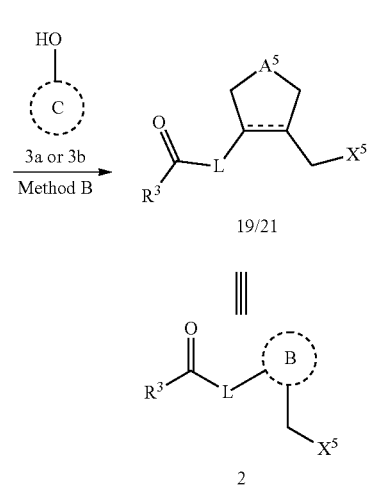

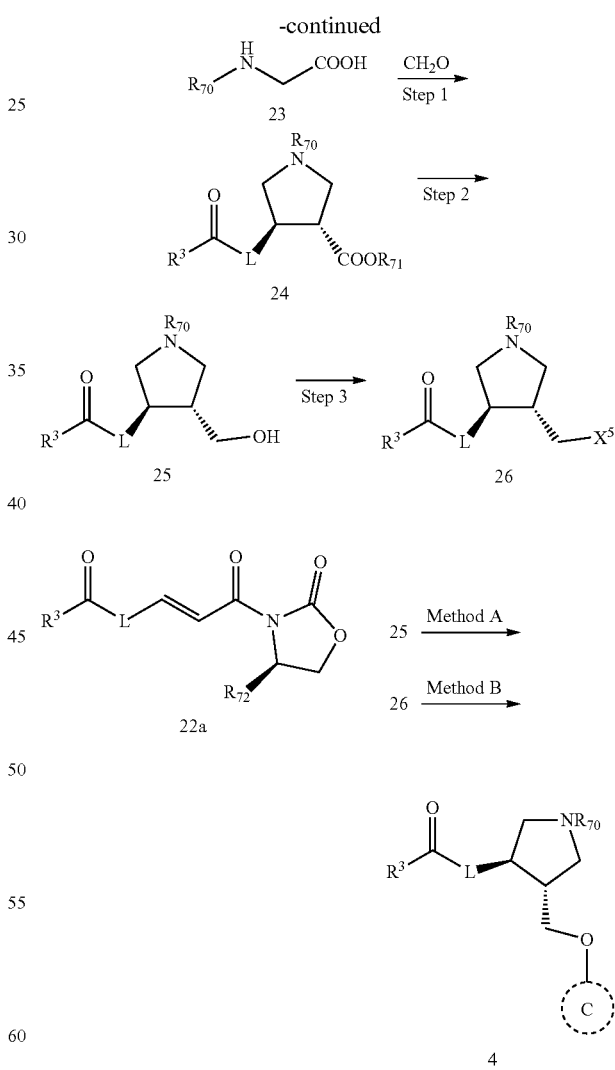

General Method F for Preparing Heterocyclic Methylene Derivatives 18, 19, 20 and 21.

The ketone ester 14 is converted to the triflate intermediate 15 by treating with a triflating agent (e.g., triflic anhydride) in the presence of an organic base such as Hunig's base (Step 1). Suzuki coupling of the triflate 15 with a boronic acid or ester affords heterocyclo carboxylate 16 (Step 2). Subsequent reduction of the ester group by LAH or DIBAL gives the corresponding alcohol 18 (Step 3). Further reaction of the alcohol 18 with thionyl chloride, $Ph_3PBr_2$ (or $CBr_4$-$Ph_3P$ or $PBr_3$), or alkyl/aryl sufonyl chloride produces the corresponding 19 chloride, bromide or sulfonate (Step 4).

Alternatively, the double bond of 16 is reduced to give the saturated heterolic analog 17 under palladium catalyzed hydrogenation conditions (Step 5). Reduction of the ester group of 17 by LAH or DIBAL yields alcohol 20 (Step 7). Conversion of the alcohol 20 to its chloride, bromide or sulfonate (such as mesylate, tosylate) 21 can be achieved by reacting with thionyl chloride, or $Ph_3PBr_2$, or sufonyl chloride (such as mesyl chloride or tosyl chloride) (Step 8).

Coupling of the (hetero)cyclic methylene derivatives 18, 19, 20 and 21 with hydroxyl (hetero)arylaldehyde derivatives (3a/3b) by general method A or B affords the corresponding aryloxy/heteroaryloxyether analogs (4e and 4f).

Chiral pyrrolidine methylene derivatives 25 and 26 can be prepared according to reaction sequence depicted herein. The pyrrolidine ester 24 is produced via a 1,3-dipolar cycloaddition of alkene 22 with azomethine-ylide generated in situ from formaldehyde and amino acid 23 alkene (Step 1). Subsequent reduction of the ester to alcohol 24 and further conversion 25 are accomplished by analogous methods described herein. If a chiral auxiliary group such as chiral oxazolidinone derivative 22a is used, optically active pyrrolidine derivatives 25 and 26 can also be obtained. Coupling of 25 and 26 with hydroxyl (hetero)arylaldehyde derivatives (3a/3b) by general method A or B affords the corresponding aryloxy/heteroaryloxyether analogs (4).

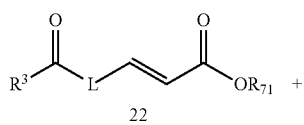

Separate from the general synthesis of tetrahydrothiophenes (i.e., 20 and 21, A=S) described herein. Also described is a different synthetic approach to this class of analogs.

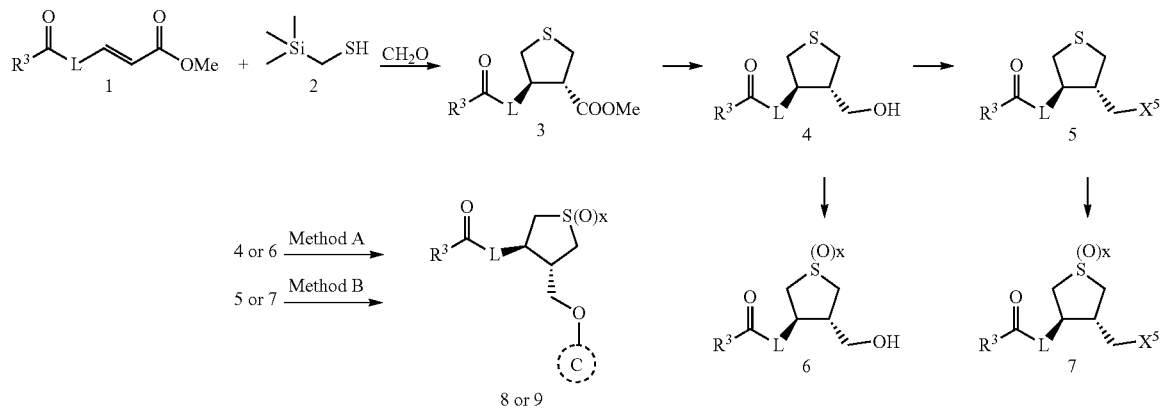
Other heterocyclic analogs (compound 5) with C—N linkage are synthesized by applying Buchwald/Hartwig amination conditions. Many of the cyclic amines (1) are available commercially (e.g., 1a, 1b, 1c, 1d, and 1e).
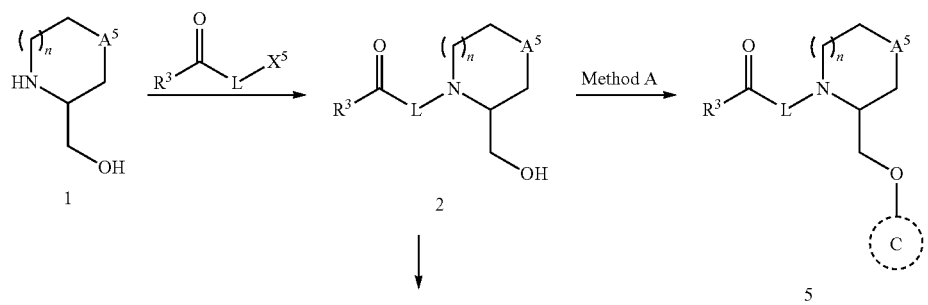
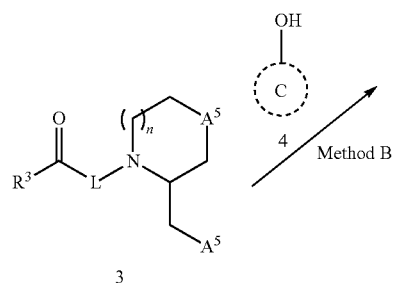
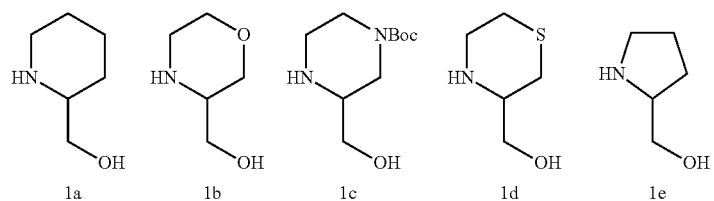

Protected amides of formula —CONHR[95] and —CONHOR[95] can be converted e.g., hydrolyzed to the corresponding amides according to methods known to the skilled artisan.

Scheme 1

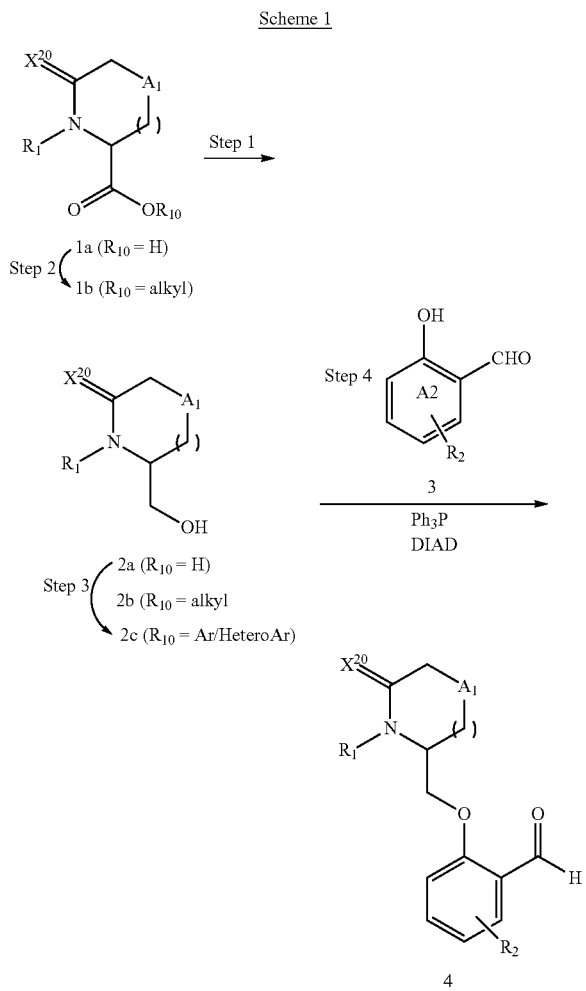

Compounds of structure 4 can be synthesized via general synthetic scheme 1. Reduction of carboxylic acid derivative 1 gives hydrxoymethyl analog 2, which can be N-derivatized at via copper-mediated N-arylation reaction (CuI, Ar—I, base such as N,N-dimethylethylenediamine and potassium phosphate, heat) to give key hydroxymethyl intermediate 3. Coupling of 3 with phenol aldehyde 4 produces the desired aldehyde analog 5 via typical Mistunobu conditions using either triphenylphosphine or polymer supported triphenylphosphine. $A_1$ is a heteroatom or a hydrocarbyl moiety as defined herein.

General Method Step 1—Reduction of Carboxylic Acid Derivative 1 to Methyl Alcohol 2:

To a suspension of carboxylic acid 1(1-10 mmol) in MeOH or EtOH (2-10 mL) at 0° C. was added $SOCl_2$ (1.5 eq). After stirred at room temperature for 1-12h, it was concentrated to remove all solvents, dried under high vacuum to give corresponding methyl or ethyl ester. The ester was dissolved in MeOH or EtOH (5-30 mL), to this solution, was added $NaBH_4$ (1-4 eq) at 0° C., the mixture was warmed up to room temperature and stirred for additional 1-24 h. The mixture was quenched with Sat. $NH_4Cl$, filtered off the insolubles and the filtrate was concentrated to give crude product, which was purified by flash silica gel chromatography to give the corresponding hydroxymethylene compound 2.

General Method Step 2—N-Alkylation (1a to 1b):

The carboxylate 1a ($R_1$=H) can be first alkylated and then reduced to give N-alkyl hydroxymethylene analog 1b ($R_1$=alkyl). In a typical procedure, the carboxylate 1a (1-10 mmol) is first dissolved in DMF (2-20 mL); to this was then added a base such as NaH or $Cs_2CO_3$ (1-1.2 eq), followed by the addition of alkyl halide (eg, BnBr) (0.9-1.5 eq). The reaction allowed to proceed at room temperature of heat at 40 to 115° C. for 0.5 to 24 h. In workup A, water was added to the reaction mixture, the precipitated product was collected, washed with water, and then subjected to preparative HPLC or flash silica gel chromatography purification. In workup B (for products that did not precipitate), diluted HCl or aqueous $NH_4Cl$ was added at 0° C. to adjusted the pH to~7, the reaction mixture was partitioned between ethyl acetate or dichloromethane and aqueous sodium chloride and the organic layer separated, dried, and solvent removed under vacuum to afford crude product which was purified by automated silica gel column chromatography, reaction appropriate solvents mixture (e.g., ethyl acetate/hexanes).

General Method Step 3—Copper-Mediated N-Arylation from 2a to 2c:

For cyclic amines (X=H, H), to a solution of hydroxymethylene compound 2a (1-10 mmol) and aryl/hetero iodide (1-1.5 eq) in iPrOH (0.5-10 mL) was added ethylene diol (1.3 eq) and CuI (6.7 mol %), followed by $K_3PO_4$ (1.3 eq), then it was degassed and heated at 88° C. for 6-24 h.

Alternatively, for lactams (X=O), to a solution of hydroxymethylene compound 2a (1-10 mmol) and aryl/hetero iodide (1-1.5 eq) in Dioxane (2-20 mL) was added CuI (0.17 eq), N,N-dimethylethylenediamine (0.17 eq), $K_3PO_4$ (1.7 eq), then it was degassed and heated at 100° C. for 6-48 h.

Workup for both procedures: the reaction mixture was cooled to room temperature the mixture was diluted with EtOAc and water, organic layer was separated and the aqueous layer was extracted with EtOAc, organic layer was combined, washed with brine, dried and concentrated to give crude product, which was purified by flash silica gel chromatography to give N-aryl/heteroaryl compound 2c.

General Method C—Mitsunobu Conditions

A hydroxyl (hetero)arylaldehyde derivatives (4) (0.1-2 mmol) mixture with substituted methylene alcohol (3) (0.8 to 1.2 eq) and (polymer-supported) $PPh_3$ (1-1.5 eq) in anhydrous THF (1-10 mL) was stirred under nitrogen until complete dissolution. The solution was cooled to 0° C. on ice bath and DIAD or DEAD (1.1 eq) in THF or toluene was added dropwise over a 1-20 min period. The ice cooling bath was allowed to expire over 90 min and the mixture was stirred at RT for 2-48 hours. The mixture was filtered through a pad of silica. The silica was washed with ethyl acetate 2-20 mL. The combined filtrates were evaporated and the residue was dried on highvac. The residue was purified by preparative HPLC or flash silica gel chromatography.

Scheme 2

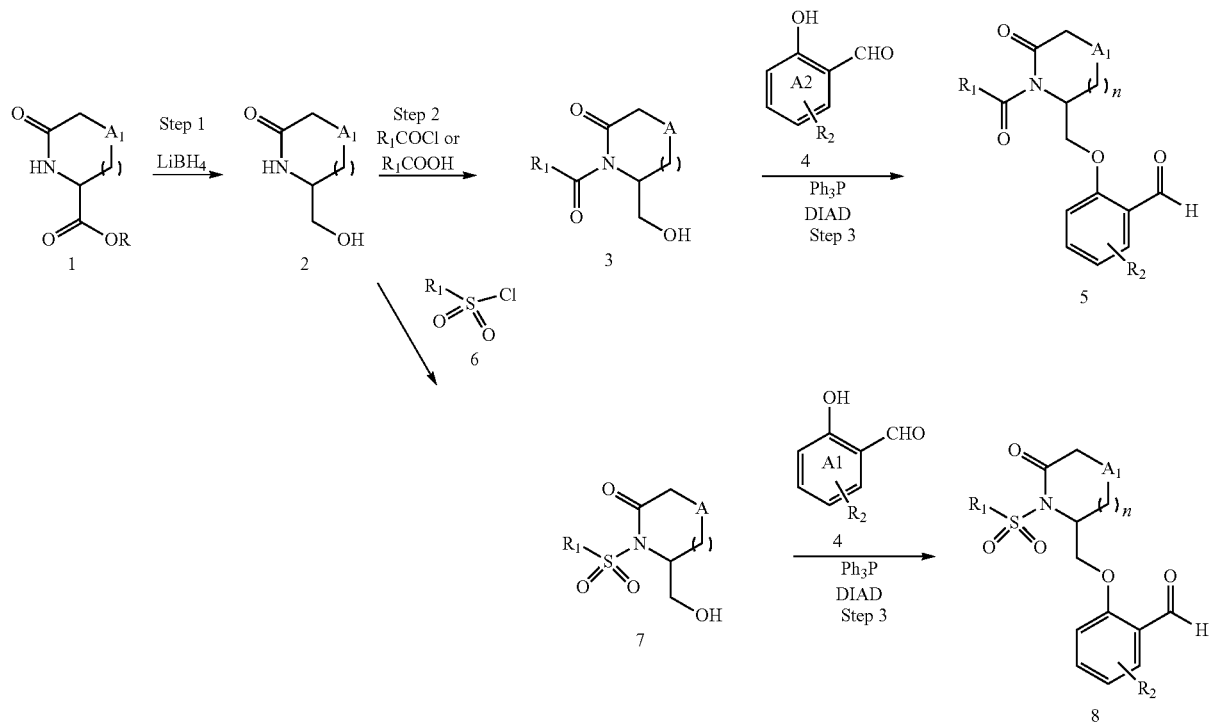

Compounds of structure 5 can be synthesized via general synthetic scheme 1. Reduction of carboxylic acid derivative 1 gives hydrxoymethyl analog 2, which can be N-alkylated by simple alkyl halide (base, $R_1X$, heat) or aryl halide (ArX) via copper-mediated N-arylation reaction (CuI, Ar—I, base such as N,N-dimethylethylenediamine and potassium phosphate, heat) to give key hydroxymethyl intermediate 3. Coupling of 3 with phenol aldehyde 4 produces the desired aldehyde analog 5 via typical Mistunobu conditions using either triphenylphosphine or polymer supported triphenylphosphine. $A_1$ is a heteroatom or a hydrocarbyl moiety as defined herein.

General Method Step 1—Reduction of Carboxylic Acid Derivative 1 to Methyl Alcohol 2:

To a suspension of carboxylic acid 1(1-10 mmol) in MeOH or EtOH (2-10 mL) at 0° C. was added $SOCl_2$ (1.5 eq). After stirred at room temperature for 1-12h, it was concentrated to remove all solvents, dried under high vacuum to give corresponding methyl or ethyl ester. The ester was dissolved in MeOH or EtOH (5-30 mL), to this solution, was added $NaBH_4$ (1-4 eq) at 0° C., the mixture was warmed up to room temperature and stirred for additional 1-24 h. The mixture was quenched with Sat. $NH_4Cl$, filtered off the insolubles and the filtrate was concentrated to give crude product, which was purified by flash silica gel chromatography to give the corresponding hydroxymethylene compound 2.

General Method Step 2—Copper-Mediated N-Arylation:

For cyclic amines (X=H, H), to a solution of hydroxymethylene compound 2 (1-10 mmol) and aryl/hetero iodide (1-1.5 eq) in iPrOH (0.5-10 mL) was added ethylene diol (1.3 eq) and CuI (6.7 mol %), followed by $K_3PO_4$ (1.3 eq), then it was degassed and heated at 88° C. for 6-24 h. Alternatively, for lactams (X=O), to a solution of hydroxymethylene compound 2 (1-10 mmol) and aryl/hetero iodide (1-1.5 eq) in Dioxane (2-20 mL) was added CuI (0.17 eq), N,N-dimethylethylenediamine (0.17 eq), $K_3PO_4$ (1.7 eq), then it was degassed and heated at 100° C. for 6-48 h.

Workup for both procedures: the reaction mixture was cooled to room temperature the mixture was diluted with EtOAc and water, organic layer was separated and the aqueous layer was extracted with EtOAc, organic layer was combined, washed with brine, dried and concentrated to give crude product, which was purified by flash silica gel chromatography to give N-aryl/heteroaryl compound 3.

General Method Step 2b—N-Alkylation:

The carboxylate 1 can be first alkylated and then reduced to give N-alkyl hydroxymethylene analog 3. In a typical procedure, the carboxylate 1 (1-10 mmol) is first dissolved in DMF (2-20 mL); to this was then added a base such as NaH or $Cs_2CO_3$ (1-1.2 eq), followed by the addition of alkyl halide (eg, BnBr) (0.9-1.5 eq). The reaction allowed to proceed at room temperature of heat at 40 to 115° C. for 0.5 to 24 h. In workup A, water was added to the reaction mixture, the precipitated product was collected, washed with water, and then subjected to preparative HPLC or flash silica gel chromatography purification. In workup B (for products that did not precipitate), diluted HCl or aqueous $NH_4Cl$ was added at 0° C. to adjusted the pH to ~7, the reaction mixture was partitioned between ethyl acetate or dichloromethane and aqueous sodium chloride and the organic layer separated, dried, and solvent removed under vacuum to afford crude product which was purified by automated silica gel column chromatography, reaction appropriate solvents mixture (e.g., ethyl acetate/hexanes).

General Method C—Mitsunobu Conditions

A hydroxyl (hetero)arylaldehyde derivatives (4) (0.1-2 mmol) mixture with substituted methylene alcohol (3) (0.8 to 1.2 eq) and (polymer-supported) PPh₃ (1-1.5 eq) in anhydrous THF (1-10 mL) was stirred under nitrogen until complete dissolution. The solution was cooled to 0° C. on ice bath and DIAD or DEAD (1.1 eq) in THF or toluene was added dropwise over a 1-20 min period. The ice cooling bath was allowed to expire over 90 min and the mixture was stirred at RT for 2-48 hours. The mixture was filtered through a pad of silica. The silica was washed with ethyl acetate 2-20 mL. The combined filtrates were evaporated and the residue was dried on highvac. The residue was purified by preparative HPLC or flash silica gel chromatography.

Prodrug Synthesis

Syntheses of the ester prodrugs start with the free carboxylic acid bearing the tertiary amine. The free acid is activated for ester formation in an aprotic solvent and then reacted with a free alcohol group in the presence of an inert base, such as triethyl amine, to provide the ester prodrug. Activating conditions for the carboxylic acid include forming the acid chloride using oxalyl chloride or thionyl chloride in an aprotic solvent, optionally with a catalytic amount of dimethyl formamide, followed by evaporation. Examples of aprotic solvents, include, but are not limited to methylene chloride, tetrahydrofuran, and the like. Alternatively, activations can be performed in situ by using reagents such as BOP (benzotriazol-1-yloxytris(dimethylamino) phosphonium hexafluorolphosphate, and the like (see Nagy et al., 1993, Proc. Natl. Acad. Sci. USA 90:6373-6376) followed by reaction with the free alcohol. Isolation of the ester products can be affected by extraction with an organic solvent, such as ethyl acetate or methylene chloride, against a mildly acidic aqueous solution; followed by base treatment of the acidic aqueous phase so as to render it basic; followed by extraction with an organic solvent, for example ethyl acetate or methylene chroride; evaporation of the organic solvent layer; and recrystalization from a solvent, such as ethanol. Optionally, the solvent can be acidified with an acid, such as HCl or acetic acid to provide a pharmaceutically acceptable salt thereof. Alternatively the crude reaction can be passed over an ion exchange column bearing sulfonic acid groups in the protonated form, washed with deionized water, and eluted with aqueous ammonia; followed by evaporation.

Suitable free acids bearing the tertiary amine are commercially available, such as 2-(N-morpholino)-propionic acid, N,N-dimethyl-beta-alanine, and the like. Non-commercial acids can be synthesized in straightforward manner via standard literature procedures.

Carbonate and carbamate prodrugs can be prepared in an analogous way. For example, amino alcohols and diamines can be activated using activating agents such as phosgene or carbonyl diimidazole, to provide an activated carbonates, which in turn can react with the alcohol and/or the phenolic hydroxy group on the compounds utilized herein to provide carbonate and carbamate prodrugs.

Various protecting groups and synthetic methods related to them that can be used or adapted to make compounds of the invention can be adapted from the references Testa et al., Hydrolysis in Drug and Prodrug Metabolism, June 2003, Wiley-VCH, Zurich, 419-534 and Beaumont et al., Curr. Drug Metab. 2003, 4:461-85.

Provided herein is a method of synthesizing an acyloxymethyl version of a prodrug by adapting a method from the reference Sobolev et al., 2002, J. Org. Chem. 67:401-410.

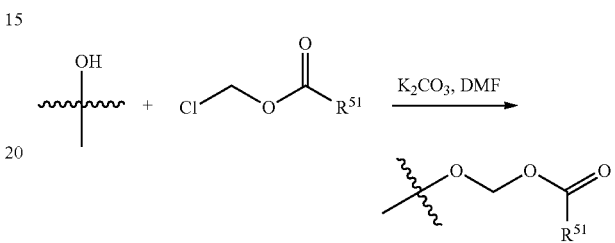

$R^{51}$ is $C_1$-$C_6$ alkyl.

Provided herein is a method for synthesizing a phosphonooxymethyl version of a prodrug by adapting a method from Mantyla et al., 2004, J. Med. Chem. 47:188-195.

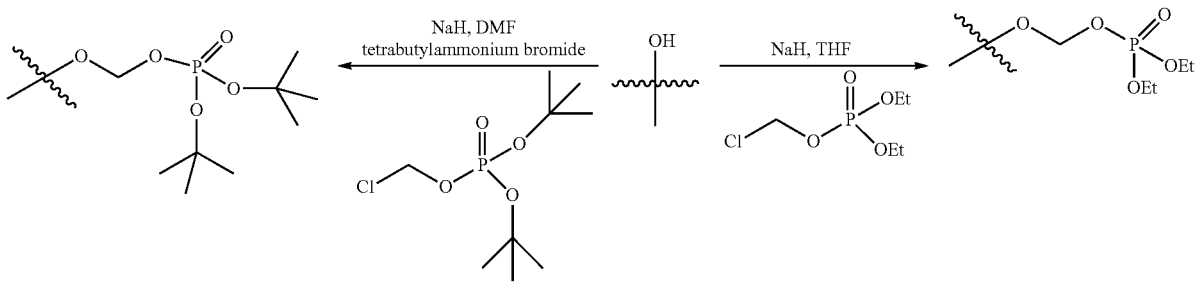

Provided herein is a method of synthesizing an alkyloxymethyl version of a prodrug

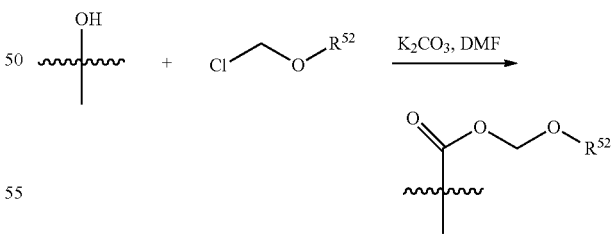

$R^{52}$ is $C_1$-$C_6$ alkyl, $C_3$-$C_8$ cycloalkyl, $C_3$-$C_9$ heterocyclyl, $C_6$-$C_{10}$ aryl, or $C_3$-$C_9$ heteroaryl.

Examples

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

In the examples below as well as throughout the application, the following abbreviations have the following meanings. If not defined, the terms have their generally accepted meanings.

The following representative B-ring and C-ring intermediates may be incorporated into the compounds of the invention by methods that are commonly known to the skilled artisan.

Preparation of
5-hydroxy-2-(2-methoxyethoxy)isonicotinaldehyde)

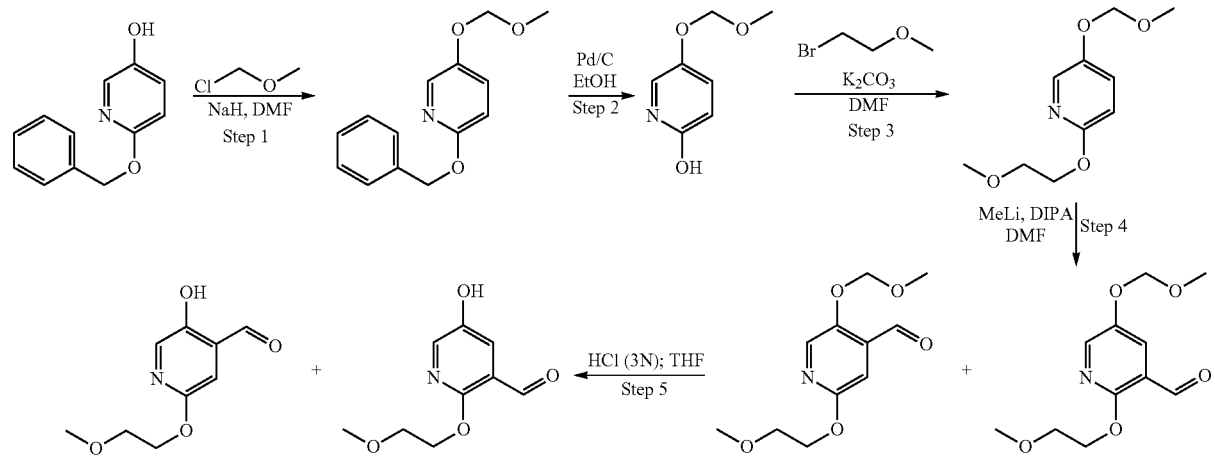

° C.=degrees Celsius
RT=Room temperature
min=minute(s)
h=hour(s)
μL=Microliter
mL=Milliliter
mmol=Millimole
eq=Equivalent
mg=Milligram
ppm=Parts per million
atm=Atmospheric pressure
MS=Mass spectrometry
LC-MS=Liquid chromatography-mass spectrometry
HPLC=High performance liquid chromatography
NMR=Nuclear magnetic resonance
Sat./sat.=Saturated
MeOH=Methanol
EtOH=Ethanol
EtOAc=Ethyl acetate
Et$_3$N=Triethylamine
Ac$_2$O=Acetic anhydride
Na(OAc)$_3$BH=Sodium triacetoxy borohydride
PBr$_3$=phosphorus tribromide
Ph$_3$P=Triphenylphosphine
Ph$_3$PBr$_2$=Triphenylphosphine dibromide
CBr$_4$ Tetrabromomethane
DMF=N, N-Dimethylformamide
DCM=Dichloromethane
LAH/LiAlH$_4$=Lithium aluminum hydride
THF=Tetrahydrofuran
DIBAL=Diisobutylaluminium hydride
DIAD=Diisopropyl azodicarboxylate
DEAD=Diethyl azodicarboxylate
DIPEA=N,N-Diisopropylethylamine
Pd(dppf)Cl$_2$=[1,1'-Bis(diphenylphosphino)ferrocene] dichloropalladium(II), complex Step 1

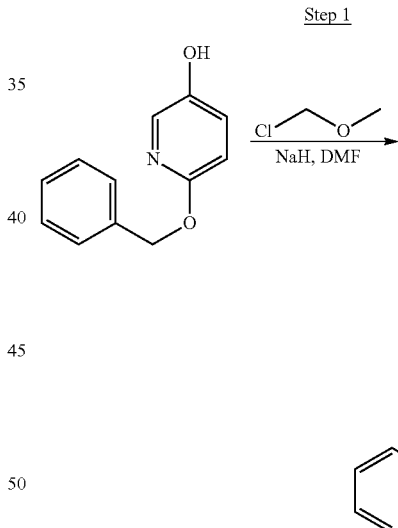

To a solution of 6-(benzyloxy)pyridin-3-ol (2.0 g, 10 mmol, 1 eq.) in DMF (20 mL) was added NaH (60% in mineral oil; 0.6 g, 15 mmol, 1.5 eq.) at 0-5° C. portion-wise. Upon the completion of addition, the mixture was continued to stir at 0-5° C. for 15 min, added chloromethyl methyl ether (0.88 g, 11 mmol, 1.1 eq.), stirred at 0-5° C. for another 20 min, and quenched with NH$_4$Cl$_{(sat.)}$ solution. The aqueous layer was extracted with EtOAc (3×20 mL) and the combined organic layers were washed with water and brine, dried over Na$_2$SO$_4$, concentrated, and purified on silica gel using 25% EtOAc/hexanes as eluent to give 2-(benzyloxy)-5-(methoxymethoxy)pyridine (2.1 g, 87%) as a colorless oil. MS (ESI) m/z 246.1 [M+H]$^+$.

Step 2

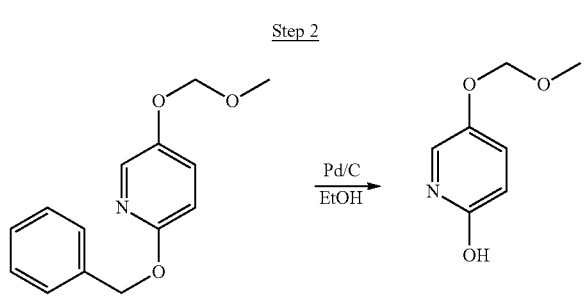 [SMILES: "EtOH" ; COCOc1ccc(OCc2ccccc2)nc1 ; COCOc1ccc(O)nc1]

To 2-(benzyloxy)-5-(methoxymethoxy)pyridine (1.8 g, 8.71 mol) in EtOH was added Pd/C (1.0 g). The mixture was charged with $H_2$ (15 psi), stirred at RT for 45 min, filtered, and concentrated to give 5-(methoxymethoxy)pyridin-2-ol (1.35 g, quantitative yield) as a pale yellow solid. MS (ESI) m/z 156.1 [M+H]$^+$.

Step 3

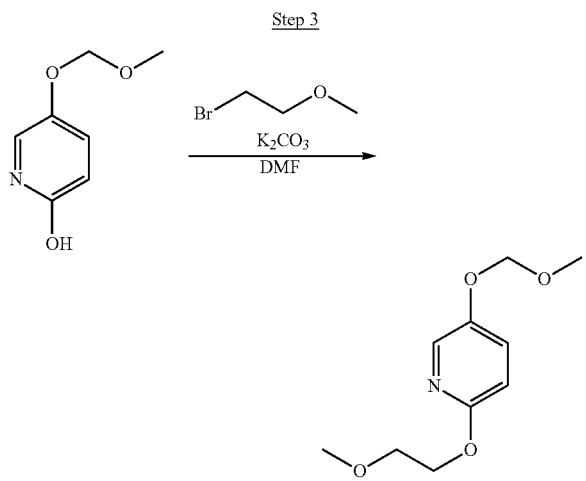

To a mixture of 5-(methoxymethoxy)pyridin-2-ol (1.35 g, 8.71 mmol, 1 eq.) and $K_2CO_3$ (6.01 g, 43.6 mmol, 5.0 eq.) in DMF (30.0 mL) was added 1-bromo-2-methoxyethane (3.61 g, 26.1 mmol, 3 eq.). The mixture was heated at 60° C. for 2 h, cooled, filtered, concentrated, and purified on silica gel using a mixture of EtOAc and hexanes as eluent to give 2-(2-methoxyethoxy)-5-(methoxymethoxy)pyridine (500 mg, 27%) as a colorless oil. $^1$H NMR (400 MHz, CDCl$_3$) δ 7.94 (d, J=3.0 Hz, 1H), 7.35 (ddd, J=8.9, 3.0, 1.0 Hz, 1H), 6.76 (dd, J=8.9, 1.0 Hz, 1H), 5.11 (s, 2H), 4.48-4.40 (m, 2H), 3.79-3.71 (m, 2H), 3.50 (s, 3H), 3.45 (s, 3H). MS (ESI) m/z 214.1 [M+H]$^+$.

Step 4

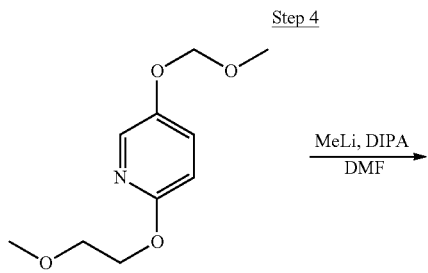

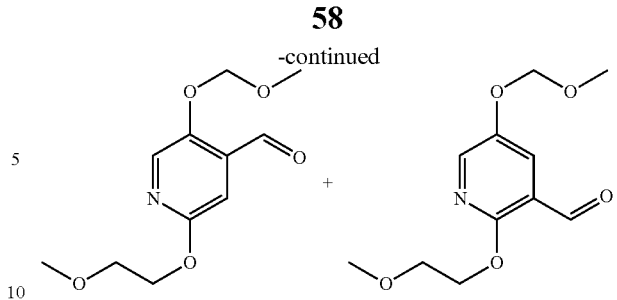

To a mixture of 2-(2-methoxyethoxy)-5-(methoxymethoxy)pyridine (1.34 g, 6.3 mol, 1 eq.) and diisopropylamine (17.5 uL, 0.13 mmol, 0.02 eq.) in THF (50 mL) was added methyl lithium (1.6 M/THF, 7 mL, 11.3 mol, 1.8 eq.) at −40° C. Upon the completion of addition, the mixture was warmed to 0° C., continued to stir at 0° C. for 3 h, cooled back down to −40° C., and added DMF (0.83 mL, 11.3 mol, 1.8 eq.) slowly. The mixture was then stirred at −40° C. for 1 h, quenched with a mixture of HCl (12 N, 12 mL) and THF (28 mL), warmed to RT, and added water (20 mL). The pH of the mixture was adjusted to pH 8-9 with solid $K_2CO_3$. The aqueous layer was extracted with EtOAc (30 mL) twice. The combined organic layers were dried over $Na_2SO_4$, concentrated, and purified on silica gel using a mixture of EtOAc and hexanes as eluent to give a mixture of 2-(2-methoxyethoxy)-5-(methoxymethoxy)isonicotinaldehyde and 2-(2-methoxyethoxy)-5-(methoxymethoxy)nicotinaldehyde (5/1, 1.27 g, 83.6%) as a pale yellow oil. $^1$H NMR (400 MHz, CDCl$_3$) δ 10.45 (s, 1H), 8.23 (s, 1H), 7.16 (s, 1H), 5.27 (s, 2H), 4.46 (dd, J=5.4, 3.9 Hz, 2H), 4.14 (q, J=7.1 Hz, 1H), 3.77-3.71 (m, 2H), 3.56 (s, 3H), 3.46 (s, 3H) and $^1$H NMR (400 MHz, CDCl$_3$) δ 10.41 (s, 1H), 8.18 (d, J=3.2 Hz, 1H), 7.85 (d, J=3.1 Hz, 1H), 5.16 (s, 2H), 4.64-4.57 (m, 2H), 3.85-3.79 (m, J=5.4, 4.0 Hz, 2H), 3.50 (s, 3H), 3.46 (s, 3H); MS (ESI) m/z 242.1 [M+H]$^+$.

Step 5

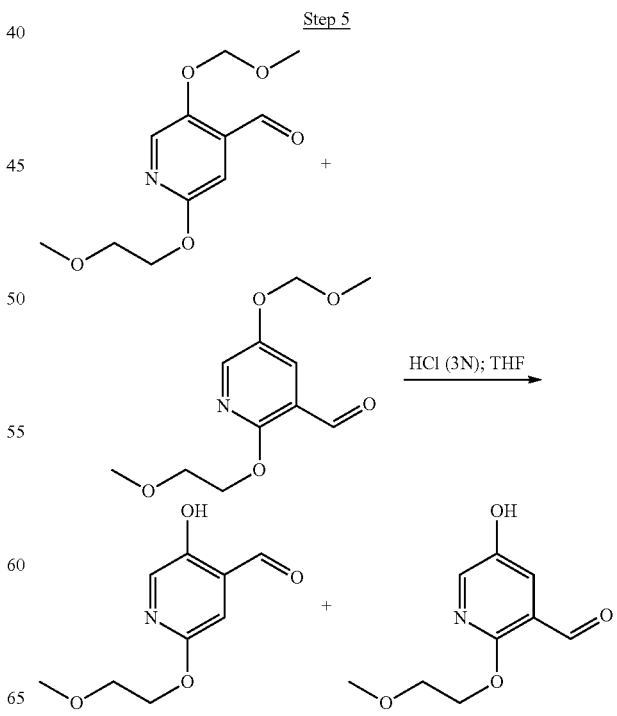

To a solution of 2-methoxy-5-(methoxymethoxy)isonicotinaldehyde (1.27 g, 5.29 mol) in THF (5 mL) was added HCl (3 N, 4 mL). The reaction was stirred at 50° C. for 1 h, cooled to RT, and diluted with water (5 mL). The mixture was neutralized to pH 7-8 with solid K$_2$CO$_3$ and the aqueous layer was extracted with EtOAc (100 mL) twice. The combined organic layers were dried over Na$_2$SO$_4$, concentrated, and purified on silica gel using a mixture of EtOAc and hexanes to give 5-hydroxy-2-(2-methoxyethoxy)isonicotinaldehyde (630 mg, 60%) and 5-hydroxy-2-(2-methoxyethoxy)nicotinaldehyde (120 mg, 11%). Data for 5-hydroxy-2-(2-methoxyethoxy)isonicotinaldehyde: $^1$H NMR (400 MHz, CDCl$_3$) δ 9.98 (s, 1H), 9.50 (s, 1H), 8.07 (s, 1H), 7.02 (s, 1H), 4.51-4.39 (m, 2H), 3.81-3.72 (m, 2H), 3.47 (s, 3H). LRMS (M+H$^+$) m/z 198.1. Data for and 5-hydroxy-2-(2-methoxyethoxy) nicotinaldehyde: $^1$H NMR (400 MHz, CDCl$_3$) δ 10.3 (s, 1H), 7.99 (d, J=3.2 Hz, 1H), 7.58 (d, J=3.2 Hz, 1H), 7.18-7.07 (br, 1H), 4.54 (dd, J=5.4, 3.7 Hz, 2H), 3.84 (dd, J=5.4, 3.7 Hz, 2H), 3.49 (s, 3H); MS (ESI) m/z 198.1 [M+H]$^+$.

Preparation of 2,6-dihydroxybenzaldehyde

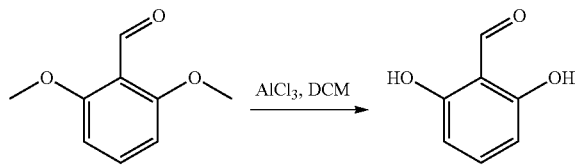

Into a 3000-mL three neck round-bottom flask, was placed a solution of AlCl$_3$ (240 g, 1.80 mol, 3.00 equiv) in dichloromethane (1200 mL). A solution of 2,6-dimethoxybenzaldehyde (100 g, 601.78 mmol, 1.00 eq) in dichloromethane (800 ml) was added to the reaction mixture dropwise at 0° C. The resulting solution was stirred overnight at room temperature, and then it was quenched with 200 mL of diluted HCl (2M). The resulting solution was extracted with 2×200 mL of dichloromethane. The combined organic layers were concentrated under vacuum. The residue was applied onto a silica gel column with ethyl acetate/petroleum ether (1:200-1:50) as eluent to furnish 40 g (48%) of 2,6-dihydroxybenzaldehyde as a yellow solid.

$^1$HNMR (300 MHz, DMSO-d$_6$) δ 11.25 (s, 2H), 10.25 (s, 1H), 7.36 (m, 1H), 6.36 (d, J=8.4 Hz 2H); MS (ESI) m/z 139 [M+H]$^+$.

Preparation of 5-hydroxy-2-methoxyisonicotinaldehyde

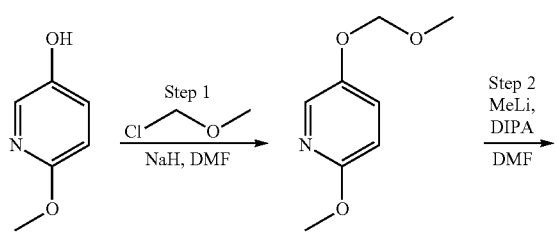

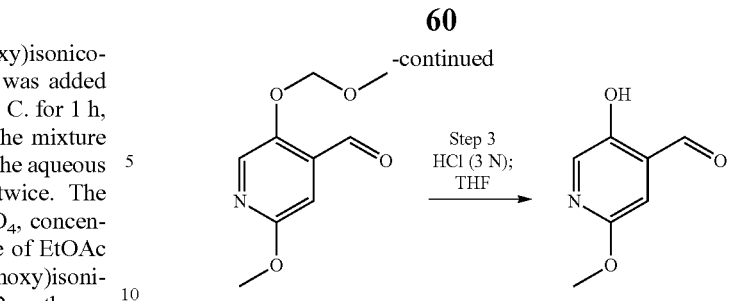

Step 1:

To a solution of 6-methoxypyridin-3-ol (20 g, 0.16 mol) in DMF (200 mL) was added NaH (60% in mineral oil; 9.6 g, 0.24 mol) at 0-5° C. portion-wise. Upon the completion of addition, the mixture was continued to stir at 0-5° C. for 15 min followed by additional of chloromethyl methyl ether. The mixture was stirred at 0-5° C. for another 20 min and quenched with aqueous NH$_4$Cl$_{(sat)}$. The aqueous layer was extracted with EtOAc (3×100 mL) and the combined organic layer was washed with water and brine, dried over Na$_2$SO$_4$, and concentrated under reduced pressure. The residue was purified on silica gel with 25% EtOAc/hexanes as eluent to give 2-methoxy-5-(methoxymethoxy)pyridine (24.1 g, 89.3%) as a colorless oil. $^1$H NMR (400 MHz; CDCl$_3$) 7.97 (d, 1H), 7.35 (dd, 1H), 6.70 (d, 1H), 5.12 (s, 2H), 3.91 (s, 3H), 3.51 (s, 3H); MS (ESI) m/z 170.1 [M+H]$^+$.

Step 2:

To a mixture of 2-methoxy-5-(methoxymethoxy)pyridine (30 g, 0.178 mol) and diisopropylamine (507 uL, 3.6 mmol) in THF (500 mL) was added methyl lithium (1.6 M/THF, 200 mL, 0.32 mol) at −40° C. Upon the completion of addition, the mixture was warmed to 0° C. and continued to stir at 0° C. for 3 h. The reaction mixture was then cooled back down to −40° C. followed by addition of DMF (24.7 mL, 0.32 mol) slowly. The mixture was then stirred at −40° C. for 1 h and quenched with a mixture of HCl (12 N, 120 mL) and THF (280 mL). Water (200 mL) was added and the pH of the mixture was adjusted to pH 8-9 with solid K$_2$CO$_3$. The mixture was extracted with EtOAc (300 mL) twice. The organic layer was combined, dried over Na$_2$SO$_4$, and concentrated to give 2-methoxy-5-(methoxymethoxy)isonicotinaldehyde (33.5 g, 95.7%) as a brown solid, which was used for next step without further purification. $^1$H NMR (400 MHz; CD$_3$OD) 7.90 (s, 1H), 6.92 (s, 1H), 5.64 (s, 1H), 5.20 (s, 2H), 3.84 (s, 3H), 3.48 (s, 3H); MS (ESI) m/z 198.1 [M+H]$^+$.

Step 3:

To a solution of 2-methoxy-5-(methoxymethoxy)isonicotinaldehyde (33.5 g, 0.17 mol) in THF (150 mL) was added HCl (3 N, 250 mL). The reaction was stirred at 50° C. for 1 h, cooled to RT and diluted with water (500 mL). The mixture was neutralized to pH 7-8 with solid K$_2$CO$_3$. The pale yellow solid was collected, washed with water, and dried in vacuum oven (40° C.) overnight to give 5-hydroxy-2-methoxyisonicotinaldehyde (17.9 g, 74.6%). $^1$H NMR (400 MHz; DMSO)=10.31 (s, 1H), 8.03 (s, 1H), 6.89 (s, 1H), 3.80 (s, 3H); MS (ESI) m/z 154.0 [M+H]$^+$.

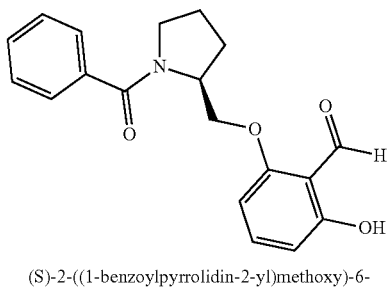

(S)-2-((1-benzoylpyrrolidin-2-yl)methoxy)-6-hydroxybenzaldehyde

GBT915—(S)-2-((1-benzoylpyrrolidin-2-yl)methoxy)-6-hydroxybenzaldehyde

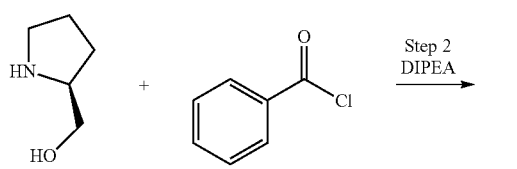

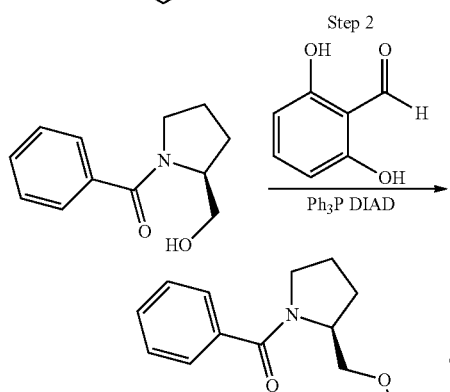

GBT915

Step 1: To a solution of (S)-pyrrolidin-2-ylmethanol (700 mg, 6.92 mmol) and DIPEA (1.20 mL, 6.92 mmol) in DCM (12 ml) at 0° C. was added benzoyl chloride (0.80 mL, 6.92 mmol), 30 min later it was diluted with more DCM and was washed with Sat. NaHCO₃, brine, dried over MgSO₄, concentrated to give crude product, which was purified by column (EtOAc 0-100%) to give (S)-(2-(hydroxymethyl)pyrrolidin-1-yl)(phenyl)methanone (1.2 g).

Step 2: To a solution of (S)-(2-(hydroxymethyl)pyrrolidin-1-yl)(phenyl)methanone (100 mg, 0.49 mmol) and 2,6-dihydroxybenzaldehyde (90 mg, 0.64 mmol) in THF (1 mL) was added PPh₃ (190 mg, 0.73 mmol) and DIAD (0.15 mL, 0.73 mmol) at room temperature, 30 min later, it was concentrated and the residue was purified by column (Hexanes/EtOAc=100:0 to 1:1) to give (S)-2-((1-benzoylpyrrolidin-2-yl)methoxy)-6-hydroxybenzaldehyde (65 mg). ¹H NMR (400 MHz, Chloroform-d) δ 11.90 (s, 1H), 10.40 (s, 1H), 7.51-7.31 (m, 6H), 6.53 (t, J=9.2 Hz, 2H), 4.65 (s, 1H), 4.38 (d, J=6.1 Hz, 2H), 3.51 (t, J=6.8 Hz, 2H), 2.29-1.90 (m, 2H), 1.79 (d, J=36.4 Hz, 1H), 1.31-1.18 (m, 1H). MS found for C₁₉H₁₉NO₄: 326.5.

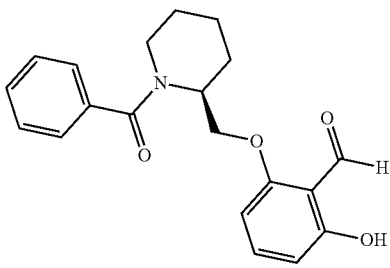

(S)-2-((1-benzoylpiperidin-2-yl)methoxy)-6-hydroxybenzaldehyde

GBT952—(S)-2-((1-benzoylpiperidin-2-yl)methoxy)-6-hydroxybenzaldehyde

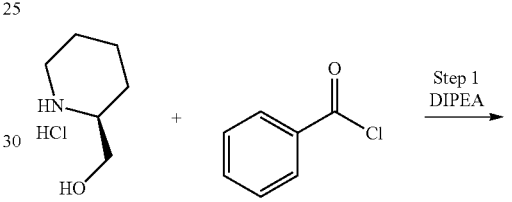

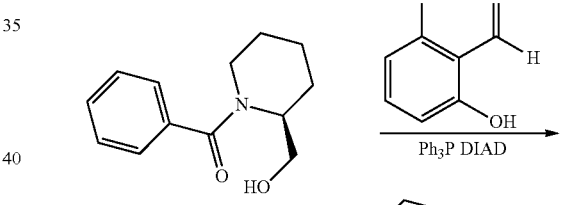

GBT952

Step 1: To a suspension of (S)-piperidin-2-ylmethanol hydrochloride (0.11 g, 0.70 mmol) in DCM (2 mL) was added DIPEA (0.27 mL, 1.54 mmol) and benzoyl chloride (0.08 mL, 0.70 mmol) at room temperature, after stirred for 30 min, it was diluted with DCM and washed with Sat. NH₄Cl, brine, dried over MgSO₄ and was concentrated to give crude product, which was purified by column (Hexanes/EtOAc=0:100) to give (S)-(2-(hydroxymethyl)piperidin-1-yl)(phenyl)methanone (84 mg).

Step 2: To a solution of 2,6-dihydroxybenzaldehyde (110 mg, 0.80 mmol) and (S)-(2-(hydroxymethyl)piperidin-1-yl)(phenyl)methanone (0.23 g, 1.04 mmol) in THF (1.5 mL) was added PPh₃ (310 mg, 1.20 mmol) and DIAD (0.23 mL, 1.20 mmol) at 0° C., then it was warmed up to room temperature and stirred for 1 h. The mixture was concentrated and purified by column (hexanes/EtOAc=60:40) to give (S)-2-((1-benzoylpiperidin-2-yl)methoxy)-6-hydroxybenzaldehyde 62 mg. ¹H NMR (400 MHz, Chloroform-d) δ 11.98 (s, 1H), 10.29 (s, 1H), 7.45-7.28 (m, 5H), 6.58-6.50 (m, 2H), 6.40 (dt, J=8.1, 0.8 Hz, 1H), 4.32 (t, J=8.5 Hz, 1H), 4.18 (s, 1H), 3.04 (s, 1H), 1.94-1.76 (m, 3H), 1.73-1.58 (m, 3H), 1.26 (dt, J=7.0, 3.1 Hz, 2H). MS found for C₂₀H₂₁NO₄: 340.2.

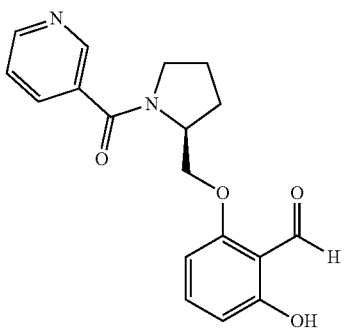

(S)-2-hydroxy-6-((1-nicotinoylpyrrolidin-2-yl)methoxy)benzaldehyde

GBT961—(S)-2-hydroxy-6-((1-nicotinoylpyrrolidin-2-yl)methoxy)benzaldehyde

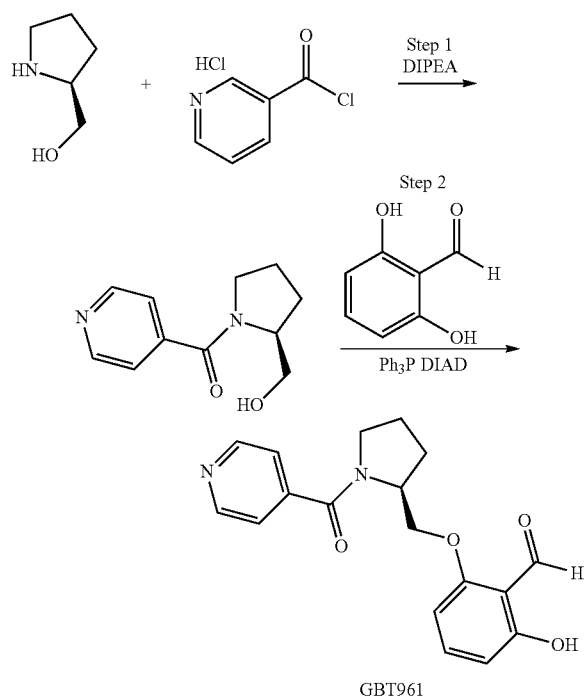

GBT961

Step 1: To a solution of (S)-pyrrolidin-2-ylmethanol (500 mg, 4.94 mmol) in DCM (10 mL) was added DIPEA (1.89 mL, 10.87 mmol), followed by nicotinyl chloride (0.92 g, 5.19 mmol) at 0° C., after stirred for 30 min, it was diluted with DCM, washed with aqueous Sat. NaHCO₃, brine, dried and concentrated to give crude product, which was purified by column (DCM/MeOH=100:0 to 80:20) to give (S)-(2-(hydroxymethyl)pyrrolidin-1-yl)(pyridin-3-yl)methanone (900 mg).

Step 2: To a solution of (S)-(2-(hydroxymethyl)pyrrolidin-1-yl)(pyridin-3-yl)methanone (150 mg, 0.73 mmol) and 2,6-dihydroxybenzaldehyde (0.13 g, 0.91 mmol) in THF (1.5 mL) was added PPh₃ (0.29 g, 1.1 mmol) and DIAD (0.21 mL, 1.1 mmol) at 0° C. and stirred at room temperature for 2 h, it was subsequently concentrated, the resulting residue was purified by column (hexanes/EtOAc=100:0 to 40:60 to DCM/MeOH=100:0 to 90:10) to give a mixture of products, which was further purified by preparative HPLC to give (S)-2-hydroxy-6-((1-nicotinoylpyrrolidin-2-yl)methoxy)benzaldehyde (68 mg). ¹H NMR (400 MHz, Chloroform-d) δ 11.90 (s, 1H), 10.40 (s, 1H), 8.78-8.72 (m, 1H), 8.68 (dd, J=4.9, 1.7 Hz, 1H), 7.82 (dt, J=7.9, 2.0 Hz, 1H), 7.40 (t, J=8.3 Hz, 1H), 7.36 (ddd, J=7.9, 4.9, 0.9 Hz, 1H), 6.53 (dd, J=8.5, 4.9 Hz, 2H), 4.66 (d, J=11.1 Hz, 1H), 4.38 (d, J=5.8 Hz, 2H), 3.54 (t, J=7.6 Hz, 2H), 2.26 (dtd, J=12.8, 7.6, 5.3 Hz, 1H), 2.19-2.10 (m, 1H), 2.10-1.98 (m, 1H), 1.88 (dt, J=12.5, 7.8 Hz, 1H). MS found for C₁₈H₁₈N₂O₄: 327.4.

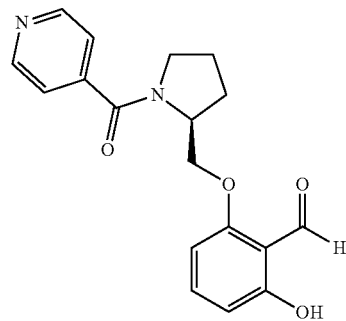

(S)-2-hydroxy-6-((1-isonicotinoylpyrrolidin-2-yl)methoxy)benzaldehyde

GBT962—(S)-2-hydroxy-6-((1-isonicotinoylpyrrolidin-2-yl)methoxy)benzaldehyde

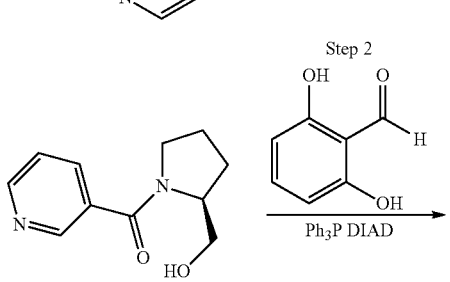

-continued

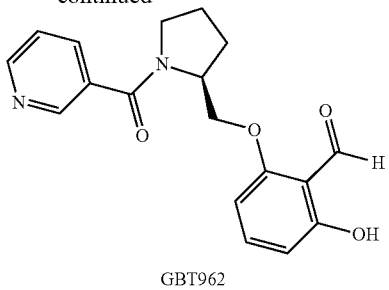

GBT962

Step 1: To a solution of (S)-pyrrolidin-2-ylmethanol (500 mg, 4.94 mmol) in DCM (10 mL) was added DIPEA (1.89 mL, 10.87 mmol), followed by nicotinyl chloride (0.88 g, 4.94 mmol) at 0° C., after stirred for 30 min, it was diluted with DCM, washed with aqueous Sat. NaHCO₃, brine, dried and concentrated to give crude product, which was purified by column (DCM/MeOH=100:0 to 80:20) to give (S)-(2-(hydroxymethyl)pyrrolidin-1-yl)(pyridin-4-yl)methanone (900 mg).

Step 2: To a solution of (S)-(2-(hydroxymethyl)pyrrolidin-1-yl)(pyridin-3-yl)methanone (150 mg, 0.73 mmol) and 2,6-dihydroxybenzaldehyde (0.13 g, 0.91 mmol) in THF (1.5 mL) was added PPh₃ (0.29 g, 1.1 mmol) and DIAD (0.21 mL, 1.1 mmol) at 0° C. and stirred at room temperature for 2 h, it was subsequently concentrated, the resulting residue was purified by column (hexanes/EtOAc=100:0 to 40:60 to DCM/MeOH=100:0 to 90:10) to give a mixture of products, which was further purified by preparative HPLC to give (S)-2-hydroxy-6-((1-isonicotinoylpyrrolidin-2-yl)methoxy)benzaldehyde (36 mg). ¹H NMR (400 MHz, Chloroform-d) δ 11.88 (s, 1H), 10.38 (s, 1H), 8.72-8.63 (m, 2H), 7.39 (t, J=8.4 Hz, 1H), 7.35-7.24 (m, 2H), 6.52 (t, J=8.6 Hz, 2H), 4.63 (dq, J=8.4, 5.1 Hz, 1H), 4.42-4.29 (m, 2H), 3.46 (hept, J=6.3, 5.4 Hz, 2H), 2.24 (dtd, J=13.3, 7.7, 5.5 Hz, 1H), 2.13 (dq, J=13.0, 6.8 Hz, 1H), 2.03 (dt, J=12.4, 6.3 Hz, 1H), 1.95-1.79 (m, 1H). MS found for C₁₈H₁₈N₂O₄: 327.4.

GBT979

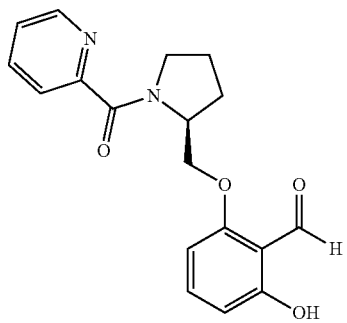

(S)-2-hydroxy-6-((1-picolinoylpyrrolidin-2-yl)methoxy)benzaldehyde

GBT979—(S)-2-hydroxy-6-((1-picolinoylpyrrolidin-2-yl)methoxy)benzaldehyde

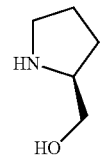 + 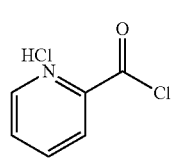 $\xrightarrow{\text{Step 1}}$ DIPEA

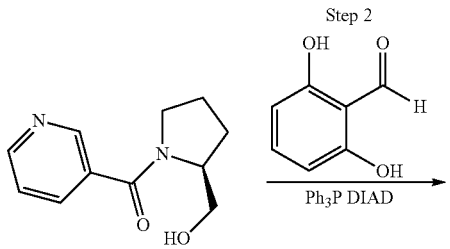

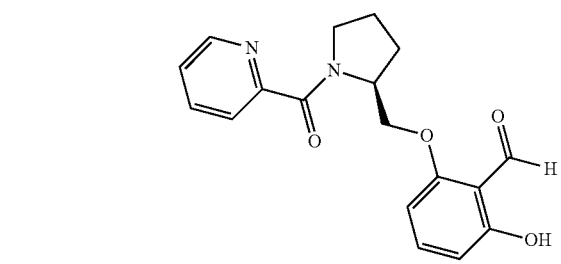

GBT979

Step 1: To a solution of (S)-pyrrolidin-2-ylmethanol (500 mg, 4.94 mmol) in DCM (10 mL) was added DIPEA (1.89 mL, 10.87 mmol), followed by isonicotinyl chloride (0.88 g, 4.94 mmol) at 0° C., after stirred for 30 min, it was diluted with DCM, washed with aqueous Sat. NaHCO₃, brine, dried and concentrated to give crude product, which was purified by column (DCM/MeOH=100:0 to 80:20) to give (S)-(2-(hydroxymethyl)pyrrolidin-1-yl)(pyridin-2-yl)methanone (900 mg).

Step 2: To a solution of (S)-(2-(hydroxymethyl)pyrrolidin-1-yl)(pyridin-2-yl)methanone (100 mg, 0.48 mmol) and 2,6-dihydroxybenzaldehyde (0.08 g, 0.6 mmol) in THF (5 mL) was added PPh₃ (polymer supported, 600 mg, 0.72 mmol) and DIAD (0.15 mL, 0.72 mmol) at room temperature. After stirred at room temperature for 3 h, the mixture was diluted with AcCN, the insoluble material was filtered off, the filtrate was concentrated to give crude product, which was purified by preparative HPLC to give (S)-2-hydroxy-6-((1-picolinoylpyrrolidin-2-yl)methoxy)benzaldehyde (15 mg). ¹H NMR (400 MHz, Chloroform-d) δ 11.92 (s, 1H), 10.39 (d, J=0.6 Hz, 1H), 8.55 (ddt, J=40.7, 4.9, 1.1 Hz, 1H), 7.89-7.74 (m, 2H), 7.40 (t, J=8.4 Hz, 1H), 7.37-7.23 (m, 1H), 6.60-6.46 (m, 2H), 4.76-4.65 (m, 1H), 4.48 (dd, J=9.5, 3.3 Hz, 1H), 4.32-4.18 (m, 1H), 3.99-3.81 (m, 1H), 3.81-3.67 (m, 1H), 2.25-1.83 (m, 4H). MS found for C₁₈H₁₈N₂O₄: 327.3.

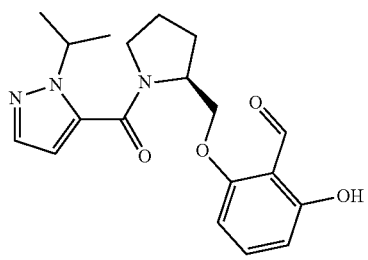

(S)-2-hydroxy-6-((1-(1-isopropyl-1H-pyrazole-5-carbonyl)pyrrolidin-2-yl)methoxy)benzaldehyde C. After stirred at room temperature for 1 h, it was diluted with AcCN, the insoluble material was filtered off and the filtrate was concentrated to give crude product, which was purified by preparative HPLC to give (S)-2-hydroxy-6-((1-(1-isopropyl-1H-pyrazole-5-carbonyl)pyrrolidin-2-yl)methoxy)benzaldehyde (46 mg). $^1$H NMR (400 MHz, Chloroform-d) δ 11.90 (s, 1H), 10.37 (s, 1H), 7.55 (d, J=2.0 Hz, 1H), 7.41 (t, J=8.4 Hz, 1H), 6.54 (d, J=8.5 Hz, 1H), 6.48 (d, J=8.3 Hz, 1H), 6.37 (d, J=2.0 Hz, 1H), 5.03-4.94 (m, 1H), 4.65 (s, 1H), 4.37 (d, J=5.4 Hz, 2H), 3.67 (s, 1H), 3.60-3.45 (m, 1H), 2.25 (dd, J=13.1, 6.1 Hz, 1H), 2.11 (ddt, J=30.4, 12.0, 6.4 Hz, 2H), 1.93 (s, 1H), 1.53 (d, J=6.6 Hz, 3H), 1.46 (d, J=6.7 Hz, 3H). MS (M+H) found for $C_{19}H_{23}N_3O_4$: 358.3.

GBT1064—(S)-2-hydroxy-6-((1-(1-isopropyl-1H-pyrazole-5-carbonyl)pyrrolidin-2-yl)methoxy)benzaldehyde

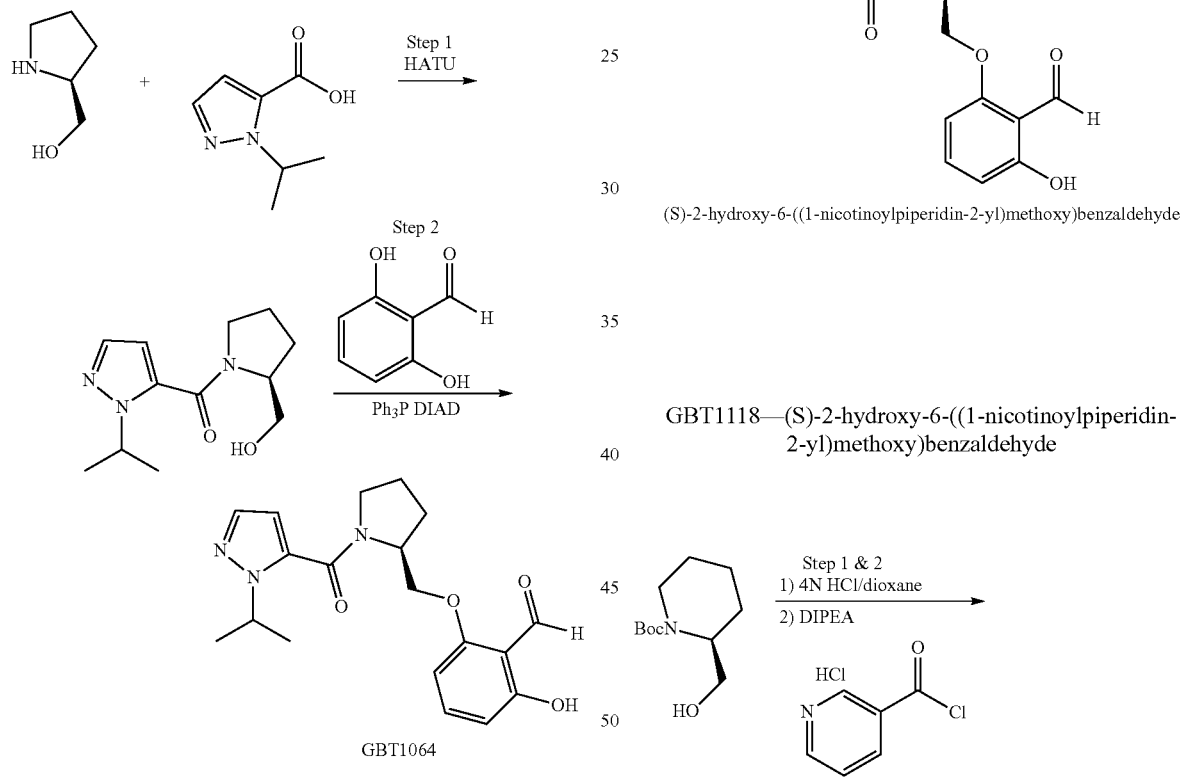

Step 1: To a solution of (S)-pyrrolidin-2-ylmethanol (100 mg, 1 mmol) and 1-isopropyl-1H-pyrazole-5-carboxylic acid (0.15 g, 1mmol) in DMF (2 mL) was added HATU (0.38 g, 1 mmol) and then the mixture was stirred until finished, it was diluted with water and extracted with EtOAc, organic layer was dried and concentrated to give crude product, which was purified by column (100% EtOAc) to give (S)-(2-(hydroxymethyl)pyrrolidin-1-yl)(1-isopropyl-1H-pyrazol-5-yl)methanone (120 mg).

Step 2: To a solution of (S)-(2-(hydroxymethyl)pyrrolidin-1-yl)(1-isopropyl-1H-pyrazol-5-yl)methanone (120 mg, 0.51 mmol) and 2,6-dihydroxybenzaldehyde (0.09 g, 0.66 mmol) in THF (4 mL) was added PPh$_3$ (Polymer supported, 640 mg, 0.77 mmol) and DIAD (0.16 mL, 0.77 mmol) at 0°

(S)-2-hydroxy-6-((1-nicotinoylpiperidin-2-yl)methoxy)benzaldehyde

GBT1118—(S)-2-hydroxy-6-((1-nicotinoylpiperidin-2-yl)methoxy)benzaldehyde

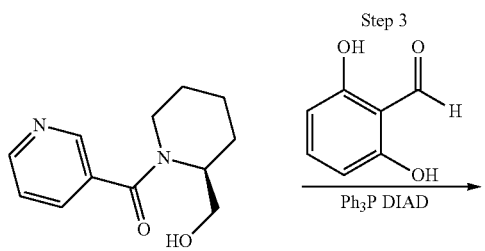

-continued

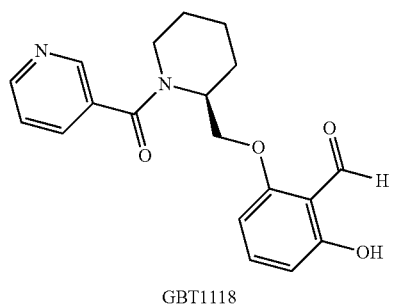

GBT1118

Step 1&2: To a solid sample of (S)-tert-butyl 2-(hydroxymethyl)piperidine-1-carboxylate (215 mg, 1.02 mmol) was added 4N HCl in dioxane (1 mL). After stirred for 30 min, it was concentrated to give (S)-piperidin-2-ylmethanol HCl salt. To a suspension of (S)-piperidin-2-ylmethanol HCl salt in DCM (3 mL) at 0° C. was added DIPEA (0.39 mL, 2.24 mmol) and nicotinyl chloride (0.2 g, 1.12 mmol). After stirred for 30 min, it was diluted with DCM, washed with aqueous Sat. NaHCO₃, brine, dried and concentrated to give crude product, which was purified by column (DCM/MeOH=90:10) to give (S)-(2-(hydroxymethyl)piperidin-1-yl)(pyridin-3-yl)methanone (130 mg).

Step 2: To a solution of (S)-(2-(hydroxymethyl)piperidin-1-yl)(pyridin-3-yl)methanone (130 mg, 0.59 mmol) and 2,6-dihydroxybenzaldehyde (0.11 g, 0.77 mmol) in THF (4 mL) was added PPh₃ (polymer supported, 0.74 g, 0.89 mmol) and DIAD (0.17 mL, 0.89 mmol) at 0° C. and stirred at room temperature for 2 h, it was subsequently concentrated, the resulting residue was purified by preparative HPLC to give (S)-2-hydroxy-6-((1-nicotinoylpiperidin-2-yl)methoxy)benzaldehyde (30 mg). ¹H NMR (400 MHz, Chloroform-d) δ 11.95 (s, 1H), 10.29 (s, 1H), 8.66 (dd, J=4.9, 1.7 Hz, 1H), 8.65-8.62 (m, 1H), 7.73 (dt, J=7.8, 2.0 Hz, 1H), 7.41 (d, J=8.4 Hz, 1H), 7.37 (ddd, J=7.8, 4.9, 0.9 Hz, 1H), 6.59-6.54 (m, 1H), 6.40 (d, J=7.0 Hz, 1H), 4.39-4.30 (m, 2H), 4.19 (s, 2H), 3.15 (s, 1H), 1.97-1.78 (m, 4H), 1.72-1.56 (m, 2H). MS found for C₁₉H₂₀N₂O₄: 341.3.

GBT001579

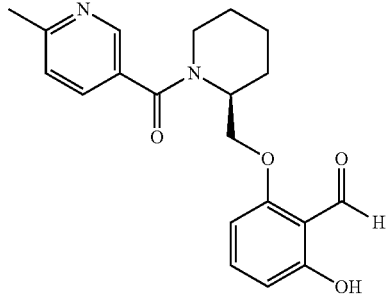

(S)-2-hydroxy-6-((1-(6-methylnicotinoyl)piperidin-2-yl)methoxy)benzaldehyde

GBT1579—(S)-2-hydroxy-6-((1-(6-methylnicotinoyl)piperidin-2-yl)methoxy)benzaldehyde

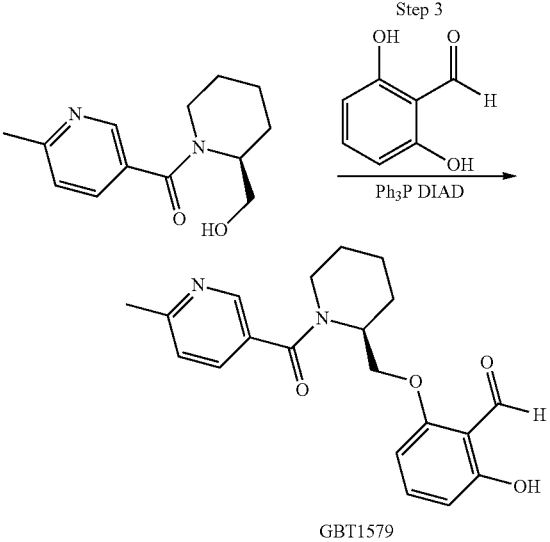

Steps 1&2: To a suspension of 6-methylnicotinic acid (270 mg, 2 mmol) in DCM (5 mL) was added oxalyl chloride (0.34 mL, 4 mmol) at 0° C. followed by a drop of DMF, after stirred for 2 hour at room temperature, the solution was concentrated to give crude acid chloride.

To the above crude acid chloride in DCM (4 mL) was added (S)-piperidin-2-ylmethanol hydrochloride (300 mg, 1.98 mmol) and DIPEA (1.04 mL, 5.94 mmol) at 0° C., after stirred at room temperature for 2 h, more DIPEA was added to drive the reaction to completion. The reaction was diluted with DCM, washed with Sat. NaHCO₃, brine, dried and concentrated to give crude product, which was purified by column (DCM/MeOH=90:10) to give desired (S)-(2-(hydroxymethyl)piperidin-1-yl)(6-methylpyridin-3-yl)methanone (100 mg).

Step 3: To a solution of (S)-(2-(hydroxymethyl)piperidin-1-yl)(6-methylpyridin-3-yl)methanone (100 mg, 0.43 mmol) and 2,6-dihydroxybenzaldehyde (80 mg, 0.56 mmol) in THF (2.5 mL) at 0° C. was added polymer supported triphenylphosphine (435 mg, 0.52 mmol) and DIAD (0.11 mL, 0.52 mmol), after stirred for 4 hour at room temperature, the solution was filtered, the filtrate was concentrated and was purified by prep HPLC to give (S)-2-hydroxy-6-((1-(6-methylnicotinoyl)piperidin-2-yl)methoxy)benzaldehyde (29 mg). ¹H NMR (400 MHz, Chloroform-d) δ 11.95 (s, 1H), 10.28 (s, 1H), 8.53 (d, J=2.2 Hz, 1H), 7.62 (dd, J=8.0, 2.3 Hz, 1H), 7.39 (t, J=8.4 Hz, 1H), 7.21 (d, J=8.0 Hz, 1H), 6.55 (dd, J=8.5, 0.8 Hz, 1H), 6.40 (s, 1H), 4.33 (t, J=8.6 Hz, 2H), 4.19 (s, 1H), 3.09 (s, 2H), 2.59 (s, 3H), 1.73 (m, 6H). MS (M+H) found for C₂₀H₂₂N₂O₄: 355.3.

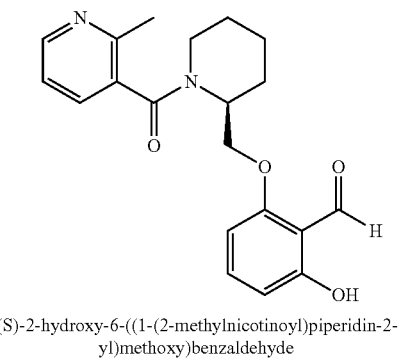

(S)-2-hydroxy-6-((1-(2-methylnicotinoyl)piperidin-2-yl)methoxy)benzaldehyde

GBT1580—(S)-2-hydroxy-6-((1-(2-methylnicotinoyl)piperidin-2-yl)methoxy)benzaldehyde

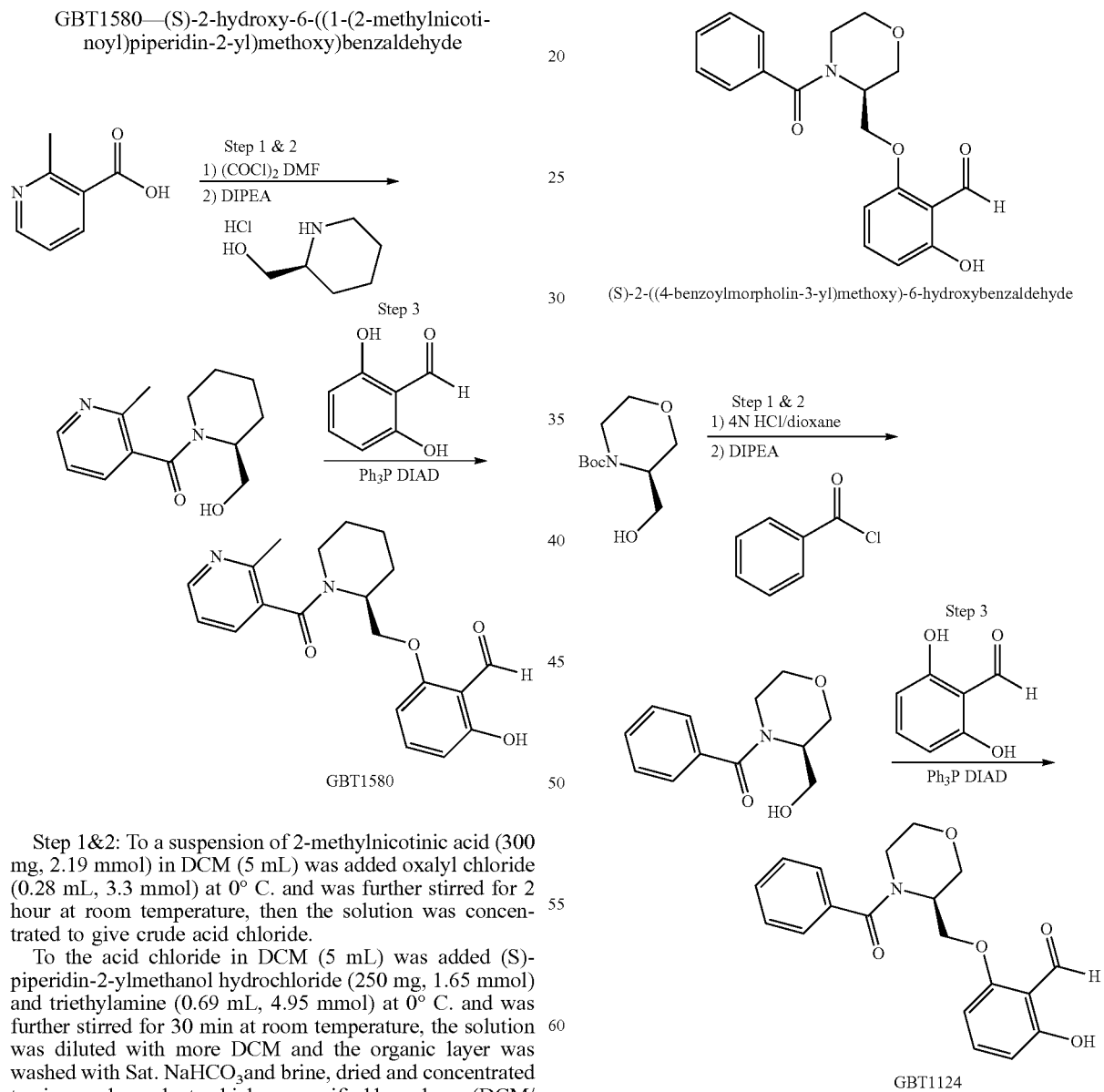

Step 1&2: To a suspension of 2-methylnicotinic acid (300 mg, 2.19 mmol) in DCM (5 mL) was added oxalyl chloride (0.28 mL, 3.3 mmol) at 0° C. and was further stirred for 2 hour at room temperature, then the solution was concentrated to give crude acid chloride.

To the acid chloride in DCM (5 mL) was added (S)-piperidin-2-ylmethanol hydrochloride (250 mg, 1.65 mmol) and triethylamine (0.69 mL, 4.95 mmol) at 0° C. and was further stirred for 30 min at room temperature, the solution was diluted with more DCM and the organic layer was washed with Sat. NaHCO₃ and brine, dried and concentrated to give crude product, which was purified by column (DCM/MeOH=95:5) to give (S)-(2-(hydroxymethyl)piperidin-1-yl)(2-methylpyridin-3-yl)methanone (200 mg).

Step 3: To a solution of (S)-(2-(hydroxymethyl)piperidin-1-yl)(2-methylpyridin-3-yl)methanone (180 mg, 0.77 mmol) and 2,6-dihydroxybenzaldehyde (140 mg, 1.0 mmol) in THF (5 mL) at 0° C. was added polymer supported triphenylphosphine (1.0 g, 1.16 mmol) and DIAD (0.21 mL, 1.08 mmol), after stirred for 15 hour at room temperature, the solution was filtered, the filtrate was concentrated and was purified by prep HPLC to give (S)-2-hydroxy-6-((1-(2-methylnicotinoyl)piperidin-2-yl)methoxy)benzaldehyde (129 mg). $^1$H NMR (400 MHz, Chloroform-d) δ 11.99 (s, 1H), 10.40 (s, 1H), 8.53 (m, 1H), 7.42 (t, J=8.4 Hz, 1H), 7.32 (m, 1H), 7.20 (m, 1H), 6.56 (d, J=8.4 Hz, 1H), 6.47 (d, J=8.3 Hz, 1H), 5.39 (s, 1H), 4.38 (t, J=8.8 Hz, 1H), 4.21 (dd, J=9.5, 6.6 Hz, 1H), 3.36 (d, J=13.5 Hz, 1H), 3.14 (m, 1H), 2.52 (s, 3H), 2.10-1.35 (m, 6H). MS (M+H) found for $C_{20}H_{22}N_2O_4$ 355.3.

Step 1&2: To a solid sample of (R)-tert-butyl 3-(hydroxymethyl)morpholine-4-carboxylate (150 mg, 0.69 mmol) was added 4N HCl in dioxane (1.5 mL). After stirred for 30 min, it was concentrated to give (R)-(3-(hydroxymethyl)morpholino)(phenyl)methanone as HCl salt. To a suspension of (R)-(3-(hydroxymethyl)morpholino)(phenyl)methanone HCl salt in DCM (2 mL) at 0° C. was added DIPEA (0.36 mL, 2.07 mmol) and benzoyl chloride (0.08 mL, 0.69 mmol). After stirred for 30 min, it was diluted with DCM, washed with aqueous Sat. NaHCO₃, brine, dried and concentrated to give crude product, which was purified by column (100% EtOAc) to give (R)-(3-(hydroxymethyl)morpholino)(phenyl)methanone (120 mg). Step 3. To a solution of (R)-(3-(hydroxymethyl)morpholino)(phenyl)methanone (80 mg, 0.36 mmol) and 2,6-dihydroxybenzaldehyde (0.06 g, 0.47 mmol) in THF (2 mL) was added PPh₃ (polymer supported, 0.45 g, 0.54 mmol) and DIAD (0.11 mL, 0.54 mmol) at 0° C. and stirred at room temperature for 2 h, it was subsequently concentrated, the resulting residue was purified by preparative HPLC to give (S)-2-((4-benzoylmorpholin-3-yl)methoxy)-6-hydroxybenzaldehyde (20 mg). $^1$H NMR (400 MHz, Chloroform-d) δ 11.96 (s, 1H), 10.28 (s, 1H), 7.50-7.35 (m, 7H), 6.61-6.41 (m, 1H), 4.37 (s, 2H), 4.07 (s, 1H), 3.89 (s, 1H), 3.76 (dd, J=12.2, 3.2 Hz, 1H), 3.55 (s, 2H), 3.39 (s, 1H), 1.35-1.18 (m, 1H). MS found for $C_{19}H_{19}NO_5$: 342.3.

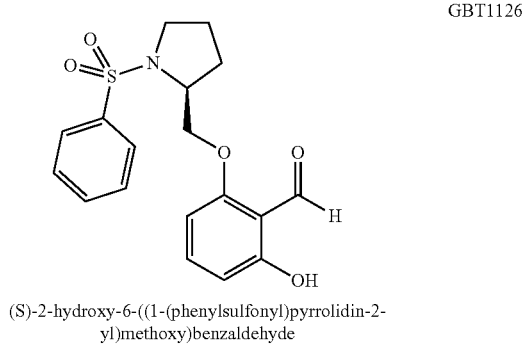 [SMILES: O=Cc1c(O)cccc1OC[C@@H]1CCCN1S(=O)(=O)c1ccccc1]

(S)-2-hydroxy-6-((1-(phenylsulfonyl)pyrrolidin-2-yl)methoxy)benzaldehyde

GBT1126—(S)-2-hydroxy-6-((1-(phenylsulfonyl)pyrrolidin-2-yl)methoxy)benzaldehyde

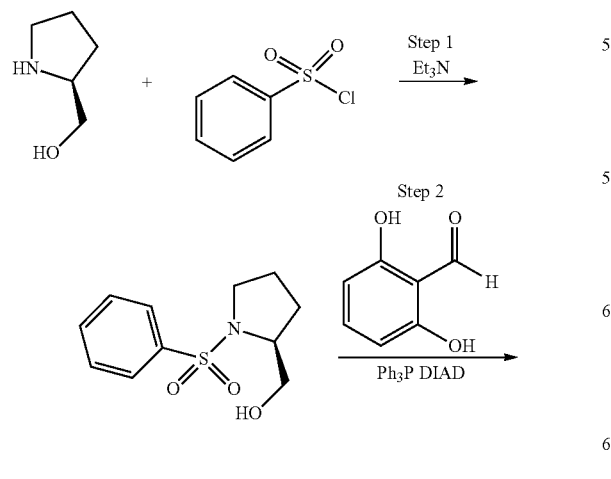

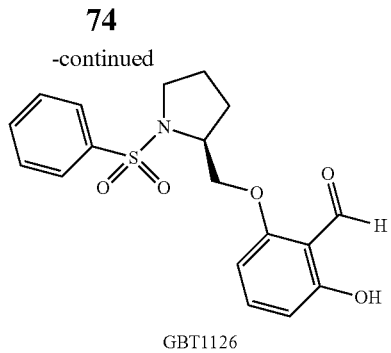

GBT1126

Step 1: To a solution of (S)-pyrrolidin-2-ylmethanol (500 mg, 4.94 mmol) in DCM (10 mL) at 0° C. was added TEA (1.04 mL, 7.41 mmol) followed by benzenesulfonyl chloride (0.63 mL, 4.94 mmol). After stirred for 30 min, it was diluted with DCM, washed with aqueous Sat. NaHCO₃, brine, dried and concentrated to give crude product, which was purified by column to (S)-(1-(phenylsulfonyl)pyrrolidin-2-yl)methanol.

Step 2: To a solution of (S)-(1-(phenylsulfonyl)pyrrolidin-2-yl)methanol (125 mg, 0.54 mmol) and 2,6-dihydroxybenzaldehyde (0.1 g, 0.7 mmol) in THF (2 mL) was added PPh₃ (0.21 g, 0.81 mmol) and DIAD (0.16 mL, 0.81 mmol) at 0° C. and stirred at room temperature for 2 h, it was subsequently concentrated, the resulting residue was purified by preparative HPLC to give (S)-2-hydroxy-6-((1-(phenylsulfonyl)pyrrolidin-2-yl)methoxy)benzaldehyde (37 mg). $^1$H NMR (400 MHz, Chloroform-d) δ 11.90 (d, J=0.4 Hz, 1H), 10.28 (d, J=0.6 Hz, 1H), 7.93-7.76 (m, 2H), 7.65-7.56 (m, 1H), 7.56-7.47 (m, 2H), 7.43 (td, J=8.4, 0.4 Hz, 1H), 6.55 (dt, J=8.5, 0.7 Hz, 1H), 6.48 (dd, J=8.3, 0.8 Hz, 1H), 4.42-4.31 (m, 1H), 4.08-3.95 (m, 2H), 3.56-3.45 (m, 1H), 3.20 (ddd, J=10.0, 8.0, 7.0 Hz, 1H), 2.03-1.83 (m, 2H), 1.81-1.50 (m, 2H). MS found for $C_{18}H_{19}NO_5S$: 362.4.

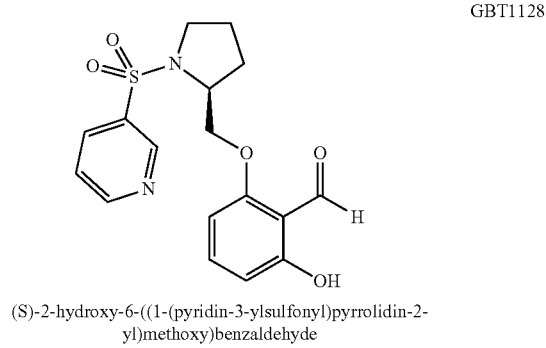 [SMILES: O=Cc1c(O)cccc1OC[C@@H]1CCCN1S(=O)(=O)c1cccnc1]

(S)-2-hydroxy-6-((1-(pyridin-3-ylsulfonyl)pyrrolidin-2-yl)methoxy)benzaldehyde

GBT1128—(S)-2-hydroxy-6-((1-(pyridin-3-ylsulfonyl)pyrrolidin-2-yl)methoxy)benzaldehyde

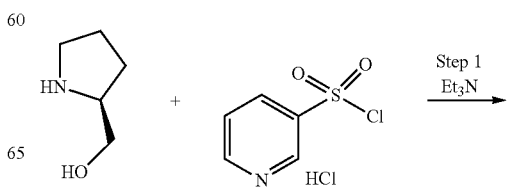

75
-continued

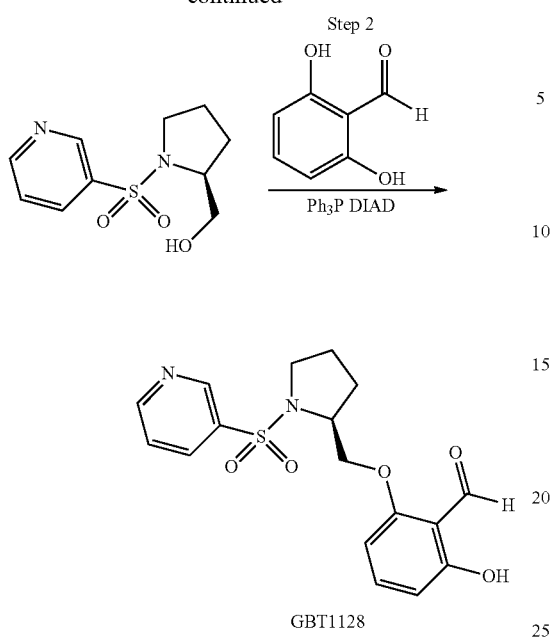

GBT1128

Step 1: To a solution of (S)-pyrrolidin-2-ylmethanol (320 mg, 3.16 mmol) in DCM (6 mL) at 0° C. was added TEA (0.97 mL, 6.95 mmol) followed by pyridine-3-sulfonyl chloride (0.68 g, 3.16 mmol). After stirred for 30 min, it was diluted with DCM, washed with aqueous Sat. NaHCO$_3$, brine, dried and concentrated to give crude product, which was purified by column to give (S)-(1-(pyridin-3-ylsulfonyl) pyrrolidin-2-yl)methanol (66 mg).

Step 2: To a solution of (S)-(1-(pyridin-3-ylsulfonyl) pyrrolidin-2-yl)methanol (65 mg, 0.29 mmol) and 2,6-dihydroxybenzaldehyde (0.06 g, 0.41 mmol) in THF (2 mL) was added PPh$_3$ (polymer supported, 0.37 g, 0.44 mmol) and DIAD (0.09 mL, 0.44 mmol) at 0° C. and stirred at room temperature for 2 h, it was subsequently diluted with AcCN, the insoluble material was filtered off, the filtrate was concentrated, the resulting residue was purified by preparative HPLC to give (S)-2-hydroxy-6-((1-(pyridin-3-ylsulfonyl)pyrrolidin-2-yl)methoxy)benzaldehyde (17 mg). $^1$H NMR (400 MHz, Chloroform-d) δ 11.90 (s, 1H), 10.29 (d, J=0.6 Hz, 1H), 9.08 (dd, J=2.3, 0.9 Hz, 1H), 8.83 (dd, J=4.9, 1.6 Hz, 1H), 8.18-8.09 (m, 1H), 7.53-7.46 (m, 1H), 7.44 (t, J=8.4 Hz, 1H), 6.61-6.54 (m, 1H), 6.50-6.44 (m, 1H), 4.40-4.31 (m, 1H), 4.12-3.96 (m, 2H), 3.56 (ddd, J=10.5, 7.1, 4.2 Hz, 1H), 3.21 (dt, J=10.1, 7.4 Hz, 1H), 2.08-1.88 (m, 2H), 1.87-1.66 (m, 2H). MS (M+H) found for C$_{17}$H$_{18}$N$_2$O$_5$S: 363.4.

From the foregoing it will be appreciated that, although specific embodiments of the invention have been described herein for purposes of illustration, various modifications may be made without deviating from the spirit and scope of the invention.

Throughout the description of this invention, reference is made to various patent applications and publications, each of which are herein incorporated by reference in their entirety.

76

What is claimed is:

1. A compound of formula:

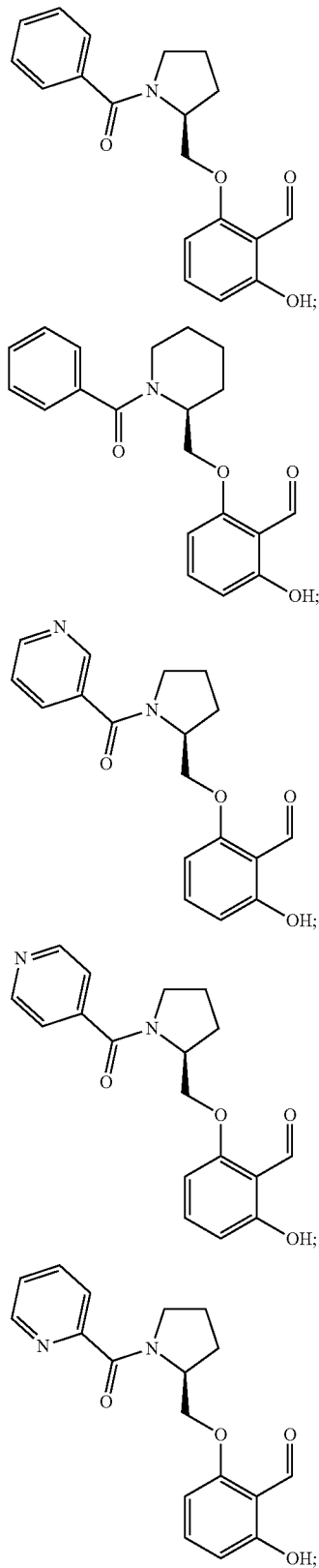

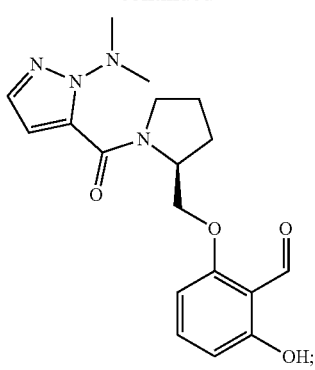
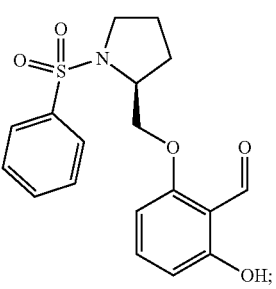
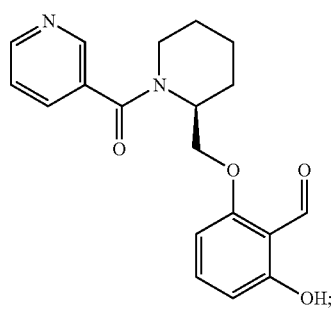
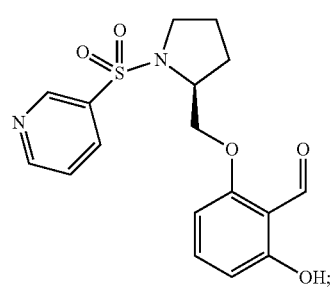
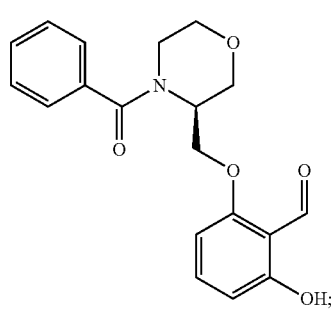
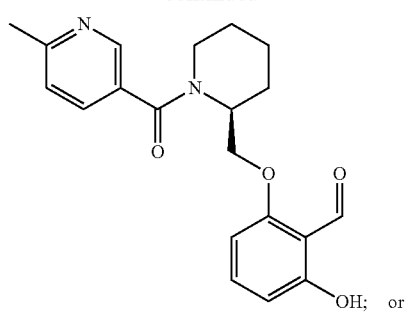
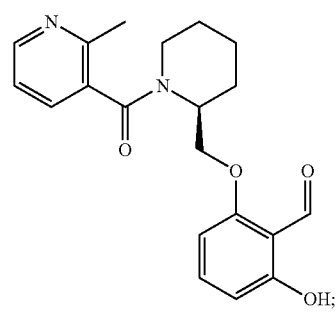
or a tautomer thereof, or a pharmaceutically acceptable salt of each thereof.
2. A compound of formula:
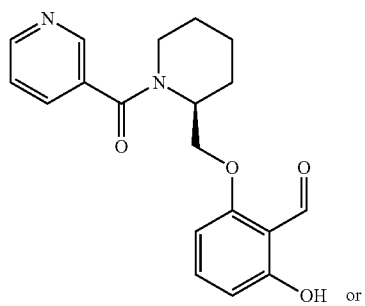
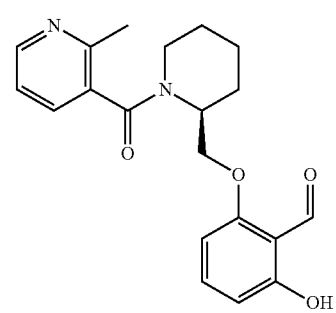
or a pharmaceutically acceptable salt of each thereof.

3. A compound of formula:

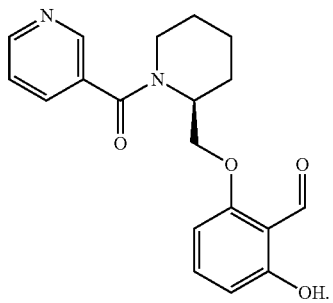 [SMILES: O=Cc1c(O)cccc1OC[C@@H]1CCCCN1C(=O)c1cccnc1]

4. A compound of formula:

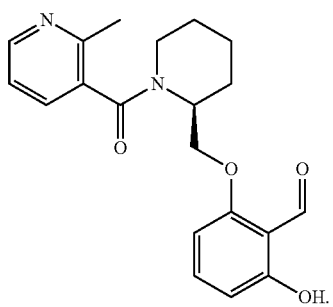 [SMILES: Cc1ncccc1C(=O)N1CCCC[C@H]1COc1cccc(O)c1C=O]

5. The compound of claim 1, wherein the compound is:

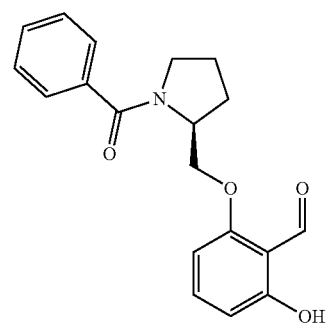 [SMILES: O=Cc1c(O)cccc1OC[C@@H]1CCCN1C(=O)c1ccccc1]

or a pharmaceutically acceptable salt thereof.

6. The compound of claim 1, wherein the compound is:

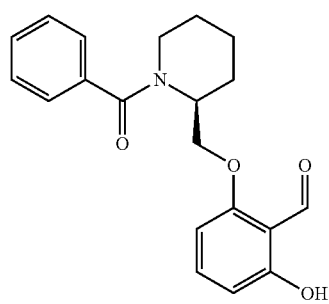 [SMILES: O=Cc1c(O)cccc1OC[C@@H]1CCCCN1C(=O)c1ccccc1]

or a pharmaceutically acceptable salt thereof.

7. The compound of claim 1, wherein the compound is:

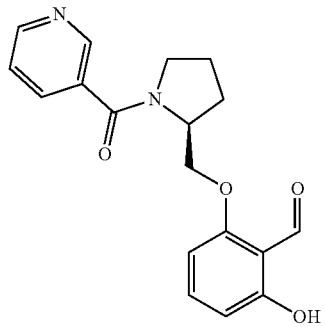 [SMILES: O=Cc1c(O)cccc1OC[C@@H]1CCCN1C(=O)c1cccnc1]

or a pharmaceutically acceptable salt thereof.

8. The compound of claim 1, wherein the compound is:

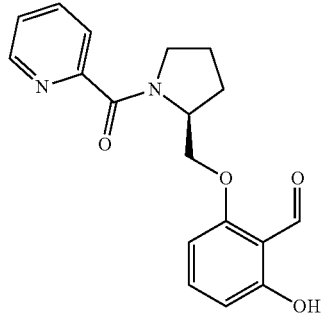 [SMILES: O=Cc1c(O)cccc1OC[C@@H]1CCCN1C(=O)c1ccccn1]

or a pharmaceutically acceptable salt thereof.

9. The compound of claim 1, wherein the compound is:

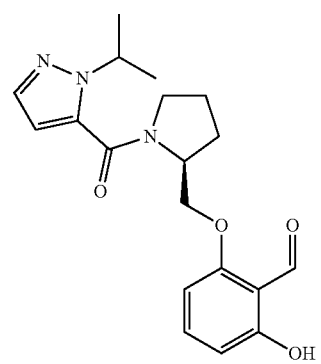 [SMILES: CC(C)n1nccc1C(=O)N1CCC[C@H]1COc1cccc(O)c1C=O]

or a pharmaceutically acceptable salt thereof.

10. The compound of claim 1, wherein the compound is:

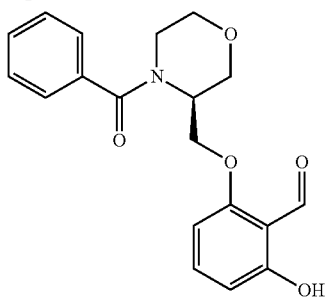 [SMILES: O=Cc1c(O)cccc1OC[C@@H]1COCCN1C(=O)c1ccccc1]

or a pharmaceutically acceptable salt thereof.

11. The compound of claim 1, wherein the compound is:

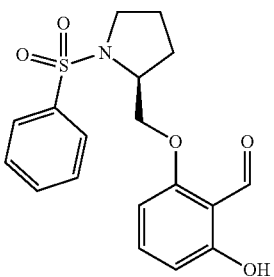 [SMILES: O=Cc1c(O)cccc1OC[C@@H]1CCCN1S(=O)(=O)c1ccccc1]

or a pharmaceutically acceptable salt thereof.

12. The compound of claim 1, wherein the compound is:

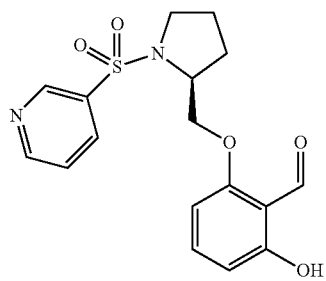 [SMILES: O=Cc1c(O)cccc1OC[C@@H]1CCCN1S(=O)(=O)c1cccnc1]

or a pharmaceutically acceptable salt thereof.

13. The compound of claim 1, wherein the compound is:

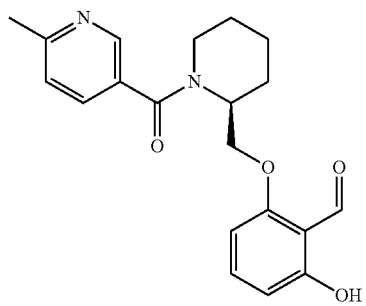 [SMILES: Cc1ccc(C(=O)N2CCCC[C@H]2COc2cccc(O)c2C=O)cn1]

or a pharmaceutically acceptable salt thereof.

14. The compound of claim 1, wherein the compound is:

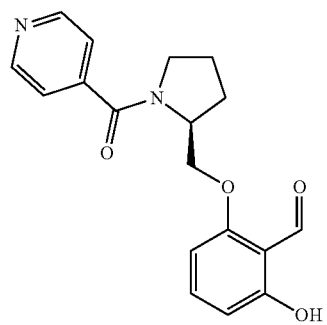 [SMILES: O=Cc1c(O)cccc1OC[C@@H]1CCCN1C(=O)c1ccncc1]

or a pharmaceutically acceptable salt thereof.

* * * * *

UNITED STATES PATENT AND TRADEMARK OFFICE
CERTIFICATE OF CORRECTION

PATENT NO. : 10,450,269 B1  
APPLICATION NO. : 16/446331  
DATED : October 22, 2019  
INVENTOR(S) : Qing Xu et al.

Page 1 of 1

It is certified that error appears in the above-identified patent and that said Letters Patent is hereby corrected as shown below:

In the Claims

In Claim 1, Column 77, Lines 1-15, please replace

" 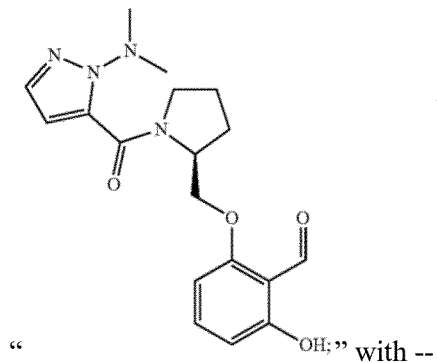 " with -- 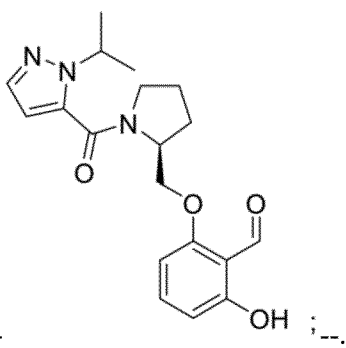 ;--.

Signed and Sealed this  
Twentieth Day of July, 2021

Drew Hirshfeld  
*Performing the Functions and Duties of the  
Under Secretary of Commerce for Intellectual Property and  
Director of the United States Patent and Trademark Office*